Figure 1:
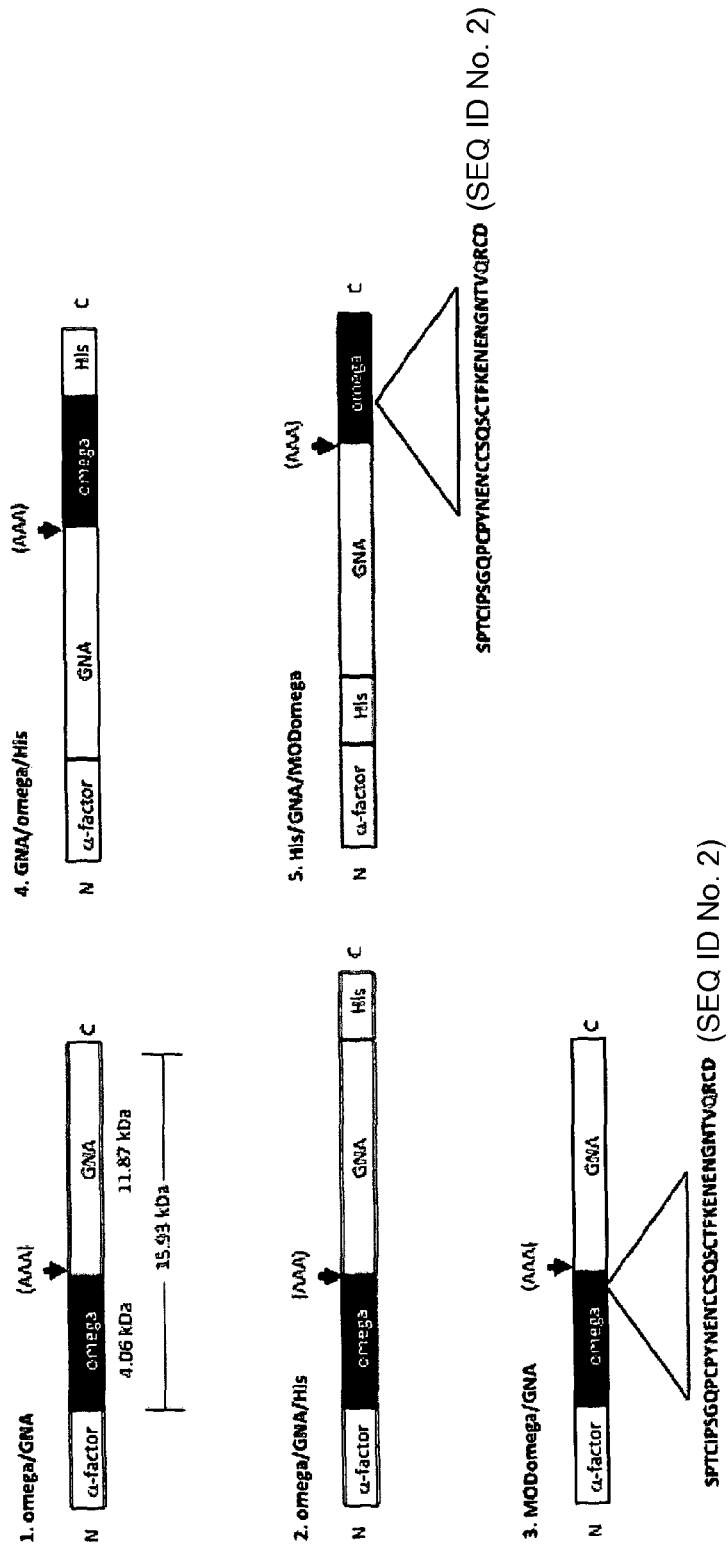

(12) United States Patent
Gatehouse et al.

US010117433B2

(10) Patent No.: US 10,117,433 B2
(45) Date of Patent: Nov. 6, 2018

(54) PESTICIDES

(75) Inventors: John A. Gatehouse, Durham (GB);
Elaine C. Fitches, Sand Hutton (GB)

(73) Assignees: University of Durham, Durham (GB);
The Secretary of State for Environment, Food and Rural Affairs, York (GB)

( * ) Notice: Subject to any disclaimer, the term of this patent is extended or adjusted under 35 U.S.C. 154(b) by 928 days.

(21) Appl. No.: 14/008,412

(22) PCT Filed: Mar. 29, 2012

(86) PCT No.: PCT/GB2012/000287
§ 371 (c)(1),
(2), (4) Date: Dec. 17, 2013

(87) PCT Pub. No.: WO2012/131302
PCT Pub. Date: Oct. 4, 2012

(65) Prior Publication Data
US 2014/0366227 A1   Dec. 11, 2014

(30) Foreign Application Priority Data

Mar. 31, 2011 (GB) .................................. 1105418.6

(51) Int. Cl.
*C07K 14/42* (2006.01)
*C12N 15/82* (2006.01)
*A01N 43/50* (2006.01)
*A01N 37/46* (2006.01)
*A01N 63/02* (2006.01)
*C07K 14/435* (2006.01)
*C12N 15/62* (2006.01)
*A01H 5/00* (2018.01)

(52) U.S. Cl.
CPC .............. *A01N 43/50* (2013.01); *A01H 5/00* (2013.01); *A01N 37/46* (2013.01); *A01N 63/02* (2013.01); *C07K 14/42* (2013.01); *C07K 14/43518* (2013.01); *C12N 15/62* (2013.01); *C12N 15/8279* (2013.01); *C12N 15/8285* (2013.01); *C12N 15/8286* (2013.01); *C07K 2319/00* (2013.01); *C07K 2319/21* (2013.01); *Y02A 40/162* (2018.01); *Y02A 40/164* (2018.01)

(58) Field of Classification Search
None
See application file for complete search history.

(56) References Cited

U.S. PATENT DOCUMENTS

| | | | |
|---|---|---|---|
| 5,763,568 A | 6/1998 | Atkinson et al. | |
| 6,006,470 A * | 12/1999 | Geoghegan | C07K 14/42 |
| | | | 47/58.1 R |
| 7,196,057 B2 * | 3/2007 | Gatehouse | A01N 63/02 |
| | | | 424/94.61 |
| 7,354,993 B2 † | 4/2008 | King | |
| 7,575,758 B2 | 8/2009 | King et al. | |
| 2004/0138423 A1 | 7/2004 | King et al. | |
| 2007/0066529 A1 * | 3/2007 | King | A01N 63/02 |
| | | | 424/405 |
| 2016/0311867 A1 | 10/2016 | Fitches et al. | |

FOREIGN PATENT DOCUMENTS

| | | | | |
|---|---|---|---|---|
| WO | WO 9958705 A1 * | 11/1999 | ............ | A01N 63/00 |
| WO | WO-9958705 A1 * | 11/1999 | ............ | A01N 63/00 |
| WO | 2003/014150 | 2/2003 | | |
| WO | 2003/014150 A2 | 2/2003 | | |
| WO | 2005/025312 | 3/2005 | | |
| WO | 2006/052806 | 5/2006 | | |
| WO | 2006/052806 A2 | 5/2006 | | |
| WO | 2012131302 | 10/2012 | | |
| WO | 2013026105 | 2/2013 | | |

OTHER PUBLICATIONS

Van Damme et al (Accession ID M55556.1, public available Apr. 27, 1993).*
Van Damme et al (Biosynthesis, primary structure and molecular cloning of snowdrop (*Galanthus nivalis* L.) lectin. Eur. J. Biochem. 202, 23-30, 1991).*
Hogervorst et al (Direct effects of snowdrop lectin (GNA) on larvae of three aphid predators and fate of GNA after ingestion. Journal of Insect Physiology 52: 614-624, 2006).*
Fitches et al., "Fusion proteins containing insect-specific toxins as pest control agents: snowdrop lectin delivers fused insecticidal spider venom toxin to insect haemolymph following oral ingestion," Journal of Insect Physiology, 2004, 50: 61-71.
European Search Report completed for European Applcation No. GB1105418.6, dated Feb. 15, 2012.
Trung et al., "A fusion protein containing a lepidopteran-specific toxin from the South Indian red scorpion (*Mesobuthus tamulus*) and snowdrop lectin shows oral toxicity to target insects," BMC Biotechnology, Biomed Central Ltd., vol. 6, No. 1, Mar. 16, 2006.
Sher et al., "Spider venom toxin protects plants from insect attack," Transgenic Research, Kluwer Academic Publishers-Plenum Publishers, NE, vol. 15, No. 3, Jun. 1, 2006.
Down et al., "Insecticidal spider venom toxin fused to snowdrop lectin is toxic to the pe

(56) References Cited

OTHER PUBLICATIONS

Chong et al., "The omega-atracotoxins: Selective blockers of insect M-LVA and HVA calcium channels," Biochemical Pharmacology, vol. 74, No. 4, (2007), pp. 623-638.
Fitches et al. "New environmentally-friendly technologies for slug control based on orally-delivered fusion proteins containing specific molluscicidal toxins," Novara (May 2012) 86 pages, URL:http://randd.defra.gov.uk/Document.aspx?Document=12094_FinalreportLK0991.pdf.
Kozlov et al., "A Novel Strategy for the Identification of Toxinlike Structures in Spider Venom," Proteins : Structure, Function, and Bioinformatics, vol . 59, No. 1, (2005), pp. 131-140.
PCT/GB2014/053663 International Search Report dated Sep. 3, 2015 (4 pages).
Pyati et al. "Optimising expression of the recombinant fusion protein biopesticide [omega]-hexatoxin-Hvla/GNA in Pichia pastoris: sequence modifications and a simple method for the generation of multi-copy strains", Journal of Industrial Microbiology & Biotechnology, vol . 41, No. 8, (2014), pp. 1237-1247.
Wong et al., "SVM-Based Prediction of Propeptide Cleavage Sites in Spider Toxins Identifies Toxin Innovation in an Australian Tarantula," PLOS ONE, vol . 8, No. 7, (2013) p. e66279.
Fitches et al., "An evaluation of garlic lectin as an alternative carrier domain for insecticidal fusion proteins," article 483 Sciences Insect Science (2008) 15, 483-495, DOI 10.1111/j.1744-7917.2008.00237.x, Journal compilation © Institute of Zoology, Chinese Academy of Sciences.
Fitches et al., "The insecticidal activity of recombinant garlic lectins towards aphids," article, Insect Biochemistry and Molecular Biology 38 (2008) 905-915, Elsevier Ltd.
Peumans et al., "Lectins as Plant Defense Proteins," article, Plant Physiol. (1995) 109: 347-352, Laboratory for Phytopathology and Plant Protection, Katholieke Universiteit Leuven.
Tedford et al., "Australian funnel-web spiders: master insecticide chemists," article, Toxicon 43 (2004) 601-618, Elsevier Ltd.
Fitches et al., "In vitro and in vivo binding of snowdrop (*Galanthus nivalis agglutinin*; GNA) and jackbean (*Canavalia ansiformis*; Con A) lectins within tomato moth (*Lacanobia oleracea*) larvae; mechanisms of insecticidal action," J. Insect Physiol., 47: 777-787 (2001).
Fitches et al., "Fusion proteins containing neuropeptides as novel insect control agents: snowdrop lectin delivers fused allatostatin to insect haemolymph following oral ingestion," J. Insect Biochem. Mol. Biol., 32: 1653-1661 (2002).
Powell et al., "Immunohistochemical and developmental studies to elucidate the mechanism of action of the snowdrop lectin on the rice brown planthopper, Nilaparvata lugens (Stal)," J. Insect Physiol., 44: 529-539 (1998).
Bloomquist, "Mode of action of atracotoxin at central and peripheral synapses of insects," article (2003) pp. 45-50.
Brown et al., "Differentially Regulated Inhibitor-Sensitive and Insensitive Protease Genes from the Phytophagous Insect Pest, Helicoverpa armigera, are Members of Complex Multigene Families," article (1997) vol. 27, No. 7, pp. 625-638.
Catterall, "Structure and Regulation of Voltage-Gated Ca2+ Channels," article (2000) pp. 521-555.
Cino, "High Yield Protein Production from Pichia pastoris Yeast: A Protocol for Benchtop Fermentation," article (May 1999) pp. 1-12.
Cregg et al., "Recent Advances in the Expression of Foreign Genes in Pichia pastoris," article (1993) vol. 11, pp. 905-910.
Douglas et al., "Synthesis of the Essential Amino Acid Tryptophan in the Pea Aphid (*Acyrthosiphon pisum*) Symbiosis," article (1992) vol. 38, No. 8, pp. 565-568.
Fitches, "A comparison of the short and long term effects of insecticidal lectins on the activities of soluble and brush border enzymes of tomato moth larvae," article (1998) pp. 1213-1224.
Fletcher et al., "The Structure of a Novel Insecticidal Neurotoxin, w-atractoxin-HV1, from the venom of an Australian funnel web spider," article (1997) vol. 4, No. 7, pp. 559-566.
Gordon et al., "The differential preference of scorpion x-toxins for insect or mammalian sodium channels: Implications for improved insect control," article (2006) pp. 452-472.
Khan et al., "Spider Venom Toxin Protects Plants from Insect Attack," article (2006) pp. 349-357.
Laurino et al., "Toxicity of Neonicotinoid Insecticides to Honey Bees: Laboratory Tests," article (2011) pp. 107-113.
Mukherjee et al., "Orally Active Acaricidal Peptide Toxins from Spider Venom," article (2006) pp. 182-187.
OECD/OCDE, "OECD Guidelines for the Testing of Chemicals—Honeybees, Acute Oral Toxicity Test—Document 213," article (1998) pp. 1-8.
OECD/OCDE, "OECD Guidelines for the Testing of Chemicals—Honeybees, Acute Oral Toxicity Test—Document 214" article (1998) pp. 1-7.
Raemaekers et al., "Functional Phytohemaggultinin (PHA) and Galanthus nivalis aggultinin (GNA) expressed in Pichia Pastoris," article (1999) pp. 394-403.
Tedford et al., "Functional Significance of the b-Hairpin in the Insecticidal Neurotoxin w-Atracotoxin-Hv1a," article (2001) vol. 276, No. 28, pp. 26568-26576.
Tedford et al., "Scanning Mutagenesis of—Atracotoxin-Hv1a Reveals a Spatially Restricted Epitope That Confers Selective Activity against Insect Calcium Channels," article (2004) pp. 44133-44140.
Kalapothakis et al., "Cloning of cDNAs Encoding Neurotoxic Peptdes from the Spider Phoneutria Nigriventer," Toxicon (1998) pp. 1843-1850.
Liao et al., "Solution Structure and Functional Characterization of Jingzhaotosin-XI:Novel Gating Modifier of both Potassium and Sodium Channels," Biochemistry (2006) 15591-15600.
Office Action from the US Patent and Trademark Office for U.S. Appl. No. 15/103,810 dated Aug. 9, 2017 (18 pages).
Fitches Fusion to Snowdrop Lectin Magnifies the Oral Activity of Insecticidal 1 Hexatoxin Hv1a Peptide by Enabling Its Delivery to the Central Nervous System pp. 1 Jun. 11, 2012.†
Down Insecticidal spider venom toxin fused to snowdrop lectin is toxic to the peach potato aphid Myzus persicae Hemiptera Aphididae and the rice brown planthopper Nilaparvata lugens Hemiptera Delphacidae pp. 77-85 2006 Pest Management Science.†

* cited by examiner
† cited by third party

Figure 3

(A)  (B)

Time (hours)

(A)

(B)

PG Vector

(C)

PGH Vector

PESTICIDES

CROSS-REFERENCE TO RELATED APPLICATIONS

This application is a national stage entry under 35 U.S.C. § 371(b) of International Application No. PCT/GB2012/000287, filed Mar. 29, 2012, which claims the benefit of United Kingdom Patent Application Serial No. 1105418.6, filed Mar. 31, 2011, the disclosures of which are hereby incorporated herein by reference.

The present invention relates to the development of fusion proteins based on peptide toxins as pesticides. The invention also relates to transgenic plants encoding said peptides and their utility in pest management.

Against a background of increasing global population, the pressures on food production systems to become more efficient are ever increasing. Pests are still a major constraint on crop production despite progress in crop protection measures and the development of host resistance. Estimates of potential losses worldwide for the top six crops vary from 25-80% (40% for potato). Some pests and diseases can be controlled by the application of agrochemicals and careful crop management practices including deploying resistant cultivars. However, there remains a need to develop new and effective pest control systems.

In the past most research on developing pesticides focused on the identification of new chemical entities that could be used for such purposes. However in recent years there has been an increasing trend towards identifying new types "biopesticides" that can be used for pest management. Biopesticides are generally considered as naturally occurring substances (biochemical pesticides) that control pests, microorganisms that control pests (microbial pesticides), and pesticidal substances produced by plants containing added genetic material: plant-incorporated protectants. Conventional pesticides, by contrast, are generally synthetic materials that directly kill or inactivate the pests. The perceived benefits of biopesticides include: a lack of harmful residues; reduced impact on non-target species; and in the long term they may be cheaper and more effective than chemical pesticides. It is also noteworthy that there has been recent legislative drive towards the development of non-chemical pesticides.

A well known example of a biopesticide is Bt-toxin, which functions as an insecticide. Transgenic maize and cotton plants have been developed which synthesise the Bt toxin thus providing a defense to the plant against insect pests.

U.S. Pat. No. 7,196,057 discusses various fusion proteins for use in insect control and in particular *Manduca sexta* allatostatin (Manse-AS) fused with snowdrop lectin (GNA).

Fitches et al (J. Insect Physiol., Vol. 50, 2004, p 62-71) describes the use of fusion proteins of *Segestria floerntina* toxin 1 (SF11) with GNA.

Neuropeptide toxins synthesised as venom by spiders and other arthropods have been the subject of research for development as biopesticides. WO2006/052806, WO2005/025312 and US2007/0066529 describe the use of spider toxin venom peptides for use as a biopesticide and Khan, S. A., et al., (Transgenic Research., Vol. 15, 2006, p 349-357) described expression of spider venom toxin in plants to protect the plants from insect attack. The present inventors therefore decided to investigate the utility of further spider toxins as pesticides. They have surprisingly found that omega atracotoxin family member 1a derived from the funnel-web spider *Hadronyche versuta* ($\omega$-ACTX-Hv1a), a toxin derived from the funnel-web spider *Hadroncyhe versuta*, when fused to a protein capable of mediating translocation of the fusion protein from the invertebrate gut, can function as an effective pesticide against a broad range of pests.

Accordingly, a first aspect of the invention provides a fusion protein comprising: (i) a $\omega$-ACTX-Hv1a protein toxin, or a fragment or variant thereof, linked to (ii) a protein capable of mediating translocation of the fusion protein from the invertebrate gut.

The fusion protein of the first aspect of the invention comprises a $\omega$-ACTX-Hv1a protein toxin, or a fragment or variant thereof, as a first portion, linked to a protein capable of mediating translocation of the fusion protein from the invertebrate gut as a second portion.

The $\omega$-ACTX-Hv1a protein toxin is known in the art. It is a toxin isolated from the funnel-web spider *Hadroncyhe versuta*. The amino acid sequence of $\omega$-ACTX-Hv1a is known, as is nucleic acid sequence encoding the $\omega$-ACTX-Hv1a (as presented below). $\omega$-ACTX-Hv1a is a calcium channel antagonist; it has previously been shown that $\omega$-ACTX-Hv1a can block invertebrate but not vertebrate calcium channels. This is an important point since in most circumstances it is clearly desirable to use pesticides which do not have any activity against vertebrate animals, so as to avoid any adverse effects on humans or domesticated animals.

It has previously been reported that $\omega$-ACTX-Hv1a can be used on its own as a pesticide when applied topically to caterpillars (see Khan et al identified above). However the authors report topical application of the peptide in a solution containing imidazole which is known to be insecticidal in its own right. Moreover, no further evidence for insecticidal activity of the peptide alone has been reported, with other disclosures covering $\omega$-ACTX-Hv1a only stating activity by injection into invertebrate pest animals.

The inventors decided to investigate further whether the $\omega$-ACTX-Hv1a toxin can be used as a pesticide against invertebrate pests. However, the inventors thought it unlikely that $\omega$-ACTX-Hv1a toxin would be rapidly absorbed through the cuticle or other external surface of invertebrate animals. Moreover, the toxin is likely to be prone to degradation in the environment. Hence, the inventors considered that on their own spider toxins such as $\omega$-ACTX-Hv1a toxin are unlikely to be useful as pesticides.

With this in mind the inventors decided to study how they could increase the effectiveness of the toxin. It can be appreciated that one likely route of a toxin to a pest is following ingestion of the toxin when formulated within a component of its diet. However, the $\omega$-ACTX-Hv1a toxin has little toxicity when held in the invertebrate gut. The inventors therefore decided to investigate whether the $\omega$-ACTX-Hv1a toxin could have greater pesticide activity if it were translocated from the gut to the circulatory system of the invertebrate pests.

As can be seen herein, the inventors fused the $\omega$-ACTX-Hv1a peptide toxin to a "carrier" peptide that can mediate translocation of the fusion protein from the invertebrate gut. The inventors used the plant lectin GNA as an example of such a carrier peptide. GNA has previously been shown to cross the gut epithelium and can be used to deliver 'passenger' peptides from the gut to the circulatory system of the invertebrate animals.

Accordingly, a fusion protein comprising a $\omega$-ACTX-Hv1a peptide toxin linked with GNA was prepared and administered to a range of invertebrate pest animals either by direct injection or when included in the animals diet. The inventors found that GNA greatly increased the biological activity, and hence that ω-ACTX-Hv1a peptide toxin can be very effective as a pesticide to invertebrate animals when supplied in this form. It is important to point out that until the present invention ω-ACTX-Hv1a toxin had not been prepared as a fusion protein linked to a protein capable of mediating translocation of the fusion protein from the invertebrate gut.

As used herein, and as further explained below, by "pesticide" the present invention relates to invertebrate pest animals, including insects, molluscs and nematodes.

The processed form of the ω-ACTX-Hv1a toxin used in the fusion protein of the first aspect of the invention comprises 37 amino acids. Further information on the ω-ACTX-Hv1a toxin may be found from GenBank; for example. Accession Number P56207 provides information regarding the amino acid sequence of the processed form of ω-ACTX-Hv1a toxin. An example of the amino acid sequence of ω-ACTX-Hv1a toxin is provided below.

```
ω-ACTX-Hv1a toxin
                                    (SEQ ID NO: 1)
SPTCIPSGQPCPYNENCCSQSCTFKENENGNTVKRCD
```

When preparing the fusion protein of the first aspect of the invention, the inventors identified that the 'KR' amino acid motif towards the C-terminus of the ω-ACTX-Hv1a toxin peptide was a potential Kex 2 signal cleavage site. Kex2 is a yeast endoprotease. Since the inventors envisaged that one means of preparing the fusion protein of the invention could be to utilise a yeast or *Pichia* expression system, they decided to prepare a modified form of ω-ACTX-Hv1a having a K34 alteration, using the amino acid numbering of SEQ ID NO:1. As can be seen from the accompanying examples, fusion protein with a K34Q ω-ACTX-Hv1a modified peptide resulted in an increase in the proportion of intact fusion protein recovered from the yeast *Pichia* host cell expression system.

Accordingly, a preferred embodiment of the invention is where the amino acid K34 of ω-ACTX-Hv1a protein is substituted. By "substituted" we mean that the Lysine amino acid residue at this position is replaced with another amino acid; preferably the Lysine is substituted for Glutamine (K34Q substitution according to the numbering of SEQ ID NO:1). The K34Q modified amino acid sequence of the K34Q modified ω-ACTX-Hv1a protein is presented below in SEQ ID NO:2

```
Modified ω-ACTX-Hv1a toxin
                                    (SEQ ID NO: 2)
SPTCIPSGQPCPYNENCCSQSCTFKENENGNTVQRCD
```

An example of a nucleic acid sequence encoding the modified ω-ACTX-Hv1a toxin peptide is provided below in relation to a further aspect of the invention.

By "fragment or variant" of ω-ACTX-Hv1a we include that the fusion protein of the first aspect of the invention can comprise an amino acid sequence of ω-ACTX-Hv1a that can vary from the sequence provided in SEQ ID NO:1 or 2 with the proviso that the fragment or variant substantially retain the biological activity of the ω-ACTX-Hv1a toxin.

By "variants" of a polypeptide we include insertions, deletions and substitutions, either conservative or non-conservative. This also includes where the peptide sequence omits several amino acids; preferably less than 5, 4, or 3 amino acids are deleted from the sequence provided in SEQ ID NO:1 or 2. In particular we include variants of the polypeptide where such changes do not substantially alter the ω-ACTX-Hv1a toxin activity. A skilled person would know that the sequence of SEQ ID NO:1 or 2 can be altered without the loss of biological activity. In particular, single like for like changes with respect to the physio-chemical properties of the respective amino acid should not disturb the functionality, and moreover small deletions within non-functional regions of the toxin peptide can also be tolerated and hence are considered "variants" for the purpose of the present invention. The experimental procedures described herein can be readily adopted by the skilled person to determine whether a 'variant' can still function as a toxin.

By "conservative substitutions" is intended combinations such as Gly, Ala; Val, Ile, Leu; Asp, Glu; Asn, Gln; Ser, Thr; Lys, Arg; and Phe, Tyr.

It is particularly preferred if the variant has an amino acid sequence which has at least 75%, yet still more preferably at least 80%, in further preference at least 85%, in still further preference at least 90% and most preferably at least 95% or 97% identity with the amino acid sequence of the ω-ACTX-Hv1a toxin provided herein.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

There are also naturally occurring homologues to the ω-ACTX-Hv1a peptide toxin which can also be used in the first aspect of the invention. Such homologues are considered to be "variants" as defined above.

*Hadroncyhe versuta* also produces the toxins ω-hexatoxin-Hv1e, ω-hexatoxin-Hv1c, ω-hexatoxin-Hv1d, and ω-hexatoxin-Hv1b which each have a very high level of sequence identity (only a few amino acid substitutions or deletions). The Sydney funnel-web spider (*Atrax robustus*) produces the peptide toxin ω-hexatoxin-Ar1d which has an identical amino acid sequence to ω-ACTX-Hv1a, and ω-hexatoxin-Ar1h and ω-hexatoxin-Ar1f which have a very high level of sequence identity (only a few amino acid substitutions or deletions).

Further peptide toxins are produced by the Toowoomba funnel-web spider, *Hadronyche infensa* (ω-hexatoxin-Hi1b_10, _8, _5, _2, _1 series; ω-hexatoxin-Hi1d; ω-hexatoxin-Hi1e; ω-hexatoxin-Hi1f) and the Tasmanian funnel-web spider, *Hadronyche venenata* (ω-hexatoxin-Hvn1b 6, 4, 3, 2, 1 series) and the Northern tree-dwelling funnel-web spider *Hadronyche formidabilis* (ω-hexatoxin-Hf1a). The peptide toxins listed above have only a few amino acid substitutions or deletions to the amino acid sequence for the ACTX-Hv1a peptide toxin of SEQ ID NO:1 or 2. Therefore each of these peptides toxins are considered to be homologous peptides to the ω-ACTX-Hv1a peptide toxin of SEQ ID NO:1 or 2 and hence can be used in the fusion peptide of the first aspect of the invention, and are embodiments of that aspect of the invention.

Further information concerning homologous peptide toxins may be found in the GenBank database. The ArachnoServer database is also very helpful (www.arachnoserver.org) as it includes information regarding a large number of spider toxins, arranged by toxin type and species. From the information provided in the databases above and by using the well-known BLAST search, the skilled person can readily identify additional peptide toxins that can be used.

However preferably the peptide toxin to be used in the fusion peptide of the first aspect of the invention comprises the amino acid sequence of SEQ ID NO:1 or 2; more preferably the peptide toxin consists of that sequence.

Preferably the first and second portions of the fusion protein are linked together by genetic or biochemical means and so, in the first instance, by at least one linking peptide or, in the second instance, by a covalent or non-covalent bond or bonds or other linking moiety. Where a peptide is used to link said members together the number of amino acid residues in the peptide is variable, and is determined by the distance between the relevant ends of each member necessary to allow said fusion protein to be in a biologically active conformation. The portions of the fusion peptide may be reversibly linked by means adapted to dissociate and release the toxic agent in situ in an invertebrate gut, for example on being metabolised by an insect or may be irreversibly linked, depending on the form of the toxic agent.

The fusion protein of the first aspect of the invention comprises as a second portion a protein capable of mediating translocation of the fusion protein from the invertebrate gut.

The inventors have previously shown that certain plant lectins are resistant to gut proteolysis and have the potential to act as carriers to deliver other peptides from the gut to the circulatory system of target species. Building from this finding, the inventors have previously utilised plant lectins as a portion of a fusion protein that can mediate translocation of the fusion protein from the invertebrate gut.

Hence the second portion of the fusion protein aids passage of the toxic member through the invertebrate gut this allowing the protein to move to a site of toxicity in the invertebrate animal. The second portion can be considered as a translocating moiety that is capable of acting as a carrier to translocate the first portion across the gut wall of invertebrate animal. Thus, the fusion protein can be used as a pesticide by delivering a toxin to a site of toxicity in an invertebrate pest animal.

Suitable proteins capable of mediating translocation of the fusion protein from the invertebrate gut include plant lectins. Suitable plant lectins for use in the fusion peptide include any one or more of the following plant lectins: snowdrop lectin *Galanthus nivalis* agglutinin (GNA), garlic lectin *Allium sativum*, pea lectin *Pisum sativum* (P-lec), peanut lectin *Arachis hypogaea*, french bean lectin (PHA, Phytohaemagglutinin). Generally any lectin that binds to insect gut can be used.

However, a preferred embodiment of the first aspect of the invention is wherein the protein capable of mediating translocation of the fusion protein from the invertebrate gut is a plant lectin selected from any one or more of the following: snowdrop lectin (GNA), garlic lectin *Allium sativum*, pea lectin *Pisum sativum* (P-lec), peanut lectin *Arachis hypogaea*, french bean lectin (PHA, Phytohaemagglutinin), or a fragment or variant thereof.

By "fragment or variant" of the plant lectin we include that the amino acid sequence of the particular lectin protein can differ from that known in the art and that naturally occurring, with the proviso that the fragment or variant substantially retain the biological activity of the lectin, i.e. be capable of mediating translocation of the fusion protein from the invertebrate gut.

Preferably the lectin is GNA. The inventors have shown in the accompanying examples that GNA can mediate the translocation of the fusion protein from the invertebrate gut to the site of toxicity in the animal. Hence a fusion protein of the first aspect of the invention comprising a ω-ACTX-Hv1a protein toxin, or a fragment, variant or derivative thereof, operably linked to GNA can be used as a pesticide against invertebrate pest animals. An example of the amino acid sequence of GNA (amino acid residues 1-105 of the mature polypeptide; from sequence data base entry M55556) is provided below.

GNA lectin (SEQ ID NO: 3)
DNILYSGETLSTGEFLNYGSFVFIMQEDCNLVLYDVDKPIWATNTGGLS

RSCFLSMQTDGNLVVYNPSNKPIWASNTGGQNGNYVCILQKDRNVVIYG

TDRWATG

An embodiment of the first aspect of the invention is wherein the protein further comprises affinity tag to aid purification.

The use of short amino acid tag sequences to aid the affinity purification of recombinant proteins is well known in the art. Indeed, many commercially available protein expression constructs include nucleic acid sequences encoding such tags. The protein of interest is inserted in to the expression construct in such a manner that the affinity tag is linked to said protein. A variety of different affinity tags are known in the art, including chitin binding protein (CBP), maltose binding protein (MBP), glutathione-S-transferase (GST), and the His-tag.

A polyhistidine-tag is an amino acid motif in proteins that consists of at least five histidine (His) residues, often at the N- or C-terminus of the protein. It is also known as hexa histidine-tag, 6×His-tag, and by the trademarked name His-Tag®. They are a well known affinity tag and methods of introducing His-tags to recombinant proteins are known in art, as are routine methods of purifying proteins with His-tags. A preferred embodiment of the invention is wherein the affinity tag is a His-tag.

The first aspect of the invention is a fusion protein comprising a first portion corresponding to a ω-ACTX-Hv1a protein toxin, or a fragment or derivative thereof, operably linked to a second portion corresponding to a protein capable of mediating translocation of the fusion protein from the invertebrate gut.

It can be appreciated by the skilled person that the fusion protein of the invention can be prepared such that the second portion, which is preferably a GNA peptide is located at the N-terminus of the ω-ACTX-Hv1a protein toxin. Hence such a fusion peptide has the arrangement: NH$_2$-(GNA: ω-ACTX-Hv1a)-COOH. Indeed, the inventors have prepared several such fusion peptides and they are specific embodiments of the invention.

NH$_2$-(GNA: ω-ACTX-Hv1a)-COOH (SEQ ID NO: 4)
DNILYSGETLSTGEFLNYGSFVFIMQEDCNLVLYDVDKPIWATNTGGLSR

SCFLSMQTDGNLVVYNPSNKPIWASNTGGQNGNYVCILQKDRNVVIYGTD

RWATGAAASPTCIPSGQPCPYNENCCSQSCTFKENENGNTVKRCDVDHHH

HHH.

The peptide of SEQ ID NO:4 has a six amino acid HIS tag placed at the C-terminus. The HIS tag can be used to aid recovery of the fusion peptide when prepared as part of a recombinant protein expression system. However, the presence of the HIS tag is optional and therefore a variant of SEQ ID NO:4 can include that peptide sequence without the HIS tag.

NH₂-(GNA: MODIFIED ω-ACTX-Hv1a)-COOH
(SEQ ID NO: 5)
HHHHHHDNILYSGETLSTGEFLNYGSFVFIMQEDCNLVLYDVDKPIWATN

TGGLSRSCFLSMQTDGNLVVYNPSNKPIWASNTGGQNGNYVCILQKDRNV

VIYGTDRWATGAAASPTCIPSGQPCPYNENCCSQSCTFKENENGNTVQRC

D

In this embodiment the HIS tag placed at the N-terminus. Similar to SEQ ID NO:4, the HIS tag is optional and therefore a variant of SEQ ID NO:5 can include that peptide sequence without the HIS tag.

Also, SEQ ID NO:5 includes the modified amino acid sequence of ω-ACTX-Hv1a, i.e. having a K34Q substitution as discussed above and as provided in SEQ ID NO:2. As mentioned above, fusion protein with a K34Q ω-ACTX-Hv1a modified peptide resulted in an increase in the proportion of intact fusion protein recovered from the yeast *Pichia* host cell expression system.

When preparing the fusion protein of the invention, the inventors decided to investigate whether the arrangement of the first and second portions in the fusion protein of the invention affected the pesticide activity of the protein.

They have surprising found that for some pests, notably *Mamestra brassicae* and *Leptinotarsa decemlineata* larvae, the location of ω-ACTX-Hv1a at the N-terminus relative to GNA provided an unexpected benefit: fusion proteins having this arrangement have a much greater pesticide effect. The order of a toxin relative to the lectin in a fusion protein pesticide has not previously been identified as having significance to pesticide activity. Hence this arrangement is a preferred embodiment of the invention and has a clear and surprising advantage.

Therefore a preferred embodiment of the invention is wherein the GNA peptide is located at the C-terminus of the ω-ACTX-Hv1a protein toxin. Such a fusion peptide has the arrangement: NH₂-(ω-ACTX-Hv1a:GNA)-COOH.

Again, the inventors have prepared several such fusion peptides and they are specific embodiments of the invention.

NH₂-(ω-ACTX-Hv1a: GNA)-COOH
(SEQ ID NO: 6)
ASPTCIPSGQPCPYNENCCSQSCTFKENENGNTVKRCDAAADNILYSGET

LSTGEFLNYGSFVFIMQEDCNLVLYDVDKPIWATNTGGLSRSCFLSMQTD

GNLVVYNPSNKPIWASNTGGQNGNYVCILQKDRNWIYGTDRWATG.

NH₂-(ω-ACTX-Hv1a: GNA: HIS)-COOH
(SEQ ID NO: 7)
ASPTCIPSGQPCPYNENCCSQSCTFKENENGNTVKRCDAAADNILYSGETL

STGEFLNYGSFVFIMQEDCNLVLYDVDKPIWATNTGGLSRSCFLSMQTDGN

LVVYNPSNKPIWASNTGGQNGNYVCILQKDRNVVIYGTDRWATGVDHHHHH

H.

In this embodiment the HIS tag placed at the C-terminus. Similar to SEQ ID NO:4, the HIS tag is optional.

NH₂-(MODIFIED ω-ACTX-Hv1a: GNA)-COOH
(SEQ ID NO: 8)
ASPTCIPSGQPCPYNENCCSQSCTFKENENGNTVQRCDAAADNILYSGETL

STGEFLNYGSFVFIMQEDCNLVLYDVDKPIWATNTGGLSRSCFLSMQTDGN

LVVYNPSNKPIWASNTGGQNGNYVCILQKDRNVVIYGTDRWATG.

Also, SEQ ID NO:8 includes the modified amino acid sequence of ω-ACTX-Hv1a, i.e. having a K34Q substitution as discussed above and as provided in SEQ ID NO:2. As mentioned above, fusion protein with a K34Q ω-ACTX-Hv1a modified peptide resulted in an increase in the proportion of intact fusion protein recovered from the yeast *Pichia* host cell expression system.

NH₂-(MODIFIED ω-ACTX-Hv1a: GNA: HIS)-COOH
(SEQ ID NO: 9)
ASPTCIPSGQPCPYNENCCSQSCTFKENENGNTVQRCDAAADNILYSGETL

STGEFLNYGSFVFIMQEDCNLVLYDVDKPIWATNTGGLSRSCFLSMQTDGN

LVVYNPSNKPIWASNTGGQNGNYVCILQKDRNVVIYGTDRWATGHHHHHH.

In this embodiment the HIS tag placed at the C-terminus.

The MODIFIED ω-ACTX-Hv1a:GNA:HIS fusion peptide presented in SEQ ID NO:9 is a particularly preferred embodiment of the invention. In this peptide, the ω-ACTX-Hv1a peptide is modified with the K34Q substitution as discussed above, and hence more intact fusion protein can be recovered from the yeast *Pichia* host cell expression system. In addition, the fusion peptide of SEQ ID NO:9 includes a HIS tag, so aiding recovery of the fusion peptide from the expression system. Moreover, the location of ω-ACTX-Hv1a at the N-terminus relative to GNA provides the benefit outlined above of a greater pesticide effect.

In preparing the MODIFIED ω-ACTX-Hv1a:GNA:HIS fusion peptide of the first aspect of the invention, the inventors decided to also include a signal peptide in the fusion peptide. That signal peptide can direct secretion of the fusion peptide from a yeast cell, so as to aid recovery of the fusion protein when expressed in a yeast expression system.

Though a number of different signal peptides are known, the inventors decided to use the α-factor signal sequence, a commonly used yeast secretion peptide.

Therefore, a specific and preferred embodiment of the invention is where the MODIFIED ω-ACTX-Hv1a:GNA: HIS fusion peptide (e.g. as shown on SEQ ID NO: 9) further comprises an N-terminal α-factor signal sequence. An example of such a peptide is shown below:

A α signal peptide fused to NH₂-
(MODIFIED ω-ACTX-Hv1a: GNA: HIS)-COOH
(SEQ ID NO: 10)
MRFPSFLLLVLFAASSALAAPVNTTTEDETAQIPAEAVIGYSDLEGDFDVA

VLPFSNSTNNGLLFINTTIASIAAKEEGVSLEKREAEAAASPTCIPSGQPC

PYNENCCSQSCTFKENENGNTVQRCDAAADNILYSGETLSTGEFLNYGSFV

FIMQEDCNLVLYDVDKPIWATNTGGLSRSCFLSMQTDGNLVVYNPSNKPIW

AGSNTGGQNNYVCILQKDRNVVIYGTDRWATGVDHHHHHHSR

The fusion protein of the first aspect of the invention may be presented as a substantially purified preparation. By "purified" is meant that the fusion protein has been at least partially separated from other components in the presence of which it has been formed, for example other components of a recombinant cell. Examples of methods of purification than may be used are described herein.

The preparation may be substantially pure. By "substantially pure" we mean that the said fusion protein is substantially free of other proteins. Thus, we include any composition that includes at least 30% of the protein content by weight as the said fusion protein, preferably at least 50%, more preferably at least 70%, still more preferably at least 90% and most preferably at least 95% of the protein content is the said fusion protein.

Thus, the invention also includes compositions comprising the said fusion protein and a contaminant wherein the contaminant comprises less than 70% of the composition by weight, preferably less than 50% of the composition, more preferably less than 30% of the composition, still more preferably less than 10% of the composition and most preferably less than 5% of the composition by weight.

The invention also includes the substantially pure said fusion protein when combined with other components ex vivo, said other components not being all of the components found in the cell in which said polypeptides are found.

As discussed above, the inventors have determined that the fusion peptide of the first aspect of the invention can be used as a pesticide.

A pesticide may be a chemical substance, biological agent (such as a virus or bacterium), antimicrobial, disinfectant or device used against any pest. Pests include insects, plant pathogens, weeds, molluscs, birds, mammals, fish, nematodes (roundworms), and microbes that destroy property, spread disease or are a vector for disease or cause a nuisance.

However, for the present invention by "pesticide" we mean that the pest is any invertebrate animal that destroys property, particularly agricultural commodities.

More preferably still the fusion protein is capable of destroying, or at least debilitating, insect pests from the following orders: Coleopterans eg. Southern corn rootworm (*Diabrotica undecimpunctata*); cowpea bruchid (*Callosobruchus maculatus*); Lepidopterans eg. European cornborer (*Ostinia nubilalis*); tobacco hornworm (*Manduca sexta*); stem borer (*Chilo partellus*): Homopteran pests e.g. Rice brown plant hopper (*Nilaparvata lugens*); rice green leaf hopper (*Nephotettix cinciteps*); potato leaf hopper (*Empoasca fabae*); peach potato aphid (*Myzus persicae*); pea aphid (*Acyrthosiphon pisum*); Dipteran eg. gout fly *Chlorop pumilionis*; Orthoptera eg. crickets and locusts; Isoptera eg. termites; Thysanoptera eg. *thrips*; Hymenoptera eg ants and arthropod pests of the order Acarina (mites).

Particularly preferred pests include the Lepidopteran *Mamestra brassicae*, Colorado potato beetle (*Leptinotarsa decemlineata*, a Coleopteran), Wheat bulb fly (*Delia coarctata*, an Anthomyiidae) and the cereal aphid *Sitobion avenae*, a Homopteran.

The inventors have also investigated whether the fusion protein of the first aspect of the invention have pesticidal activity against molluscs. As demonstrated in the accompanying examples, they have surprisingly found that the grey field slug (*Decoceras reticulatum*, a mollusc) is susceptible to the pesticidal activity of the fusion protein. Accordingly, the fusion protein is capable of destroying, or at least debilitating, molluscs, including slugs and snails, and particularly grey field slug.

The fusion protein of the first aspect of the invention can also have pesticidal activity against nematodes, particularly plant parasitic/pathogenic nematodes such as *Globodera* spp., root knot *Meloidogyne* spp., or cyst *Heterodera* spp.

"Pesticidal activity" of a fusion protein, as used herein, refers to the activity of the protein to kill, cause disease, inhibit growth or otherwise negatively affect all or part of a pest organism.

It can be appreciated that the fusion protein of the first aspect of the invention can be prepared using a number of different laboratory techniques.

For example the fusion peptide may be synthesised using solid-phase peptide synthesis, such as Fmoc or Boc techniques.

However it is preferred that the fusion protein of the first aspect of the invention is prepared using recombinant protein expression techniques in appropriate host cells. A discussion of such methods is provided herein.

A second aspect of the invention provides a nucleic acid sequence encoding the fusion protein according to any of the embodiments of the first aspect of the invention.

When preparing the fusion protein of the first aspect of the invention, the inventors decided optimise the codons encoding the ω-ACTX-Hv1a toxin peptide for expression in yeast cell expression systems. Presented below is such a nucleic acid sequence:

```
Nucleic acid sequence encoding modified
ω-ACTX-Hv1a toxin
                                      (SEQ ID NO: 11)
TCTCCAACTT GTATTCCATC TGGTCAACCA TGTCCATATA

ATGAAAATTG TTGTTCTCAA TCTTGTACTT TTAAAGAAAA

TGAAAATGGT AATACTGTTC AAAGATGTGA T
```

An example of a nucleic acid sequence encoding the GNA lectin peptide is presented below:

```
GNA peptide
                                      (SEQ ID NO: 12)
GACAATATTT TGTACTCCGG TGAGACTCTC TCTACAGGGG    60
AATTTCTCAA CTACGGAAGT

TTCGTTTTTA TCATGCAAGA GGACTGCAAT CTGGTCTTGT   120
ACGACGTGGA CAAGCCAATC

TGGGCAACAA ACACAGGTGG TCTCTCCCGT AGCTGCTTCC   180
TCAGCATGCA GACTGATGGG

AACCTCGTGG TGTACAACCC ATCGAACAAA CCGATTTGGG   240
CAAGCAACAC TGGAGGCCAA

AATGGGAATT ACGTGTGCAT CCTACAGAAG GATAGGAATG   300
TTGTGATCTA CGGAACTGAT CGTTGGGCCA CTGG
```

An example of a nucleic acid sequence encoding a α signal peptide fused to NH$_2$-(MODIFIED ω-ACTX-Hv1a: GNA:HIS)-COOH (as shown in SEQ ID NO:10) is provided below:

```
α signal peptide fused to NH2-
(MODIFIED ω-ACTX-Hv1a: GNA: HIS)-COOH
                                      (SEQ ID NO: 13)
ATGAGATTTCCTTCATTTTTACTGCTGGTTTTATTCGCAGCATCCTCCG

CATTAGCTGCTCCAGTCAACACTACAACAGAAGATGAAACGGCACAAAT

TCCGGCTGAAGCTGTCATCGGTTACTCAGATTTAGAAGGGGATTTCGAT

GTTGCTGTTTTGCCATTTTCCAACAGCACAAATAACGGGTTATTGTTTA

TAAATACTACTATTGCCAGCATTGCTGCTAAAGAAGAAGGGGTATCTCT

CGAGAAAAGAGAGGCTGAAGCTGCAGCATCTCCAACTTGTATTCCATCT

GGTCAACCATGTCCATATAATGAAAATTGTTGTTCTCAATCTTGTACTT

TTAAAGAAAATGAAAATGGTAATACTGTTCAAAGATGTGATGCGGCCGC

CGACAATATTTTGTACTCCGGTGAGACTCTCTCTACAGGGGAATTTCTC

AACTACGGAAGTTTCGTTTTTATCATGCAAGAGGACTGCAATCTGGTCT
```

```
                         -continued
TGTACGACGTGGACAAGCCAATCTGGGCAACAAACACAGGTGGTCTCTC

CCGTAGCTGCTTCCTCAGCATGCAGACTGATGGGAACCTCGTGGTGTAC

AACCCATCGAACAAACCGATTTGGGCAAGCAACACTGGAGGCCAAAATG

GGAATTACGTGTGCATCCTACAGAAGGATAGGAATGTTGTGATCTACGG

AACTGATCGTTGGGCCACTGGAGTGGACCATCATCATCATCATCATTGA
```

Methods of preparing nucleic acid molecules encoding recombinant fusion proteins use routine molecular biology techniques.

A variety of methods have been developed to link polynucleotides to form continuous single or double strands, especially double-stranded DNA, for example via complementary cohesive termini produced by digestion with restriction enzymes. Suitable methods are described in Sambrook et al. (2000) *Molecular Cloning, A Laboratory Manual*, Cold Spring Harbor Laboratory, Cold Spring Harbor, N.Y. Such methods can be readily used by the skilled person to prepare a nucleic acid molecule according to the second aspect of the invention. Moreover, the accompanying examples provide details as to how to prepare such a molecule, as explained in the methods section below.

A desirable way to prepare the nucleic acid molecule of this aspect of the invention is to use the polymerase chain reaction. This method may be used for introducing the DNA into a suitable vector, for example by engineering in suitable sites for digestion by restriction enzymes, or it may be used to modify the DNA in other useful ways as is known in the art. Hence nucleic acid sequence encoding fusion protein of the first aspect of the invention can be readily prepared according to the information provided herein.

A third aspect of the invention provides an expression construct comprising the nucleic acid sequence of the second aspect of the invention.

An "expression construct" is a term well known in the art. Expression constructs are basic tools for the production of recombinant proteins in biotechnology. The expression construct generally includes a plasmid that is used to introduce a specific nucleic acid sequence into a target cell, a "host cell". Once the expression construct is inside the cell, protein that is encoded by that gene is produced by the cellular-transcription and translation machinery ribosomal complexes. The plasmid also includes nucleic acid sequences required for maintenance and propagation of the vector, in some cases through integration into the host genome. The goal of an expression vector is the production of large amounts of stable messenger RNA, and therefore proteins.

Suitable expression constructs comprising nucleic acid for introduction into microorganisms and higher organisms can be chosen or constructed, containing appropriate regulatory sequences, including promoter sequences, terminator fragments, enhancer sequences, marker genes and other sequences as appropriate. For further details see, for example, Molecular Cloning: a Laboratory Manual: 2nd edition, Sambrook et al. supra.

The plasmid is frequently engineered to contain regulatory sequences that act as enhancer and promoter regions and lead to efficient transcription of the gene carried on the expression vector. Most parts of the regulatory unit are located upstream of coding sequence of the heterologous gene and are operably linked thereto. The expression cassette may also contain a downstream 3' untranslated region comprising a polyadenylation site, if expression in a eukaryotic host is envisaged. The regulatory sequences can direct constitutive or inducible expression of the heterologous coding sequence.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

An example of an expression construct according to the third aspect of the invention is disclosed in the accompanying examples. In this instance, the expression construct was located within an expression vector: i.e. a plasmid used to introduce nucleic acid to an appropriate host cell, and facilitate the expression of that nucleic acid from the transcription and translation machinery in that cell. In the example provided herein, the nucleic acid sequence encoding an embodiment of the fusion protein of the first aspect of the invention was inserted in to the yeast expression vector pGAPZαB to create MODIFIED ω-ACTX-Hv1a: GNA:HIS-pGAPZαB. The yeast expression vector pGAPZαB is commercially available from, for example, Invitrogen (www.invitrogen.com)

A fourth aspect of the invention provides a host cell comprising the nucleic acid molecule of the second aspect of the invention or the expression construct of the third aspect of the invention.

The host cell can be either prokaryotic or eukaryotic. Preferred prokaryotic host cells are typically strains of *E. coli* such as, for example the *E. coli* strains DH5 and RR1. Preferred eukaryotic host cells include yeast, insect and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. However it is preferred that the host cell is the yeast *Pichia pastoris*. *Pichia* protein expression systems as well known in the art, and hence cells for use as host cells can be readily obtained. Particularly preferred is where the cell strain is SMD1168H, which can be obtained from Invitrogen™ (www.invitrogen.com).

Transformation of appropriate cell hosts with a DNA construct is accomplished by well known methods that typically depend on the type of vector used. With regard to transformation of prokaryotic host cells, see, for example Sambrook at al supra. Transformation of yeast cells is described in Sherman et al (1986) *Methods In Yeast Genetics, A Laboratory Manual*, Cold Spring Harbor, N.Y.

Electroporation is also useful for transforming and/or transfecting cells and is well known in the art for transforming yeast cell, bacterial cells, insect cells and vertebrate cells. Methods for transformation of yeast by electroporation are disclosed in Becker & Guarente (1990) *Methods Enzymol.* 194, 182.

Successfully transformed cells, i.e. cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent at al (1985) *Biotech.* 3, 208.

Thus, in addition to the transformed host cells themselves, the present invention also contemplates a culture of those cells, preferably a monoclonal (clonally homogeneous) culture, or a culture derived from a monoclonal culture, in a nutrient medium.

A fifth aspect of the invention provides a method of preparing a fusion protein of the first aspect of the invention comprising culturing a host cell as defined in the fourth aspect of the invention under conditions suitable for expression of the fusion protein.

An embodiment of the fifth aspect of the invention is wherein the method further comprises the step of recovering the fusion protein.

The method of the fifth aspect of the invention comprises culturing the host cell described above for a sufficient time and under appropriate conditions in a culture medium so as to obtain expression of the fusion protein.

Methods of cultivating host cells and isolating recombinant proteins are well known in the art. Examples of suitable purification techniques are described in the Examples. For example, the fusion protein may comprise an affinity tag so as to aid purification using affinity reagents, as will be well known to those skilled in the art and as described in the Examples.

The recombinant polypeptide of the first aspect of the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography.

Alternatively, the polypeptide of the first aspect of the invention may not be recovered from the supernatant. In this case, the host cell is removed from the supernatant by simple centrifugation as would be appreciated by a person skilled in the art. The recovered supernatant comprising the fusion protein of the first aspect of the invention may be used directly.

The recombinant polypeptide can be readily isolated from the culture medium using standard techniques known in the art including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography.

The accompanying examples provide details of a protocol that can be used for this method of the invention. Here the host cell is the yeast *Pichia pastoris*.

Cells containing fusion protein encoding sequences were grown in a BioFlo 110 laboratory fermenter. Briefly for fermentation 3×50 ml YPG cultures were used to inoculate 3 l of sterile minimal media supplemented with PTM1. Cultivation at 30° C., 30% dissolved oxygen, pH 4.5-5.0 with continuous agitation was continued with a glycerol feed. Secreted proteins were separated from cells by centrifugation. Recombinant proteins were then purified from culture medium by hydrophobic interaction chromatography.

For fusion proteins containing histidine tags, diluted culture supernatant was loaded onto Ni-NTA (nickel affinity) columns for 3-10 hours at room temperature with cycling. After loading the columns were washed with a suitable buffer and proteins were eluted from the columns by buffer containing imidazole at 0.200 mM.

Fractions containing purified proteins (analysed by SDS-PAGE) were then dialysed against distilled water and lyophilised. Lyophilised samples were subsequently assessed for purity and fusion protein content by SDS-polyacrylamide gel electrophoresis. The concentrations of recombinant proteins were estimated by comparison with known amounts of standard proteins by SDS-PAGE.

A sixth aspect of the invention provides a pesticide composition comprising a fusion protein according to the first aspect of the invention.

Methods of preparing a fusion protein for use in the pesticide composition of this aspect of the invention as provided below.

Preferably the pesticide composition is in the form of any desired formulation such as a solution, emulsion, spray, suspension, powder, foam, paste, granule, aerosol, capsule or other finely or coarsely divided material or impregnant for natural or synthetic material.

In a preferred embodiment said pesticidal composition is in the form of a spray, suspension or the like, in admixture with suitable diluents, adjuvants, preservatives, dispersants, solvents, emulsifying agents or the like. Suitable composition components are those conventionally employed in the art, and in particular being suited to the present oral administration application. The composition may be obtained with use of any suitable solvents, preferably water, alcohol, mineral oil or the like, any suitable solid carriers such as kaolin, clay, talc, chalk, quartz, attapulgite, montmorillonite, diatomaceous earth, silica, or the like, with use of any solid carriers as supports for granules such as calcite, marble, pumice and crushed natural fibre material or the like.

Compositions for use in the invention may additionally be employed in intimate or physical admixture together with other known insecticides, growth promoting or regulating substances, herbicides, fungicides, synergistic agents and the like.

The composition is preferably suitable for physically or chemically associating with plants or their locus, and for oral uptake by pathogens.

The composition may therefore comprise a fusion protein as hereinbefore defined in an amount of between 0.001% and 99% by weight preferably between 0.5 and 98% by weight, more preferably between 1.0 and 95% by weight. As outlined in the accompanying examples, specific quantities of the fusion peptide used as a pesticide occur in a range of amounts, in the region of 0.01%, 0.05%, 0.75%, 0.1% and amounts between those ranges.

The pesticide composition of this aspect of the invention can be used against invertebrate pests, as outlined above in relation to the first aspect of the invention. In particular, the pesticide can be used against insect pests, molluscs and nematodes. Examples of such pests include Lepidopteran *Mamestra brassicae*, Colorado potato beetle (*Leptinotarsa decemlineata*, a Coleopteran), Wheat bulb fly (*Delia coarctata*, an Anthomyiidae) and the cereal aphid *Sitobion avenae*, a Homopteran; the grey field slug (*Decoceras reticulatum*, a mollusc); plant parasitic/pathogenic nematodes such as *Globodera* spp., root knot *Meloidogyne* spp., or cyst *Heterodera* spp.

A seventh aspect of the invention provides a process for the preparation of a pesticide composition of the sixth aspect of the invention which comprises admixture of an amount of a fusion protein of the first aspect of the invention with one or more suitable carriers, diluents, adjuvants, preservatives, dispersants, solvents, emulsifying agents in effective pesticidal amount.

An eighth aspect of the invention provides a method of preventing or treating a pest infection of a plant comprising applying a quantity of the fusion protein according to the first aspect of the invention or a pesticide composition according to the sixth aspect of the invention to the plant or its locus of growth; or introducing to the plant the nucleic acid sequence of the second aspect of the invention.

A ninth aspect of the invention provides a method of preventing or treating a mollusc or nematode pest infection of a plant comprising applying a quantity of a fusion protein comprising: (i) a ω-ACTX-Hv1a protein toxin, or a fragment, variant or derivative thereof, operably linked to (ii) a protein capable of mediating translocation of the fusion protein from the invertebrate gut; or a pesticide composition comprising said fusion protein to the plant or its locus of growth; or introducing to the plant a nucleic acid sequence encoding said fusion protein.

The term "locus" as used above refers to the physical location where the crop or plant is growing. For example, for agricultural crops, the locus may be a field; for vegetable crops, the locus may be a flowerbed or vegetable patch; and for ornamental plants, the locus may be a flower pot or container.

The present inventors have investigated the use of ω-ACTX-Hv1a protein as a toxin against a range of different pest species. In addition to the insecticidal activity of ω-ACTX-Hv1a they have also demonstrated that the toxin can be used against molluscs and nematodes.

Therefore the ninth aspect of the invention includes the use of a fusion protein comprising a ω-ACTX-Hv1a protein toxin, or a fragment or variant thereof, as a first portion, linked to a protein capable of mediating translocation of the fusion protein from the invertebrate gut as a second portion.

The fusion protein of the first aspect of the invention can be used in the method of the ninth aspect of the invention. Accordingly therefore the specific embodiments of the fusion peptide described in the first aspect of the invention can be used in the method of the ninth aspect of the invention.

As used in the ninth aspect of the invention, by "a ω-ACTX-Hv1a protein toxin, or a fragment, variant or derivative thereof", "a protein capable of mediating translocation of the fusion protein from the invertebrate gut" we include the definition of those terms as further described in the first aspect of the invention.

The ninth aspect of the invention is directed to the use of a fusion protein comprising a ω-ACTX-Hv1a protein as a pesticide against mollusc or nematode pest infection of a plant. A range of different mollusc pests can be controlled using the fusion protein, particularly the grey field slug (*Decoceras reticulatum*). Accordingly, the method of the ninth aspect of the invention includes where the mollusc is a slug or snail, and particularly grey field slug. Examples of nematode pests include plant parasitic/pathogenic nematodes such as *Globodera* spp., root knot *Meloidogyne* spp., or cyst *Heterodera* spp.

The fusion peptide of the first aspect of the invention, and the related aspects of the invention listed above, specifically the pesticide compositions, can be used as molluscicide.

It can be appreciated that, the molluscicide are suitably prepared and formulated so as to allow easy use by the consumer. For example, the molluscicide may be prepared as a liquid which can be sprayed on a crop, or as granules that can also be applied to crops.

It is well known in the art that molluscicide are commonly presented in the form of bait (or pellets). When presented in such a format, the user can easily apply the molluscicide to the plant or its locus of growth and so prevent or treat mollusc pest infection.

Hence a tenth aspect of the invention provides a molluscicide bait composition comprising a fusion protein according to the first aspect of the invention and/or a pesticide composition of the sixth aspect of the invention.

The pellet or bait can also include a mollusc attractant so as to encourage exposure of the pest to the molluscicide. A mollusc attractant is anything that attracts molluscs. The attractant may be a phagostimulant. Phagostimulants are conventionally used in slug and snail bait formulations to attract gastropods to ingest the molluscicide, and are typically attractants and/or food. Mixtures of phagostimulants with other suitable organic and/or inorganic carriers may also be used. Suitable phagostimulants for molluscicides include ground cereals (such as wheat flour, barley flour, rye flour and rice starch), crushed soya beans, fish meal, molasses, crushed rapeseed and the like. Mixtures of phagostimulants may also be used in the present invention. Other known attractants include beer, yeast, and extract of dead slugs. The bait composition may also comprise one or more bird repellents, such as anthraquinone.

The composition may be formulated to provide a slow or delayed release of molluscicide over time, so as to provide long-term protection against molluscs. Suitable slow-release auxiliaries which may be employed in the formulation include, for example, resins (such as urea/formaldehyde resins), soybean meal, waxes, stearates and oils (such as castor oil).

Other auxiliaries that may be used in the bait or pellet composition of the present invention include, for example, binders (such as methylcellosolve, polyvinylpyrrolidone, polyvinyl alcohol, polyacrylates, polymethacrylates, natural waxes, chemically modified waxes and synthetic waxes, sugars, starch, alginates, agar, lignosulphonates and gum arabic), humectants (such as polyalcohols, for example sugars or glycerol), preservatives, colorants and repellents for warm-blooded species.

The bait composition may also be coated to protect it from moisture degradation, and subsequent leaching of pymetrozine into the soil. Such a coating may extend the life of the bait composition, and reduce the re-application frequency needed. Suitably the bait composition does not prematurely degrade when it is applied to damp soil.

The bait composition is typically provided in the form of granules or pellets. The size of the pellets is such that they can be readily consumed by the target gastropods to ensure ingestion. Typically, the pellets are from about 1 to about 5 mm in length.

An eleventh aspect of the invention provides a transgenic plant or progeny thereof comprising a nucleic acid sequence encoding a fusion protein according to the first aspect of the invention.

A twelfth aspect of the invention provides a transgenic plant or progeny thereof comprising a fusion protein according to the first aspect of the invention.

As can be appreciated by the skilled person, as well as using the fusion protein of the first aspect of the invention in a pesticide, a transgenic plant can be prepared which includes nucleic acid sequence encoding that protein. When regulated in the correct manner, the transgenic plant will synthesise the fusion peptide. Thus the transgenic plant of this aspect of the invention will contain the fusion peptide and therefore will have pesticide activity.

A range of different plant species can be modified to include the nucleic acid sequence encoding the fusion peptide.

The skilled person would know that any monocot or dicot plant can be used. A dicot plant may be selected from the families including, but not limited to Asteraceae, Brassicaceae (eg *Brassica napus*), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae. For example, the plant may be selected from lettuce, sunflower, *Arabidopsis*, broccoli, spinach, water melon, squash, cabbage, tomato, potato, capsicum, tobacco, cotton, okra, apple, rose, strawberry, alfalfa, bean, soybean, field (fava) bean, pea, lentil, peanut, chickpea, apricots, pears, peach, grape vine or citrus species.

Also included are biofuel and bioenergy crops such as sugar cane, oilseed rape/canola, linseed, and willow, poplar, poplar hybrids, switchgrass, Miscanthus or gymnosperms, such as loblolly pine. Also included are crops for silage (eg forage maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed).

A monocot plant may, for example, be selected from the families Arecaceae, Amaryllidaceae or Poaceae. For example, the plant may be a cereal crop, such as wheat, rice, barley, maize, oat, sorghum, rye, onion, leek, millet, buckwheat, turf grass, Italian rye grass, switchgrass, Miscanthus, sugarcane or *Festuca* species.

Preferably, the plant is a crop plant. By crop plant is meant any plant which is grown on a commercial scale for human or animal consumption or use or other non-food/feed use. Preferred plants are maize, tobacco, wheat, rice, oilseed rape, sorghum, soybean, potato, tomato, barley, pea, bean, field bean, cotton, lettuce, broccoli or other vegetable brassicas.

A sequence or vector described herein encoding for the fusion protein of the first aspect of the invention is introduced as a transgene into the plant. This can be carried out by various methods as known in the field of plant genetic engineering, for example using transformation with *Agrobacterium*, particle bombardment, electroporation or viral transformation. Such techniques are well known in the art. Also, the use of specific techniques for each of the plant species listed herein are also well known. The methods of the art can be readily adopted by the skilled person to prepare a transgenic plant or progeny thereof comprising a nucleic acid sequence encoding a fusion protein according to the first aspect of the invention.

When used for preparing a transgenic plant of this aspect of the invention, the nucleic acid encoding the fusion peptide is typically placed within an "expression cassette" suitable for arranging the expression of the nucleic acid sequence in the plant.

Preferably, the nucleic acid encoding the fusion peptide will be operably linked to a further region of nucleic acid encoding the GNA signal peptide, which will be placed so that the signal peptide is present at the N-terminus of the fusion peptide. The GNA signal peptide is useful as it assists in the successful production of fusion proteins in plants. An example of an amino acid sequence of a GNA signal peptide that can be used for the fusion protein expressed by the plant of this aspect of the invention is provided below as SEQ ID NO:15 in relation to a further aspect of the invention.

The expression cassette will typically contain nucleic acid sequence which act to regulate the expression of the nucleic acid in the plant, e.g. a promoter region.

Some promoters can drive constitutive expression of the nucleic acid in the plant, including the well known 35S promoter, 19S promoter or the ubiquitin promoter.

Other promoters can be used to regulate organ or tissue specific expression of the nucleic acid sequence encoding the fusion protein. A "tissue-specific promoter" or "tissue-preferred promoter" refers to a regulated promoter that is not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of sequence. Suitable promoters include the napin-gene promoter from rapeseed, the USP-promoter from *Vicia faba*, the oleosin-promoter from *Arabidopsis*, the phaseolin-promoter from *Phaseolus vulgaris*, the Bce4-promoter from *Brassica* or the legumin B4 promoter as well as promoters conferring seed specific expression in monocot plants.

Promoters active in photosynthetic tissue in order to drive transcription in green tissues such as leaves and stems include ribulose-1,5-bisphosphate carboxylase (RbcS) promoters such as the RbcS promoter from eastern larch (*Larix laricina*), the pine cab6 promoter, the Cab-1 gene promoter from wheat, the CAB-1 promoter from spinach, the cabIR promoter from rice, the pyruvate orthophosphate dikinase (PPDK) promoter from corn, the *Arabidopsis thaliana* SUC2 sucrose-H+ symporter promoter. Nucleic acid sequences representative of such promoters can be readily identified by the skilled person from, for example, GenBank.

Promoters suitable for preferential expression in plant root tissues include, for example, the promoter derived from corn nicotianamine synthase gene and rice RCC3 promoter.

Promoters suitable for preferential expression in plant vascular tissues include, for example, rice sucrose synthase-1 gene (RSs1).

Inducible promoters include promoters which are responsive to abiotic and biotic environmental stimuli. Abiotic environmental stimuli include light, temperature and water availability. Biotic environmental stimuli include pathogens, (including viral induced, bacterial induced, fungal induced, insect induced, and nematode induced promoters), interactions with symbionts and herbivores. Promoters may also be responsive to movement, touch, tissue damage and phytohormones (including abscissic acid, cytokinins, auxins, giberellins, ethylene, brassinosteroids and peptides such as systemin and nodulation factors). Temporally regulated promoters include circadian regulated promoters as well as those which respond to non-circadian time-keeping mechanisms.

Chemically inducible promoters are especially suitable if gene expression is wanted to occur in a time specific manner. Examples of such promoters are a salicylic acid inducible promoter, a tetracycline inducible promoter, and an ethanol inducible promoter (WO 93/21334).

In order to obtain improved expression in plants, the codon usage of the nucleic acid encoding the fusion protein can be modified to form an equivalent, modified or artificial gene or gene part in accordance with techniques, so as to increase the efficiency of expression of the fusion protein in plant cells. Moreover, the nucleic acid may also be inserted in the plastid (e.g., chloroplast) or mitochondrial genome of a plant and expressed there using a suitable promoter. For obtaining enhanced expression in monocot plants such as corn or rice, an intron (e.g., a monocot intron) can also be added to the chimeric gene.

It may be preferred that chimeric nucleic acids of the invention (and suitable for use in the methods of the invention) further comprise nucleic acid sequences for the expression of products that may aid in the identification of plant cells into which the chimeric nucleic acid sequences have been successfully incorporated. Examples of suitable further nucleic acid sequences that may be used in this manner will be apparent to those skilled in the art, and include nucleic acids giving rise to products that confer resistance to substances that may be used for selection (such as antibiotics) or markers that give rise to a detectable product that may be used as the basis for selection (such as a chromogenic enzyme product).

In a further aspect the present invention provides a plant transformed with a nucleic acid according to the second aspect of the invention (and any embodiment thereof described in this specification).

In a further aspect the present invention provides a plant seed comprising a nucleic acid according to the second aspect of the invention (and any embodiment thereof described in this specification).

A thirteenth aspect of the invention provides a transgenic plant or progeny thereof comprising a fusion protein comprising: (i) a ButaIT protein toxin, or a fragment, variant or derivative thereof, operably linked to (ii) a protein capable of mediating translocation of the fusion protein from the invertebrate gut.

The present inventors have also investigated the utility of further invertebrate toxins to determine if they have utility as pesticides when introduced into plants. The ButaIT protein toxin is a toxin from the South Indian red scorpion (*Mesobuthus tamulus*). It has previously been demonstrated that ButaIT has oral toxicity to insects when prepared as a recombinant protein, and also that GNA can be used as a protein capable of mediating translocation of the fusion protein from the invertebrate gut.

The inventors therefore investigated whether ButaIT toxin when expressed as such a fusion protein in a transgenic plant would have pesticide activity. They have found that such a transgenic plant can express the fusion peptide, and moreover such peptides have pesticide activity.

The ButaIT protein toxin is known in the art. It has previously been shown that ButaIT can block invertebrate but not vertebrate calcium channels. Examples of amino acid sequences of the ButaIT protein can be readily identified by the skilled person. An example of the amino acid sequence of ButaIT is provided below:

```
ButaIT toxin
                                      (SEQ ID NO: 14)
RCGPCFTTDPQTQAKCSECCGRKGGVCKGPQCICGIQ
```

By "fragment or variant" of ButaIT we include that the fusion protein expressed by the plant of this aspect of the invention can comprise an amino acid sequence of ButaIT that can vary from the sequence provided in SEQ ID NO:14 with the proviso that the fragment or variant substantially retain the biological activity of the ButaIT toxin. A detailed explanation of the terms "fragment or variant" is provided above in relation to the first aspect of the invention and also applies to this aspect of the invention.

The fusion protein expressed by the plant of this aspect of the invention comprises as a second portion a protein capable of mediating translocation of the fusion protein from the invertebrate gut.

Examples of protein capable of mediating translocation of the fusion protein from the invertebrate gut are provide above in relation to the first aspect of the invention and also applies to this aspect of the invention.

Suitable proteins capable of mediating translocation of the fusion protein from the invertebrate gut include plant lectins. Suitable plant lectins for use in the fusion peptide include any one or more of the following plant lectins: snowdrop lectin *Galanthus nivalis* agglutinin (GNA), garlic lectin *Allium sativum*, pea lectin *Pisum sativum* (P-lec), peanut lectin *Arachis hypogaea*, french bean lectin (PHA, Phytohaemagglutinin). Generally any lectin that binds to insect gut can be used.

It is particularly preferred that the protein is a plant lectin selected from any one or more of the following: snowdrop lectin (GNA), garlic lectin *Allium sativum*, pea lectin *Pisum sativum* (P-lec), peanut lectin *Arachis hypogaea*, french bean lectin (PHA, *Phytohaemo glutinin*), or a fragment or variant thereof.

Preferably the lectin is GNA. Hence the fusion protein expressed by the plant of this aspect of the invention comprises a ButaIT protein toxin, or a fragment or derivative thereof, operably linked to GNA can be used as a pesticide against invertebrate pest animals. An example of the amino acid sequence of GNA is provided in the first aspect of the invention as SEQ ID NO:3.

It can be appreciated by the skilled person that the fusion protein expressed by the plant of this aspect of the invention can be prepared such that the second portion, which is preferably a GNA peptide is located at the N-terminus of the ButaIT protein toxin. Hence such a fusion peptide has the arrangement: NH$_2$-(GNA:ButaIT)-COOH. Indeed, the inventors have prepared several such fusion peptides and they are specific embodiments of the invention.

When preparing the fusion protein expressed by the plant of this aspect of the invention, the inventors decided to investigate whether the arrangement of the first and second portions in the fusion protein affected the pesticide activity of the protein. They have surprising found that it is preferable that the transgenic plant of this aspect of the invention expresses a fusion protein in which the GNA peptide is located at the C-terminus of the ButaIT protein toxin, since in this arrangement the fusion peptide has much greater pesticidal activity. The order of a toxin relative to the lectin in a fusion protein pesticide has not previously been identified as having significance to pesticide activity. Hence this arrangement is a preferred embodiment of the invention and has a clear and surprising advantage.

Therefore a preferred embodiment of the invention is wherein the GNA peptide is located at the C-terminus of ButaIT protein toxin. Such a fusion peptide has the arrangement: NH$_2$-(ButaIT:GNA)-COOH.

Furthermore, the inventors have also determined that it is desirable that the fusion protein expressed by the plant of this aspect of the invention comprises a GNA 'signal peptide' located at the N-terminus of the fusion peptide. The GNA signal peptide is a region of amino acids which directs the intracellular transport of the fusion protein to the vacuole of the plant cell.

An example of a GNA signal peptide that can be used for the fusion protein expressed by the plant of this aspect of the invention is provided below:

```
GNA signal peptide
                                      (SEQ ID NO: 15)
MAKASLLILAAIFLGVITPSCLS
```

Therefore a preferred embodiment of the invention is wherein fusion protein expressed by the plant of this aspect of the invention has the following arrangement: NH$_2$-(GNA signal peptide:ButaIT:GNA)-COOH.

An example of such a peptide is provided below:

```
NH₂-(GNA signal peptide: ButalT: GNA)-COOH
                                        (SEQ ID NO: 16)
MAKASLLILAAIFLGVITPSCLSAAARCGPCFTTDPQTQAKCSECCGRKG

GVCKGPQCICGIQAAADNILYSGETLSTGEFLNYGSFVFIMQEDCNLVLY

DVDKPIWATNTGGLSRSCFLSMQTDGNLVVYNPSNKPIWASNTGGQNGNY

VCILQKDRNVVIYGTDRWATG
```

Examples of nucleic acid molecules encoding the ButalT and GNA peptides are well known in the art. As way of an example, we provide below the sequence of a nucleic acid molecule encoding the fusion protein expressed by the plant of this aspect of the invention.

```
Nucleic acid sequence encoding NH₂-
(GNA signal peptide: ButalT: GNA)-COOH
                                        (SEQ ID NO: 17)
ATGGCTAAGGCAAGTCTCCTCATTTTGGCCGCCATCTTCCTTGGTGTCATC

ACACCATCTTGCCTGAGTGCTGCAGCAAGGTGTGGTCCTTGCTTTACAACT

GATCCTCAAACACAAGCCAAGTGTAGTGAGTGTTGTGGGCGAAAGGGTGGA

GTATGCAAGGGCCCACAATGTATCTGTGGTATACAAGCGGCCGCCGACAAT

ATTTTGTACTCCGGTGAGACTCTCTCTACAGGGGAATTTCTCAACTACGGA

AGTTTCGTTTTTATCATGCAAGAGGACTGCAATCTGGTCTTGTACGACGTG

GACAAGCCAATCTGGGCAACAAACACAGGTGGTCTCTCCCGTAGCTGCTTC

CTCAGCATGCAGACTGATGGGAACCTCGTGGTGTACAACCCATCGAACAAA

CCGATTTGGGCAAGCAACACTGGAGGCCAAAATGGGAATTACGTGTGCATC

CTACAGAAGGATAGGAATGTTGTGATCTACGGAACTGATCGTTGGGCTACT

GGATGA
```

Methods of preparing such nucleic acid molecules are described above in relation to further aspects of the invention, as are methods of preparing a transgenic plant of this aspect of the invention encoding such a fusion protein. For the avoidance of doubt, the information provided above as to how to prepare suitable transformation vectors and transgenic plants also apply to this particular aspect of the invention.

A further aspect of the invention provides the use of a fusion protein according to the first aspect of the invention in the manufacture of a pesticide or a transgenic plant cell or plant.

A further aspect of the invention provides the use of a pesticide according to the sixth aspect of the invention to destroy, or debilitate one or more pests.

A further aspect of the invention provides a fusion protein, composition, vector, polynucleotide, host cell, transgenic plant, or methods for the preparation or use thereof substantially as herein described in the description or sequences or illustrated in the Figures.

FIG. 1: Diagrammatic representation of constructs created for the expression of omega/GNA (FP5) fusion protein in the yeast expression vector pGAPZαB. Replacement of lysine for glutamine (Q) in omega amino acid sequence is depicted for MODomega/GNA and His/GNA/MODomega.

Figure 2:
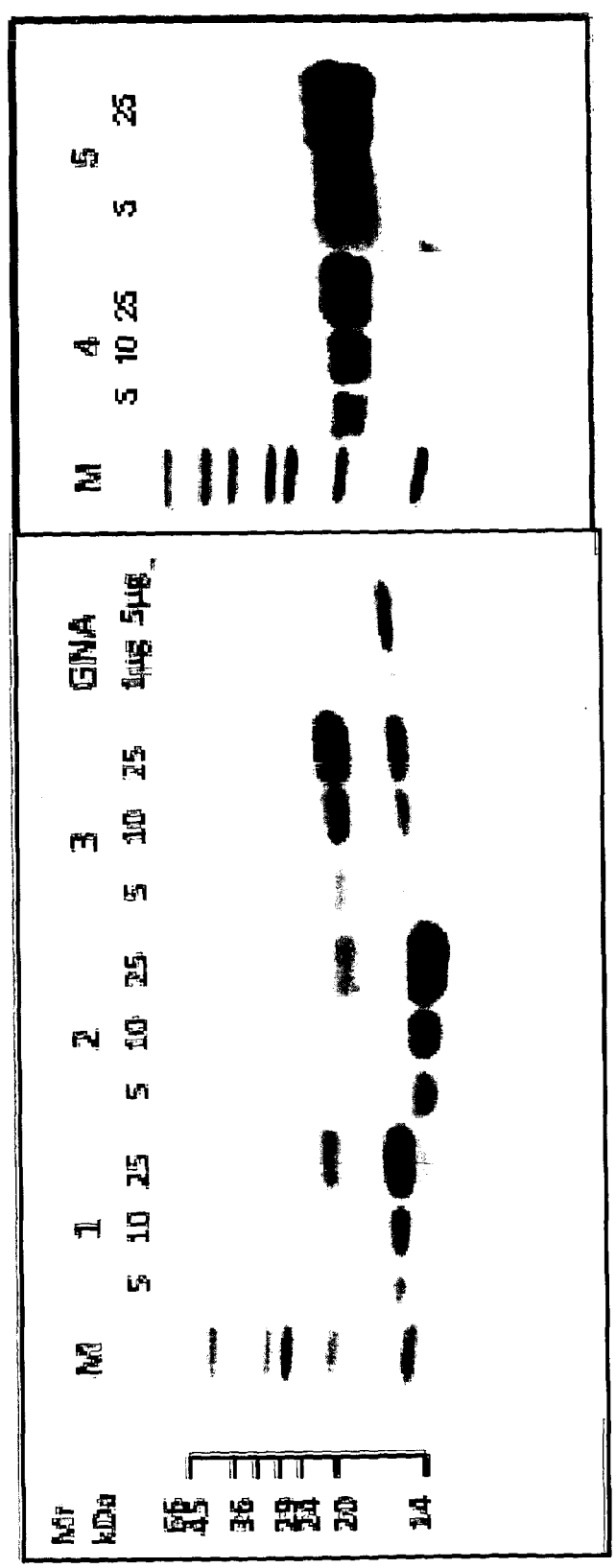

FIG. 2: SDS-PAGE (17.5% acrylamide gel) analysis of omega/GNA variants after purification and lyophilisation. Loading as follows 1 denotes omega/GNA/His; 2 omega/GNA; 3 modified MOD.omega/GNA, 4 His/GNA/omega, and 5 His/GNA/MOD.omega. Loading for each lane is given as total dry weight (μg) of lyophilised sample and loading of GNA standards is given in μg recombinant protein.

Figure 3:
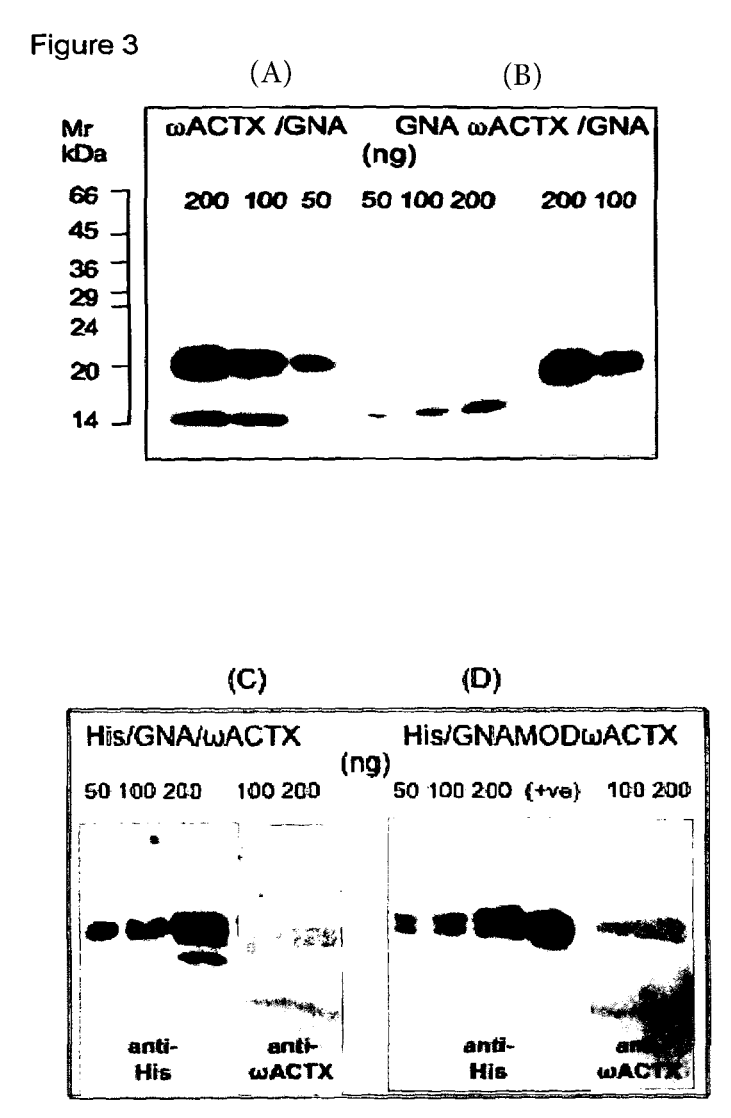

FIG. 3: Western analysis of purified recombinant omega/GNA (ωACTX/GNA) using (A) anti-GNA antibodies, and (B) anti-omega (ωACTX) antibodies (1:3300 and 1:1000 dilution, respectively). Western analysis of purified (C) recombinant His/GNA/omega (His/GNA/ωACTX) and (D) recombinant His/GNA/modified omega (His/GNA/MODωACTX) using anti-His and anti-omega (ωACTX) antibodies (1:1000 dilution). Protein loading in ng protein is depicted.

Figure 4:
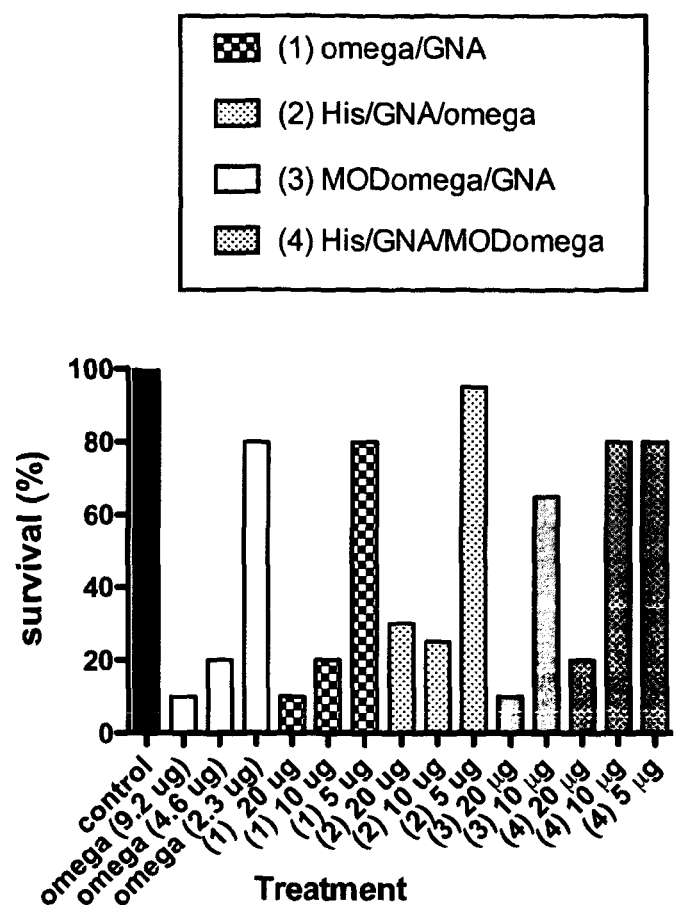

FIG. 4: Survival of cabbage moth (*M. brassicae*) larvae injected with four variants of omega/GNA fusion proteins or control (PBS) or omega peptide (ACTX) alone (n=10-20 per treatment). Doses of 20 and 10 μg of fusion protein are equivalent to doses of 4.6, and 2.3 μg of omega alone on a molar basis.

Figure 5:
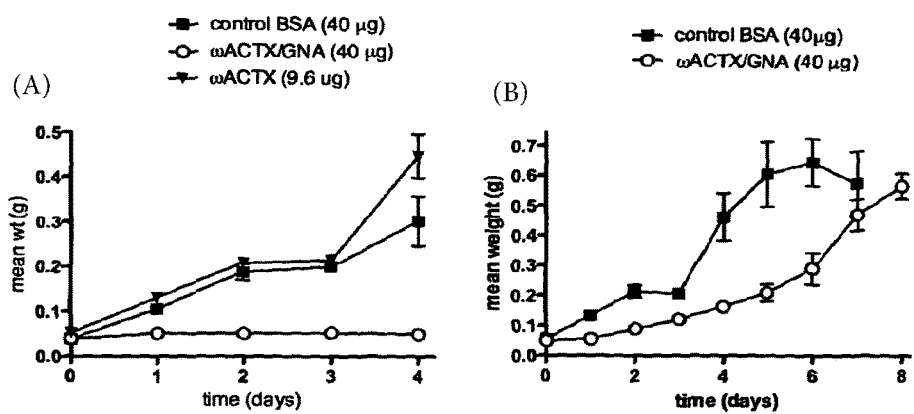

FIG. 5: (A) Mean weight of fifth instar *M. brassicae* larvae fed on a daily droplet containing omega (ωACTX) or omega/GNA (ωACTX/GNA) (n=7 per treatment). Dose of omega toxin is equivalent to the dose of omega toxin contained in 40 μg fusion protein. (B) Mean weight of fourth instar larvae fed on a single droplet containing 40 μg omega/GNA.

Figure 6:
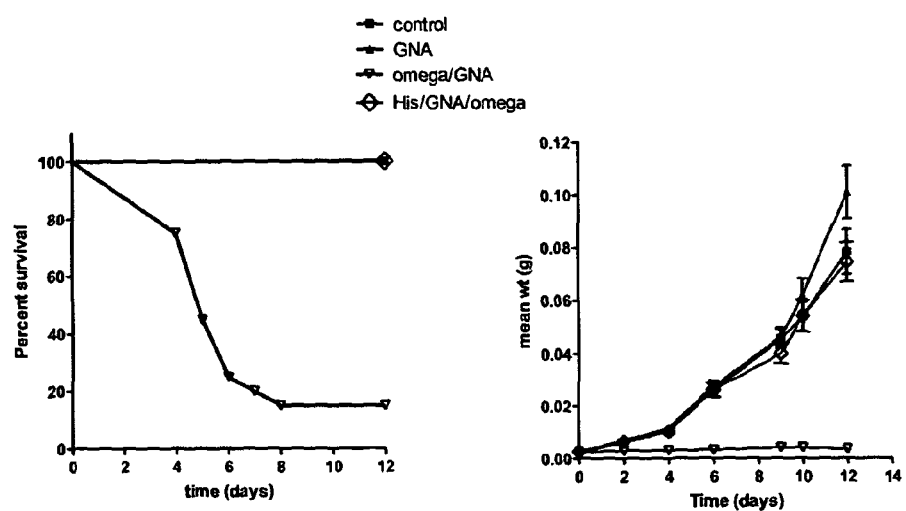

FIG. 6: Survival and mean weight of *M. brassicae* larvae fed on diets containing omega/GNA or His/GNA/omega at 2.5 mg/5 g diet (500 ppm) or GNA (5 mg/5 g; 1000 ppm) and control no added protein. N=20 per treatment.

Figure 7:
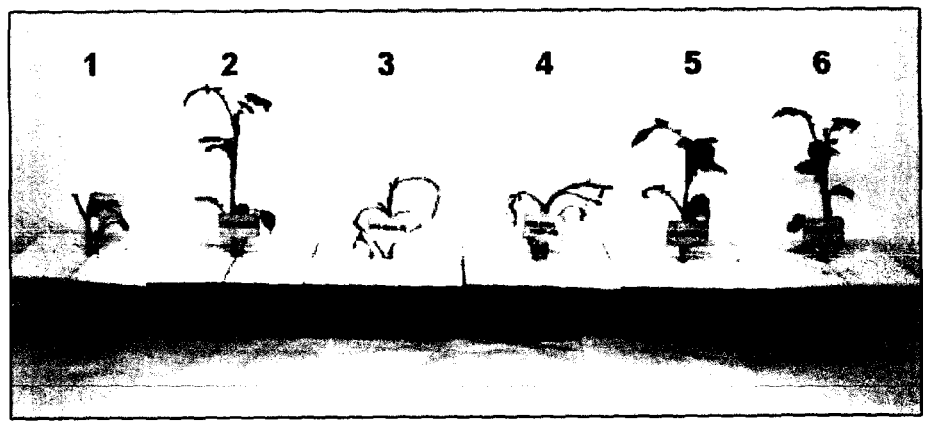

FIG. 7: Photograph of plants after exposure to Colorado potato beetle larvae as depicted in Table 2. 1 denotes control; 2 MODomega/GNA; 3 His/GNA/omega; 4 His/GNA/MODomega; 5 omega/GNA/His; 6 FP4 (RST/GNA/His).

Figure 8:
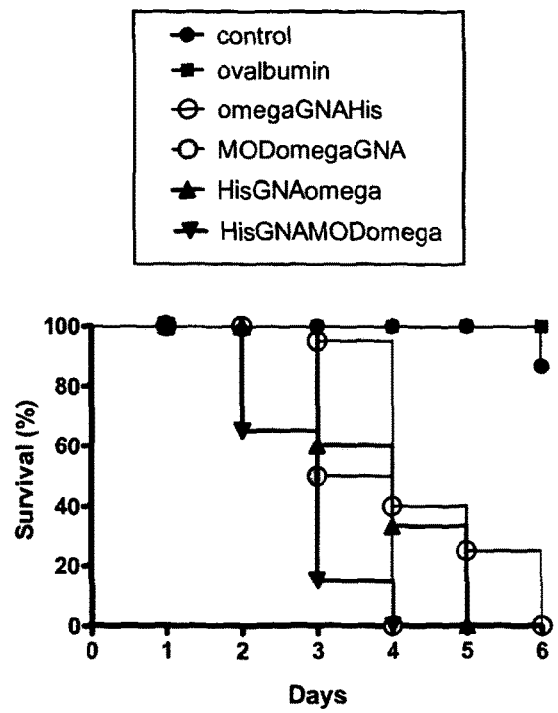

FIG. 8: Survival of cereal aphids (*Sitobion avenae*) exposed to diets (n=20 per treatment) containing FP5 variants at 0.5 mg/ml (500 ppm) for 6 days.

Figure 9:
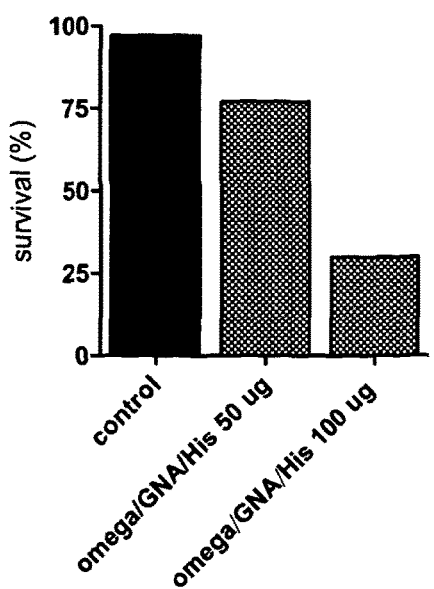

FIG. 9: Survival of adult grey field slugs (*D. reticulatum*) 7 days after injection of 50 or 100 μg omega/GNA/His equivalent to 12.5 and 25 μg omega toxin, respectively (control n=18; omega/GNA/His n=18 and 27 for 50 and 100 μg omega/GNA/His, respectively).

Figure 10:
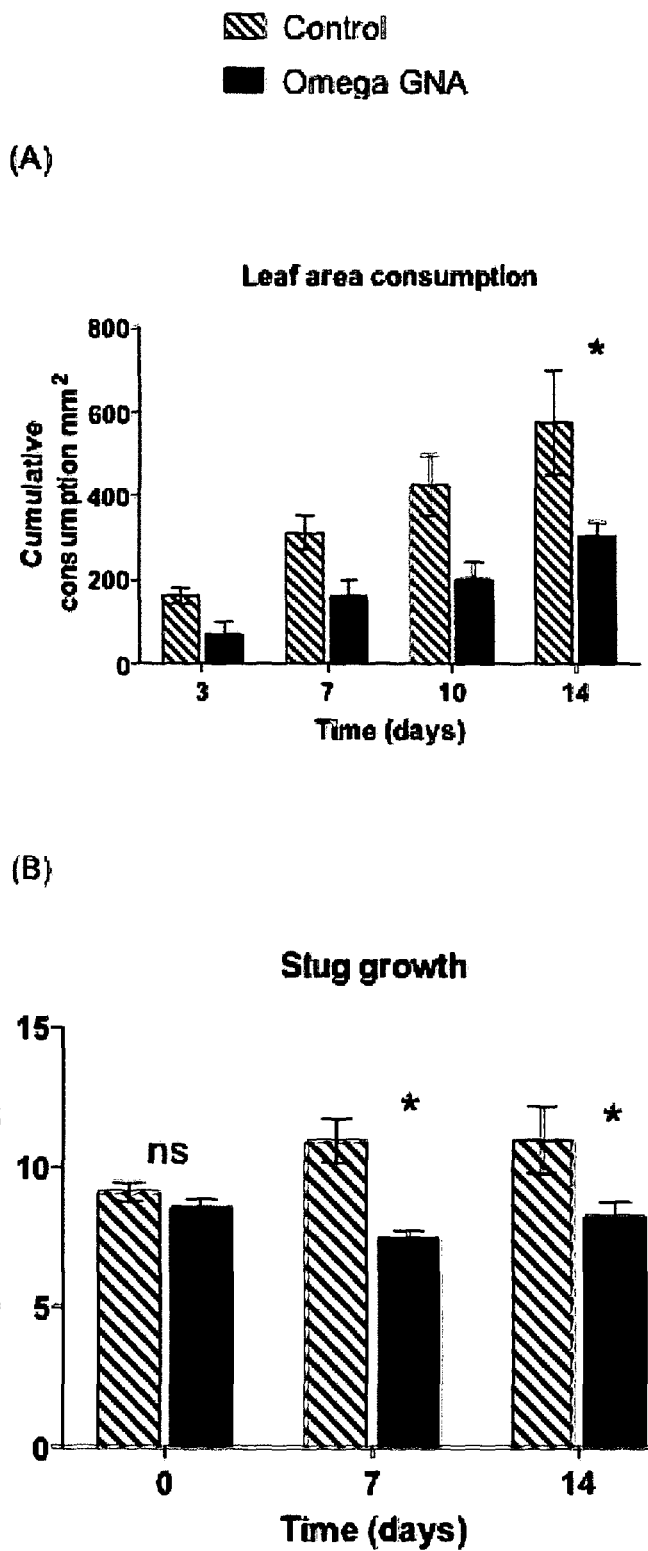

FIG. 10: (A) Cumulative consumption of leaf and (B) mean weight of juvenile slugs fed on lettuce discs coated with omega/GNA/His (1 mg/leaf disc) recorded after 7 and 14 days (n=20 per treatment).

Figure 11:
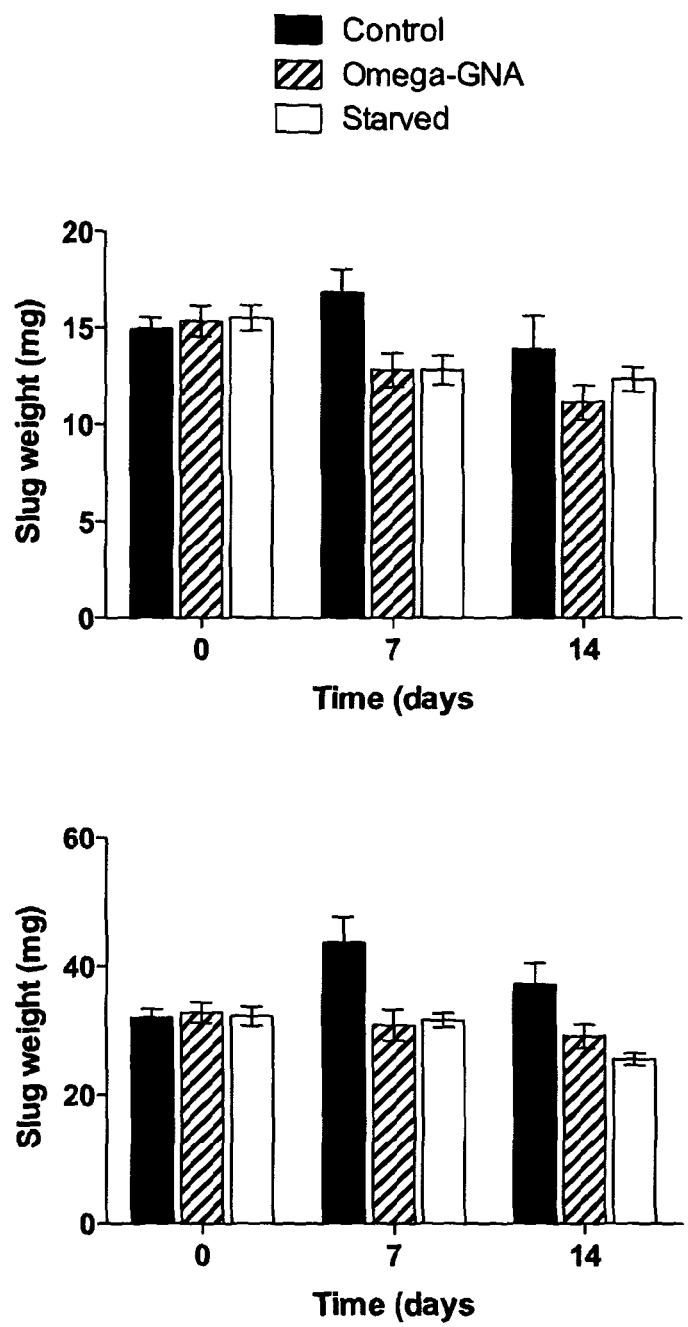

FIG. 11: Mean weight recorded for juvenile *D. reticulatum* 7 and 14 days after exposure to wheat pellets containing omega/GNA/His at 1.3% w/w. Starved slugs were analysed for weight gain as a control treatment, and slugs fed on pellets with no added protein (n=20 per treatment) provided a second control group in both bioassay A and B.

Figure 12:
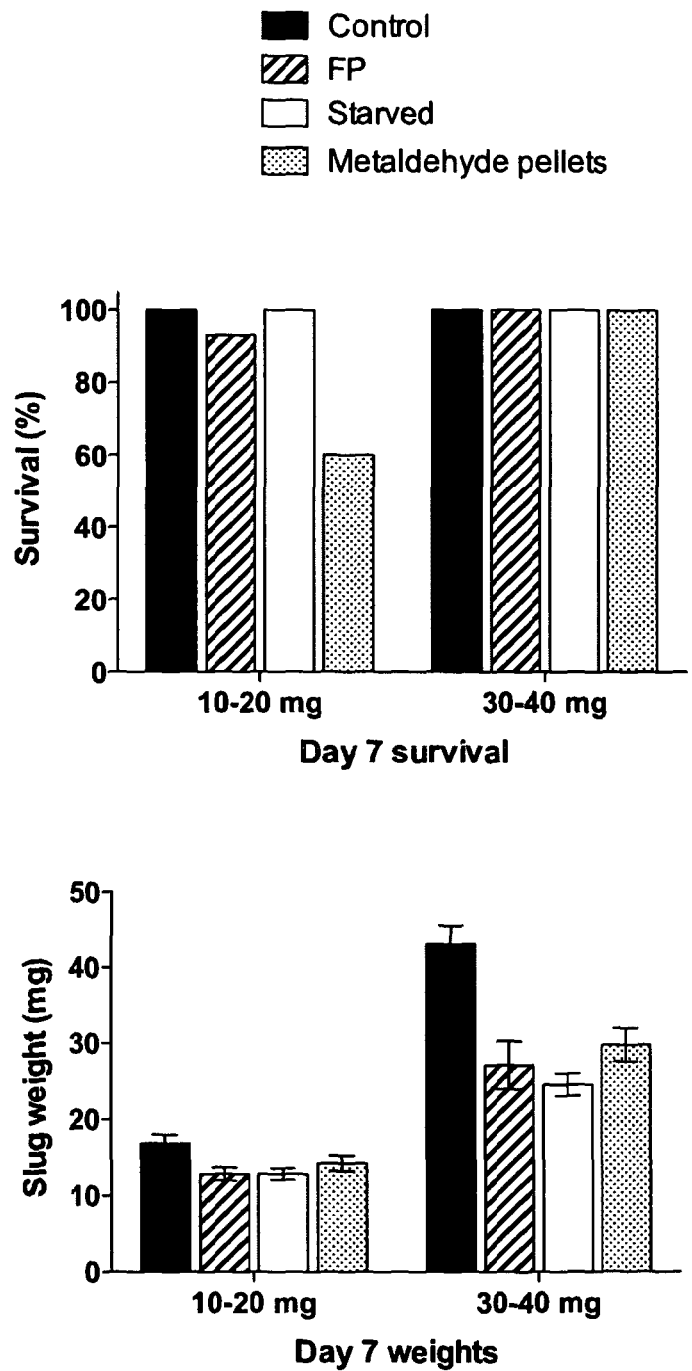

FIG. 12: (A) Survival and (B) mean weight of two groups (10-20 mg and 30-40 mg) of juvenile *D. reticulatum* fed on commercial metaldehyde containing pellets; wheat pellets containing His/GNA/omega (2.2% w/w), or control wheat pellets containing no added protein. A group of starved slugs were included as a negative control. (n=20 per treatment).

Figure 13:
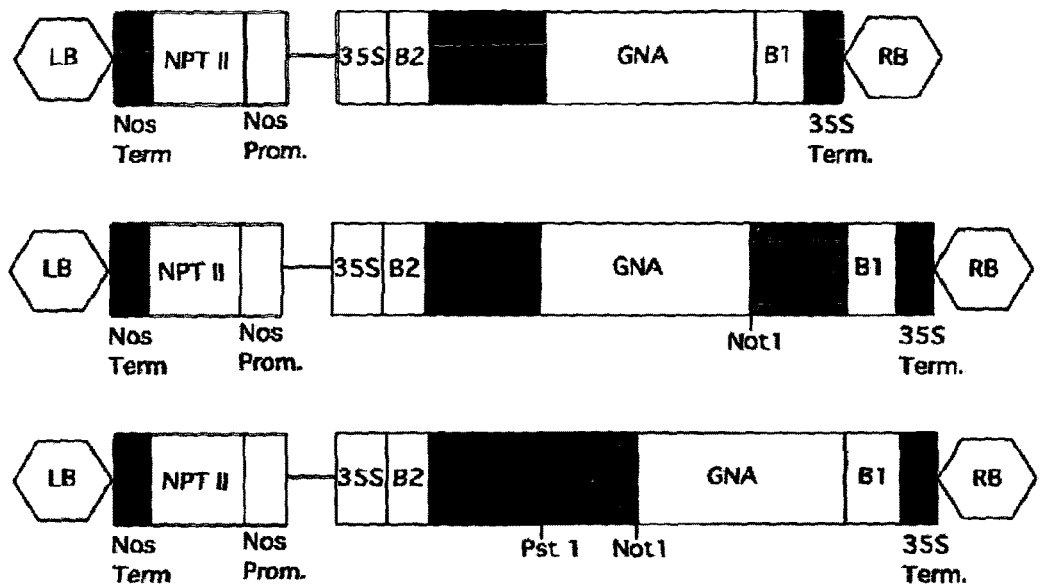
Figure 14:
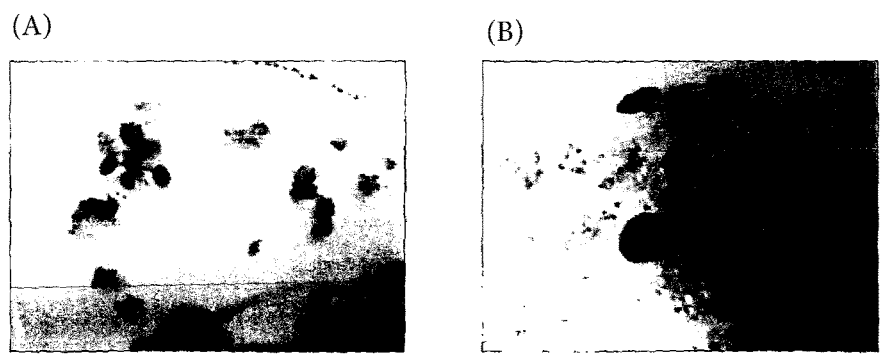

FIG. 13: Diagrammatic representation of the T-DNA region of the expression vector pK2WG7 containing the expression constructs. GNA leader (signal sequence) is shown in green, the mature GNA sequence in yellow and ButalT toxin in blue. LB, RB=left and right borders of T-DNA; Nos Prom., NPTII, Nos Term.=construct for expressing neomycin phosphotransferase, giving resistance to kanamycin (selectable marker); 35S=Cauliflower mosaic virus (CaMV) 35S RNA promoter; 35S Term.=35S gene terminator; B1, B2=Gateway recombination sites FIG. 14: Transformants ($T_0$) growing on 0.5×MS10 media plates with 50 µg/µl kanamycin. (a) Germinated seeds from plants dipped with *Agrobacterium* containing the GNA leader/GNA/ButaIT construct. (b) Germinated seeds from plants dipped with *Agrobacterium* containing the GNA leader/GNA construct.

Figure 15:
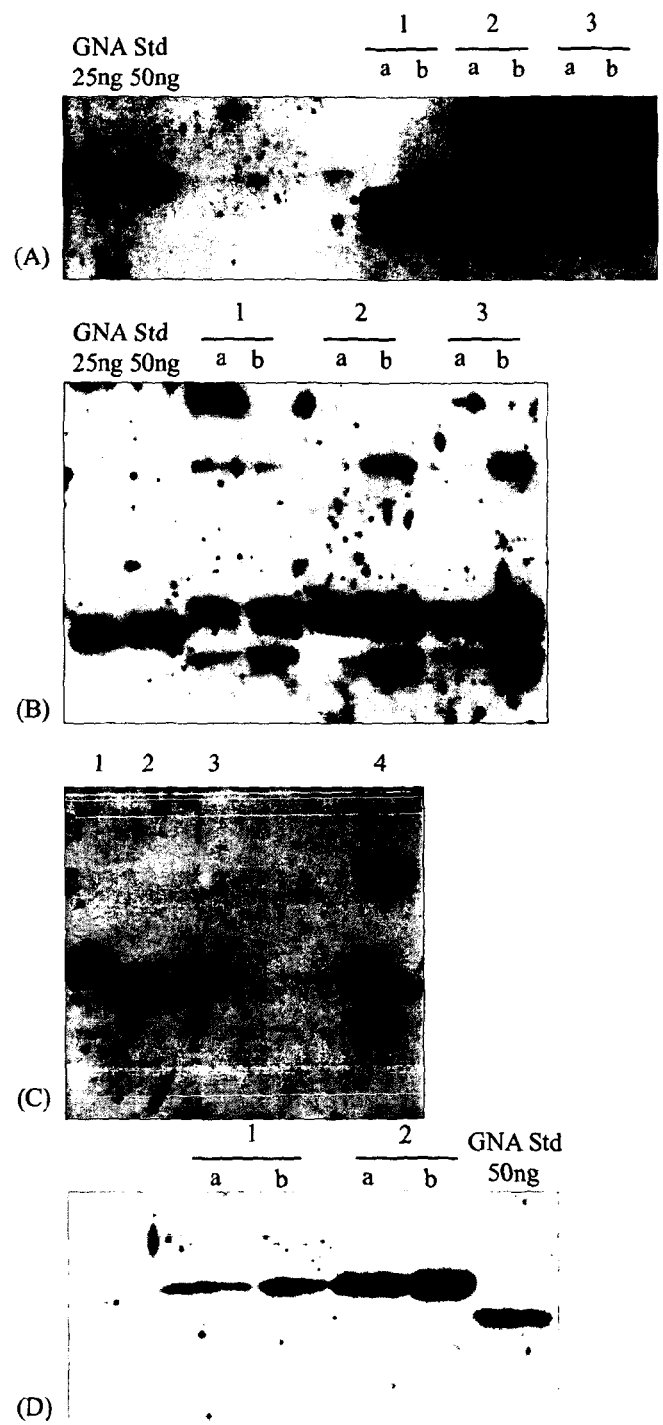

FIG. 15: Western blot analysis (probed with anti GNA antibodies) of $T_3$ stage transgenic *Arabidopsis* used in bioassays (A) GNA expression; 25 µg (a) and 50 µg (b) of three independent plants (1, 2, 3) (B) ButaIT/GNA (line 40) expression; 25 µg (a) and 50 µg (b) of three independent plants (1, 2, 3) (C) ButaIT/GNA std 50 ng (1), GNA std Song (2), GNA/ButaIT std 50 ng (3), Line 45 50 µg (4), (D) GNA/ButaIT (line 5) expression; 25 µg (a) and 50 µg (b) of two independent plants (1 and 2).

Figure 16:
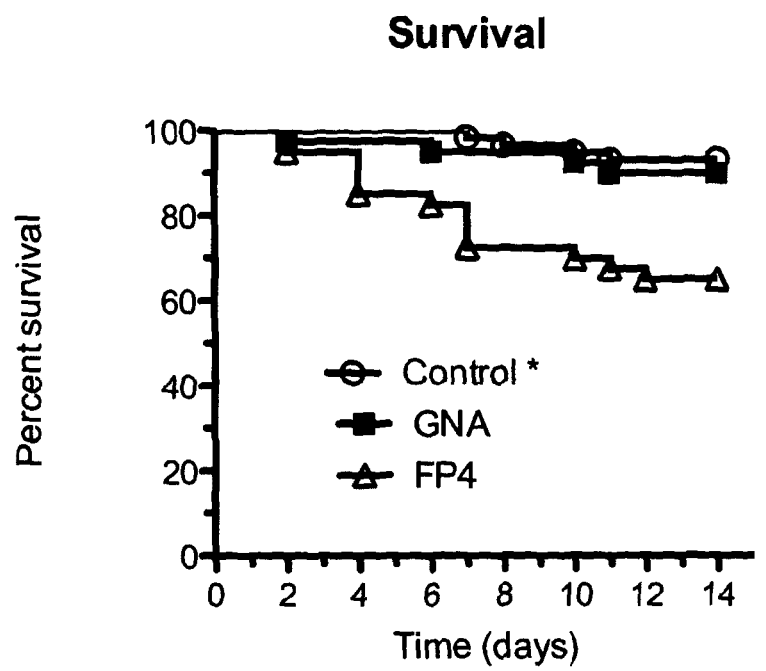
Figure 16:
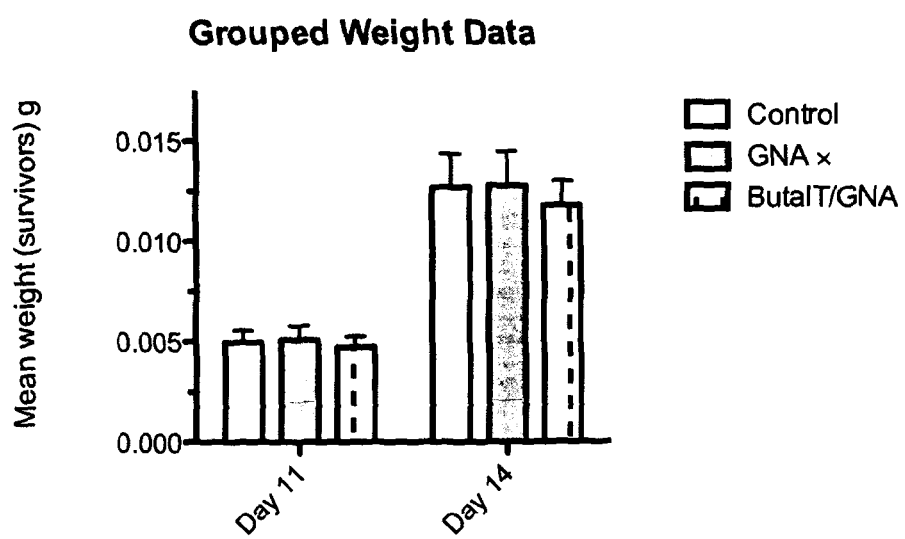

FIG. 16: (A) Kaplan-Meier survival plots of tomato moth (*Lacanobia oleracea*) larvae (n=40 per treatment, * denotes n=60) exposed to GNA (line3) and ButaIT/GNA (line 40) expressing *Arabidopsis* leaves for 14 days from hatch and (B) the mean weight (±SEM) of surviving insects (x denotes n=20)

Figure 17:
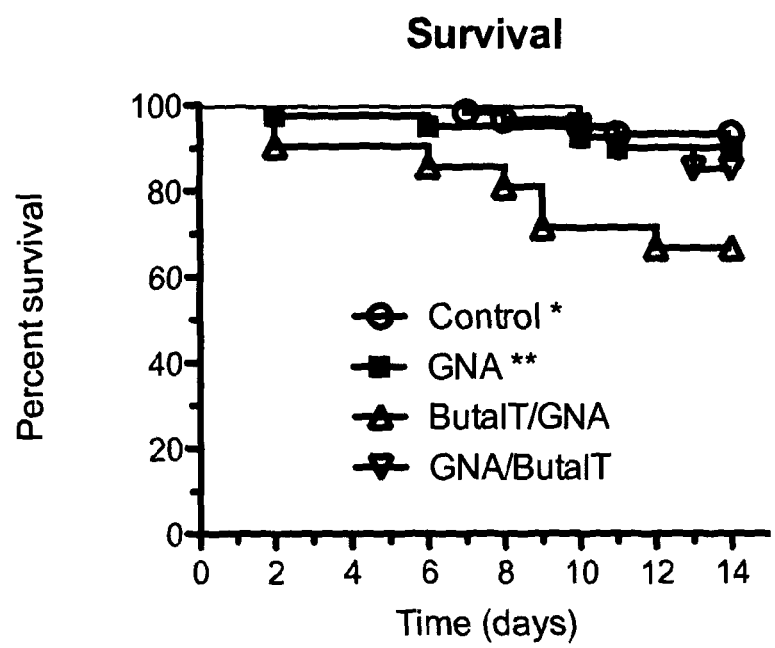
Figure 17:
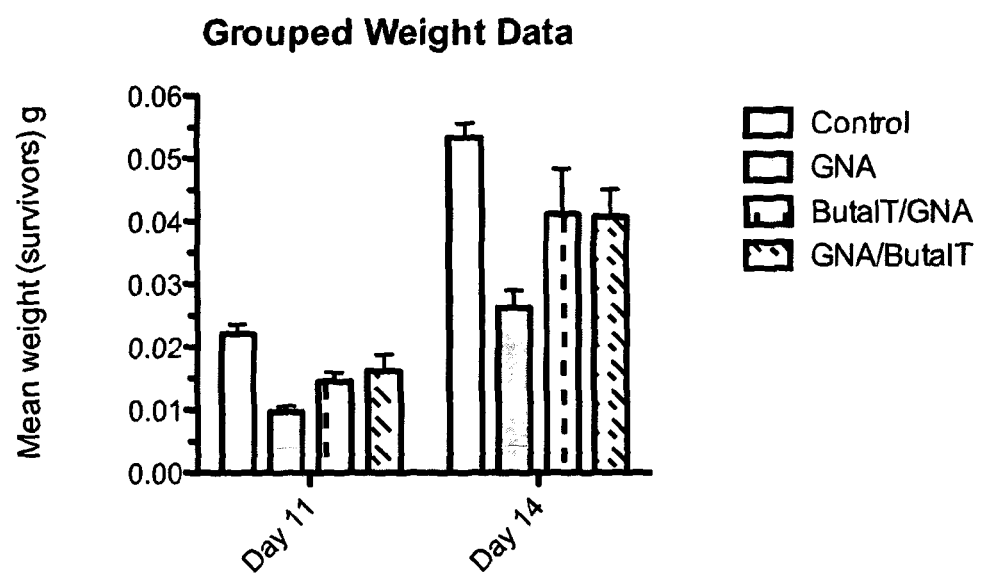

FIG. 17: (A) Kaplan-Meier survival plots of *Lacanobia oleracea* larvae (n=20 per treatment, * denotes n=60, **denotes n=40) exposed to GNA (line3), ButaIT/GNA (line 45) and GNA/ButaIT (line 5) expressing *Arabidopsis* leaves for 14 days from hatch and (B) the mean weight (±SEM) of surviving insects (n=20)

Figure 18:
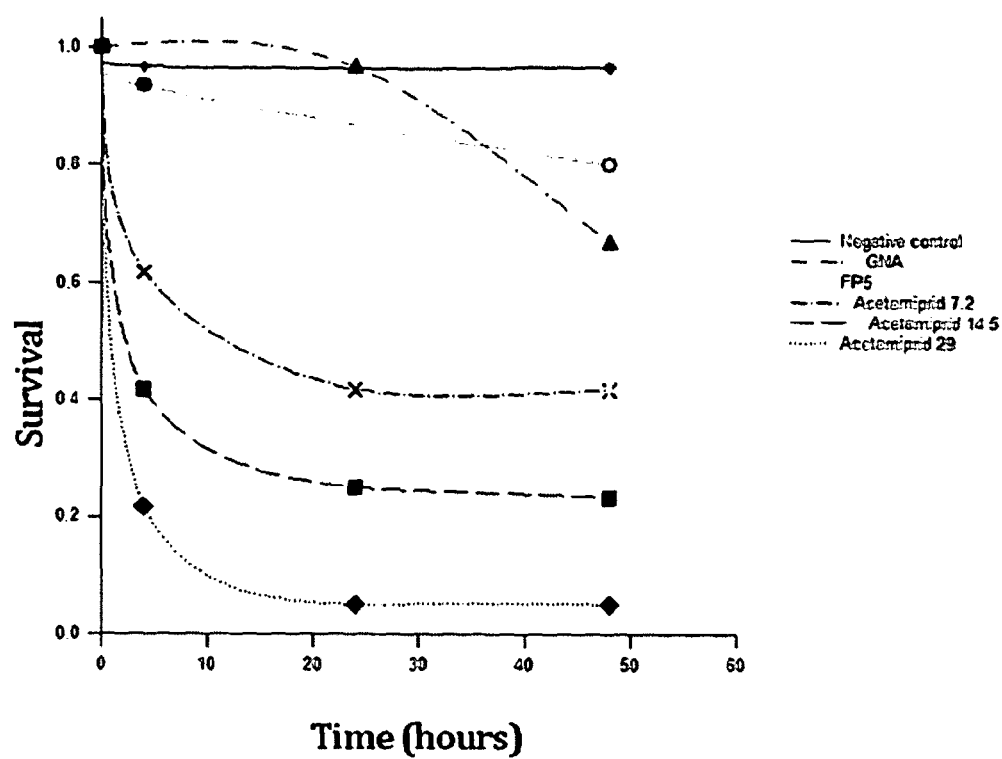

FIG. 18: Acute oral toxicity bioassay with adult worker honeybees. Insects (n=60 per treatment) were fed with sucrose (negative control), GNA (100 ug/bee), FP5 (100 ug/bee) or Acetamiprid at three different concentrations, covering the reported $LD_{50}$ of 14.5 ug/bee. Mortality was recorded after 4 h, 24 h and 48 h after the start of the test. Following Kaplan-Meier survival analysis, all treatments significantly differed from each other, with the exception of the comparison between GNA and FP5 treatments. The low mortality rates recorded for both treatments indicate that their $LD_{50}$ to honeybees was greater than 100 ug/bee.

Figure 19:
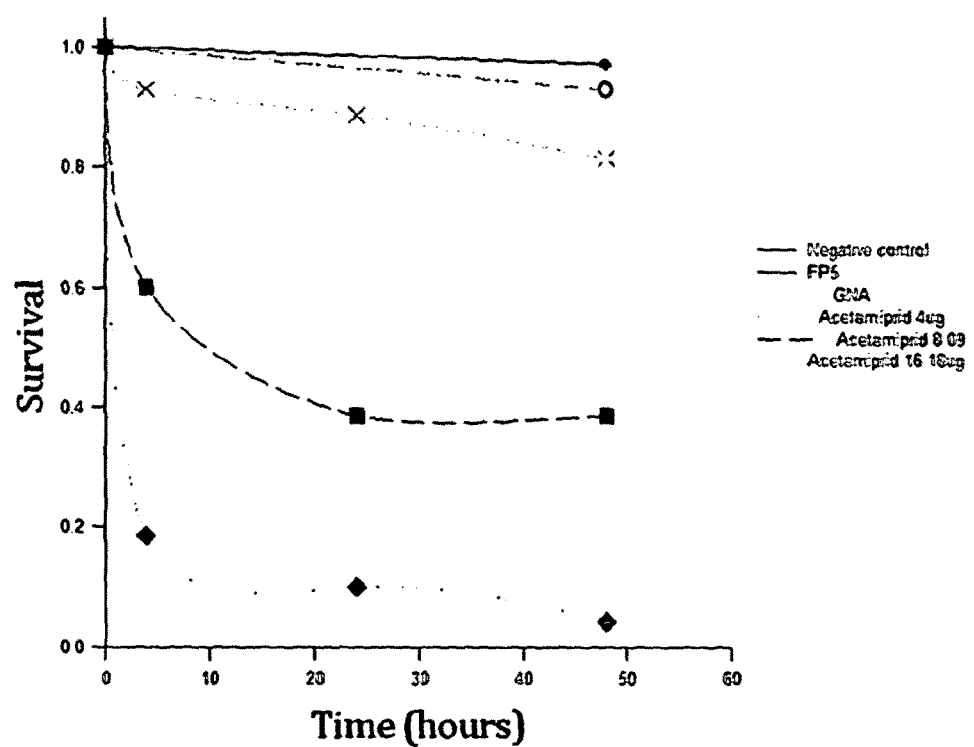

FIG. 19: Kaplan-Meier survival analysis for acute contact toxicity assay of GNA and FP5 with honeybees. Acetamiprid was used as positive control at three different concentrations. No significant differences were found between GNA or FP5 and the negative control (tween 0.05%), suggesting a lack of contact toxicity of these proteins towards honeybees. At the concentrations of the reported $LD_{50}$ (8.09 µg/bee) and 16.18 µg/bee, the positive control significantly differed from Negative control and GNA or FP5 treatments.

Figure 20:
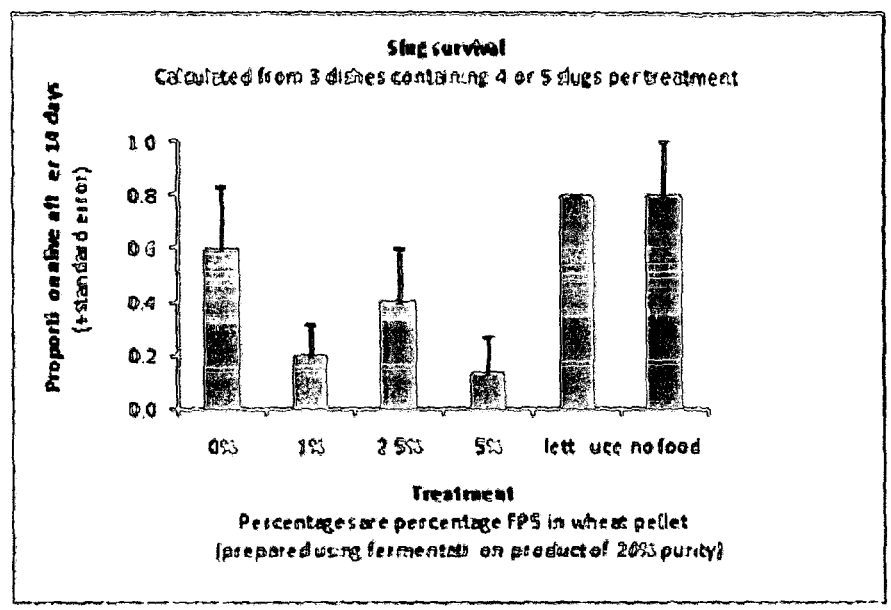
Figure 20:
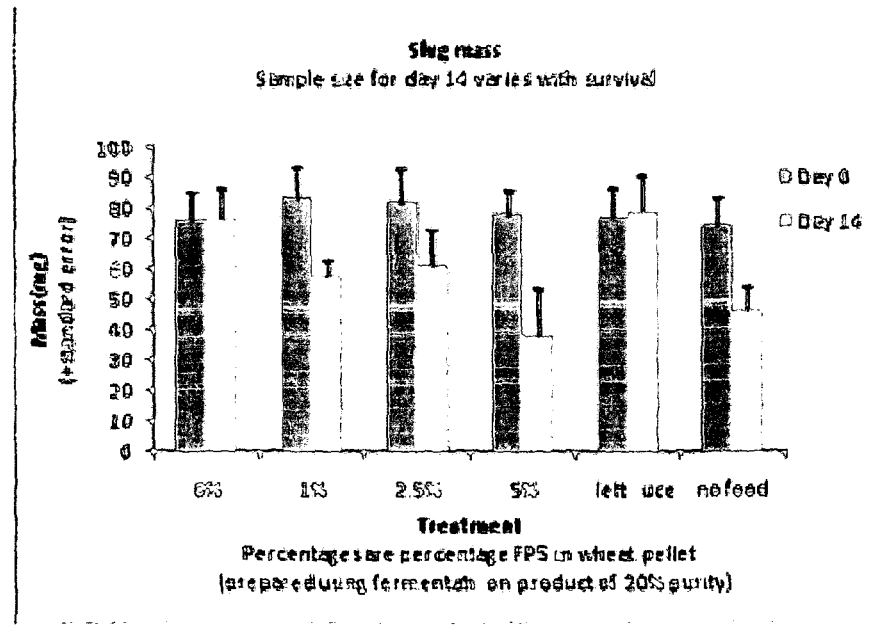

FIG. 20(A) shows survival recorded for slugs fed on pellets containing 0 (control), 1%, 2.5% and 5% (w/w) fusion protein. Additional control treatments are lettuce leaves and a no diet negative control. (B) Mean weight of slugs at the start (day 0) and end (day 14) of the bioassay.

Figure 21:
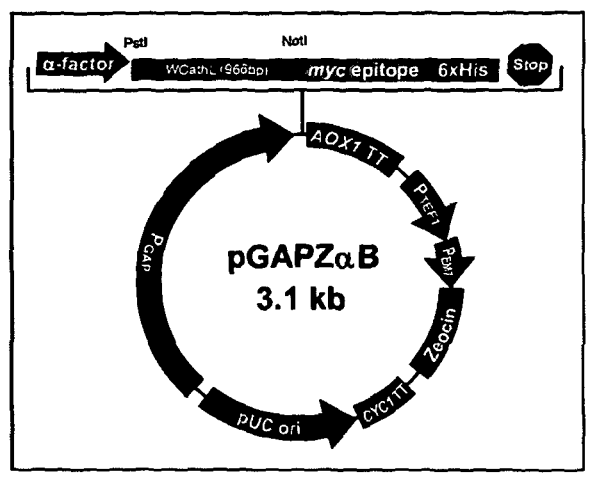
Figure 21:
Figure 21:

FIG. 21(A) shows diagrammatic representation of yeast expression construct pGAPZαB used for cloning of FP5 encoding genes. (B) Diagrammatic representation showing insertion of FP5 cassette, and (C) modification of vector to allow insertion of more than one FP5 cassette.

Figure 22:
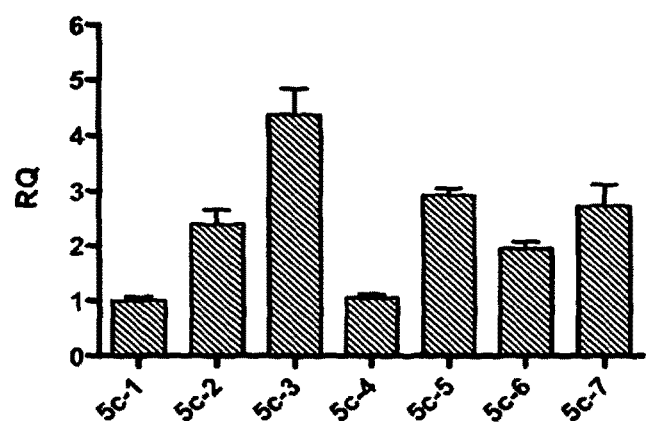

FIG. 22 shows results from qPCR analysis of yeast clones transformed with plasmid DNA containing 5 copies of the FP5 cassette. RQ denotes relative quantity of amplified products derived from CT (cycle threshold) values. Clone no is depicted on y-axis.

Figure 23:
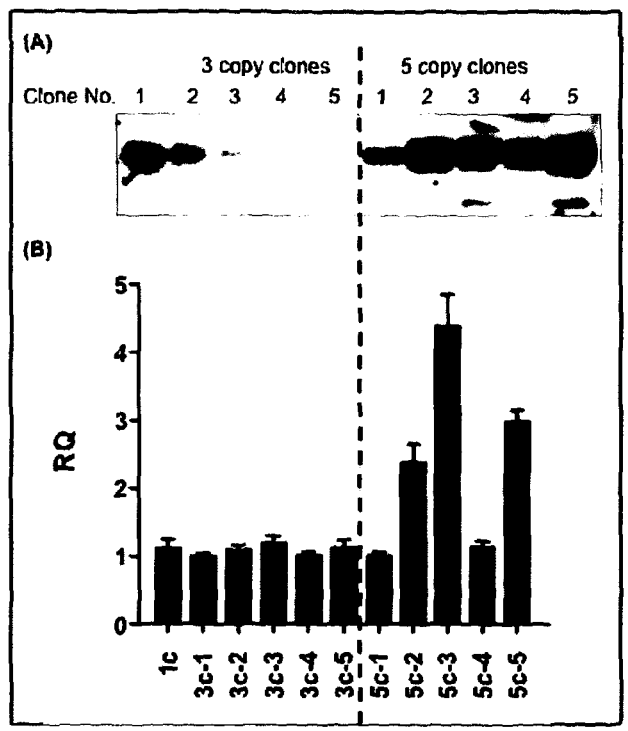
Figure 24:
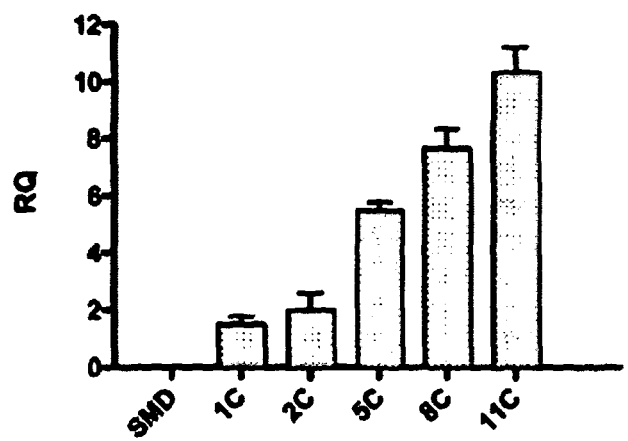

FIG. 23 shows representative analysis of (A) FP5 expression levels by western blotting (anti-GNA antibodies) of supernatant samples obtained from small-scale yeast cultures. Equal volumes were loaded for all samples analysed (B) qPCR analysis of clones FIG. 24 shows qPCR analysis of yeast (SMD) clones selected for bench-top fermentation. SMD corresponds to untransformed yeast.

Figure 25:
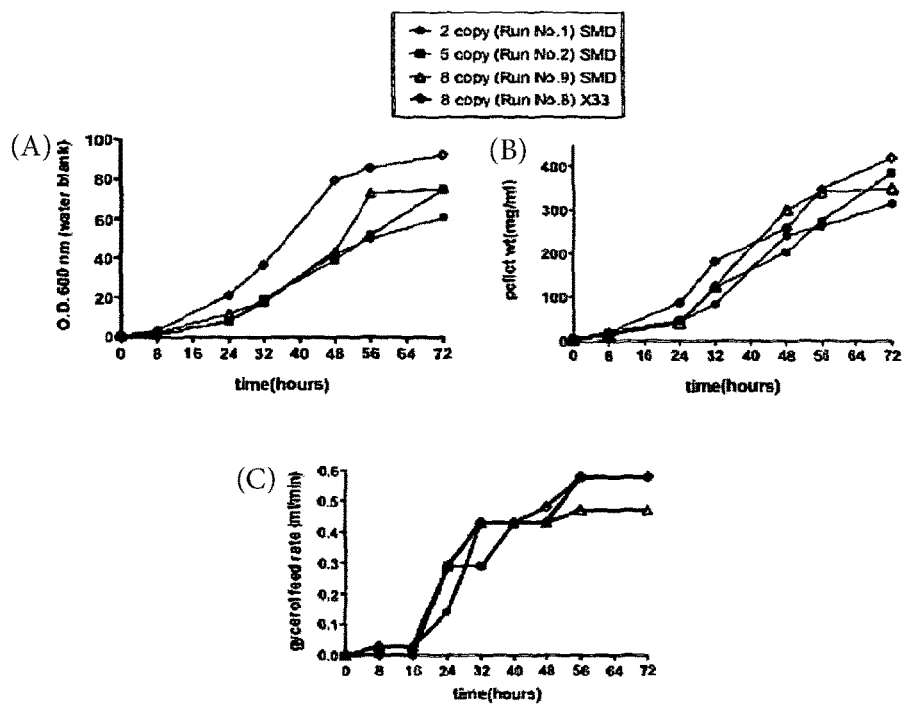

FIG. 25 (A) shows absorbance (O.D. 600 nm) (B) wet pellet weight and (C) glycerol feed rate recorded during bench-top fermentation of selected yeast clones containing 2, 5, and 8 FP5 expression cassettes (based on qPCR).

Figure 26:
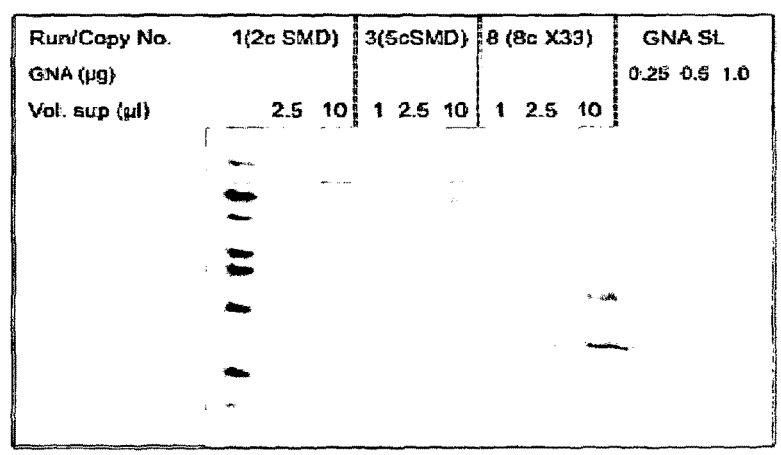

FIG. 26 shows representative SDS-PAGE (17.5% acrylamide gel) analysis of yield from fermentation of clones carrying more than one FP5 cassette. Prior to loading samples were de-salted as described above. Lane 1 is standard molecular weight marker mix (Sigma SDS-7; 66, 45. 36, 29, 24, 20, and 14 kDa).

Figure 27:
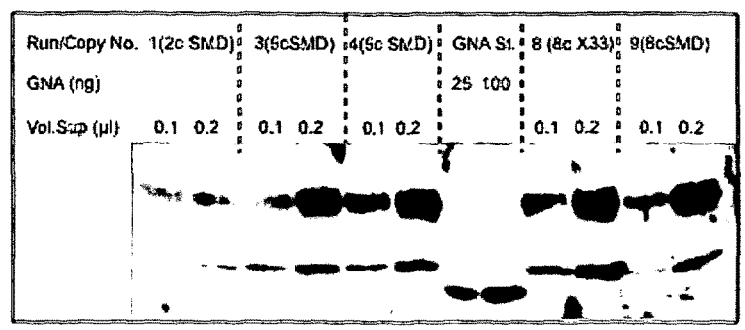
Figure 27:
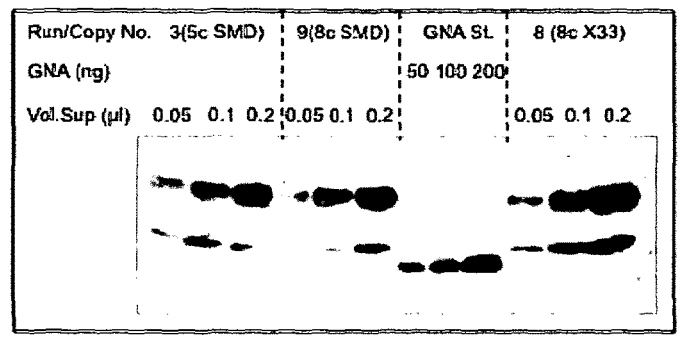

FIG. 27 shows western analysis (anti-GNA antibodies) of culture supernatants obtained following fermentation of clones carrying more than one FP5 cassette. Samples were run on SDS-PAGE gels, transferred to nitrocellulose and probed as described above. Yield is estimated by comparison of immunoreactivity of intact FP5 with GNA standards of known concentration.

Figure 28:
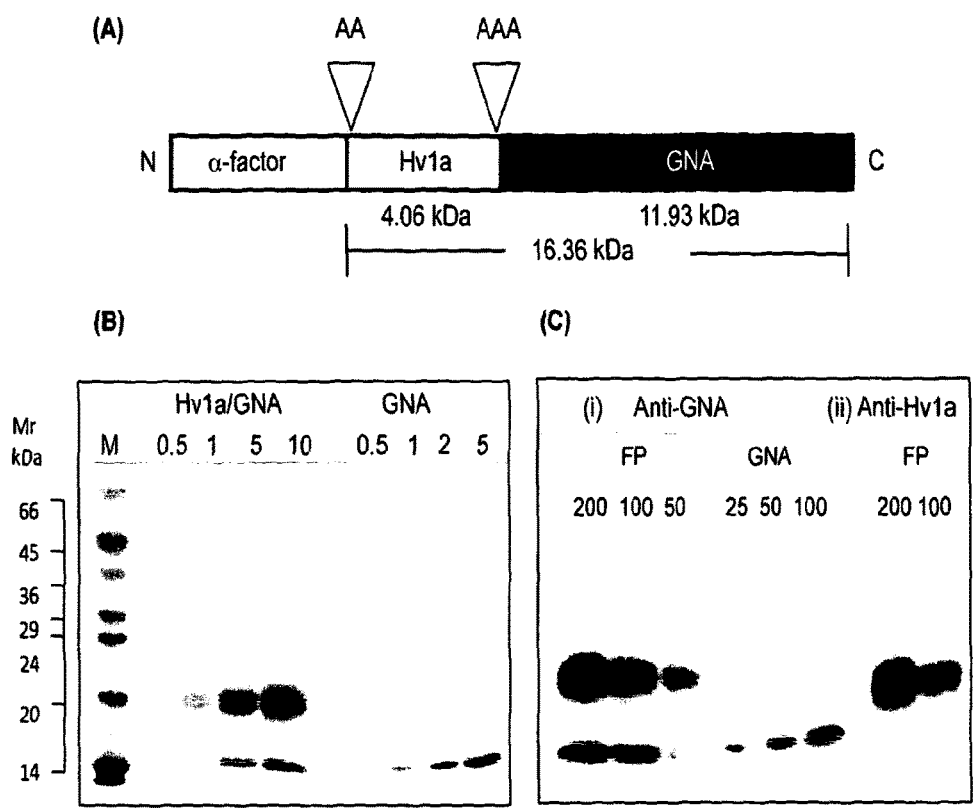

FIG. 28: Protein production and purification. (A) Schematic of construct encoding Hv1a/GNA showing predicted molecular masses of Hv1a and GNA as well as the total mass of the Hv1a/GNA fusion protein including the tri-alanine linker region and the additional two alanine residues at the N-terminus. (B) Coomassie blue stained SDS-PAGE gel (17.5% acrylamide) of recombinant Hv1a/GNA and GNA following purification by hydrophobic interaction and gel filtration chromatography. The approximate loading of protein (µg) is indicated above each lane, while the lane marked "M" contains molecular weight standards (Sigma SDS-7). (C) Composite of Western blots of recombinant proteins using (i) anti-GNA and (ii) anti-Hv1a antibodies. The approximate protein loading (ng) is denoted above each lane. FP denotes Hv1a/GNA fusion protein.

FIG. 29: Droplet feeding assays. (A) Mean weight of fifth stadium *M. brassicae* larvae fed daily sucrose droplets containing either 9.2 μg Hv1a, 40 μg Hv1a/GNA, or 40 μg bovine serum albumin (BSA, control). Significant differences between Hv1a/GNA and control or Hv1a treatments were observed at days 1-4 (ANOVA Tukey post hoc; day 1, P=0.0003; days 2-4, P<0.0001). The image (B) depicts control larvae on the left (BSA- and Hv1a-fed larvae) and Hv1a/GNA-fed larvae on the right. (C) Mean weight of fifth stadium *M. brassicae* larvae fed a single sucrose droplet containing either 40 μg Hv1a/GNA or control 40 μg BSA. Differences in mean weights between control and fusion protein treatments were significant from day 1 to day 6 of the assay (t-test; P<0.05).

FIG. 30: Leaf disc assays. (A) Survival of *M. brassicae* larvae fed from second stadia on cabbage discs coated with purified recombinant GNA (0.2% w/w) or Hv1a/GNA (0.2% w/w and 0.1% w/w) or on control PBS-coated discs (n=20 per treatment). (B) Mean weight of larvae recorded at day 10.

FIG. 31: Analysis of haemolymph and nerve chords. Immunoblot analysis using anti-GNA antibodies of (A) haemolymph samples extracted from *M. brassicae* larvae 48 h after feeding on diet containing Hv1a/GNA (2 mg/5 g diet). "C" denotes control haemolymph (larvae fed on diet with no added protein). Lanes 1 and 2 are replicates of pooled samples (3 larvae per sample); 15 μl of haemolymph was loaded in all cases. (B) Nerve chord samples dissected from sixth stadium larvae that had been injected with 25 μg GNA (lanes 1-4) or Hv1a/GNA (lanes 5-8). Pooled samples were extracted 3 h (lanes 1, 2, 5, and 6) or 5 h (lanes 3, 4, 7, and 8) post injection. Pooled samples (4 nerve chords per sample) were extracted directly in 40 µl SDS-sample buffer and 20 µl was loaded per lane. "C" denotes control nerve chord sample. In panels (A) and (B), S1 and S2 are 50 ng standards of GNA and Hv1a/GNA respectively.

Figure 32:
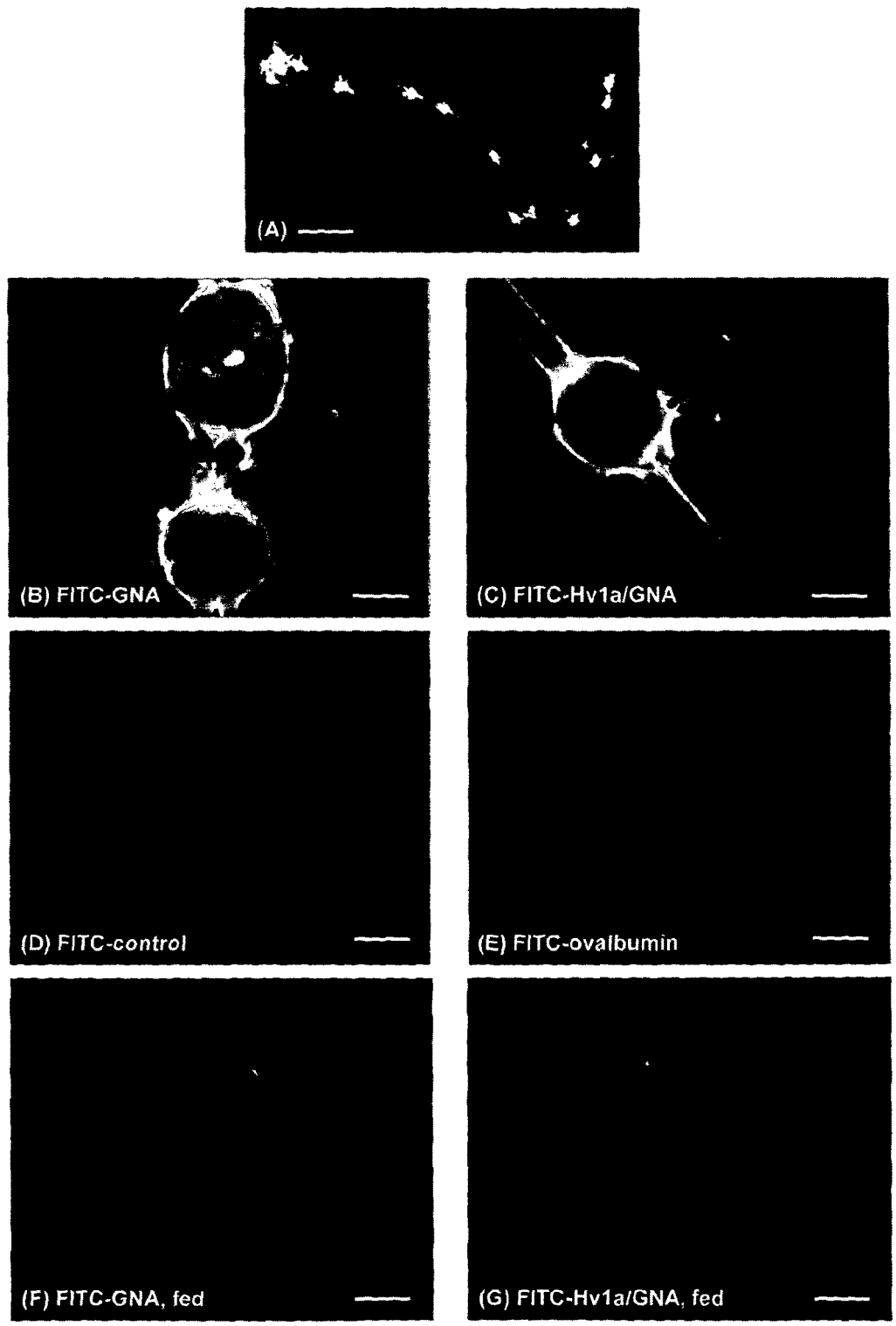

FIG. 32: Binding of GNA to nerve chords. (A) Intact nerve chord dissected from sixth stadium *M. brassicae* larvae. (B-F) Composite of partial images of nerve tracts dissected from larvae injected with, or fed on, FITC-labelled proteins. Images were visualised with a fluorescent microscope under FITC filter and captured in OpenLab. B: FITC-GNA; C: FITC-Hv1a/GNA; D: control FITC; E: FITC-ovalbumin; F: FITC-GNA; G: FITC-Hv1a/GNA. Scale bar=2 mm in (A) and 200 µM in (B-E).

EXAMPLE 1: DEVELOPMENT OF A FUSION PROTEIN PESTICIDE

Introduction

A venom peptide ω-ACTX-Hv1a, derived from the Australian funnel web spider (*Hadronyche versuta*) was selected as an insecticidal peptide candidate for attachment to GNA. When injected, ω-ACTX-Hv1a is known to have potent activity against a range of insects but is harmless to newborn mice and has no effect on vertebrate-muscle preparations (Fletcher et al., 1997; Chong et al., 2006). The toxin is thought to target insect voltage-gated calcium channels that are involved in a wide range of intracellular processes, including muscle contraction, hormone and neurotransmitter release, neurotransmission and the regulation of enzymatic reactions and gene expression (Catterall 2000).

A fusion protein incorporating ω-ACTX-Hv1a (referred to as omega/GNA or FP5) has been created and tested against a range of insect pests. Five different versions of the omega/GNA fusion protein have been created and expressed in *Pichia pastoris* and all have been evaluated for insecticidal activity.

B. Materials and Methods
B.1 Assembly of Expression Constructs for Omega/GNA Fusion Protein The ω-ACTX-Hv1a amino acid sequence (Genbank [P56207]) was used as the basis for the assembly of a synthetic omega gene. Codon usage was optimised for the expression of omega toxin in yeast. The coding strand was subdivided into 2 fragments and the complementary strand was subdivided into 3 fragments, such that the coding fragments overlapped the complementary strand fragments by 21 bases. Five oligonucleotide primers based on these fragments were synthesised, and used in an assembly reaction of the full mature omega coding sequence. All primers were individually 5'-phosphorylated using enzyme T4 polynucleotide kinase (Fermentas). An equimolar solution (100 pmol of each primer) of phosphorylated primers was boiled for 10 min, to denature secondary structures, and slowly cooled to room temperature to allow primers to anneal. After the addition of T4 DNA ligase (Promega), annealed primers (in ligase buffer) were left to ligate overnight at 4° C. To obtain sufficient DNA for cloning into the yeast expression vector pGAPzaB, the omega coding sequence was amplified by PCR, using primers containing 5' PstI and 3' NotI restriction sites. Following amplification, gel purification and restriction digest, the omega fragment was ligated into a previously generated yeast expression construct (Trung et al., 2006) containing the mature GNA coding sequence to create omega/GNApGAPZαB.

A second construct where a six residue histidine tag was incorporated at the C-terminus of the sequence encoding omega/GNA was also created. The mature GNA coding sequence was amplified by PCR using primers containing 5' NotI and 3' Sal I sites. The introduction of a 3' SalI site allows insertion of the GNA sequence in frame with the C-terminal histidine tag encoded by the pGAPZαB vector. Following restriction digest of omega/GNAGAPZαB and ligation of the GNA PCR fragment a new construct omega/GNA/HispGAPZαB was created.

Orientation of Omega Peptide Relative to GNA

A third construct where the sequence encoding for the omega atracotoxin was linked to the C-terminus of GNA was created as follows. The omega coding sequence (created as described above) was amplified by PCR, using primers containing 5' NotI and 3' SalI (including stop codon) restriction sites. Following amplification, gel purification and restriction digest, the omega fragment was ligated into a previously generated yeast expression construct containing the mature GNA coding sequence including an N-terminal six residue His tag to create HisGNA/omegapGAPZαB.

Modification to Improve Stability of Fusion Protein During Expression and Fermentation To reduce cleavage of the fusion protein during expression and purification a modification to the omega sequence was made. To this end a further construct was created whereby residue number 34 in the omega toxin (lysine; K) was replaced by a glutamine (Q) by site directed mutagenesis. This modification removed a potential Kex 2 signal cleavage site (KR) present at the C-terminus of the omega toxin. The omega sequence was modified by PCR using primers encoding a 5' Pst I site and 3' primer encoding a modified C-terminus (as above) and Not I site. The PCR product was restricted and ligated into similarly digested omega/GNApGAPZαB.

A further construct whereby the modified omega sequence was inserted at the C-terminus of GNA was also created. The sequence encoding the modified omega peptide was amplified by PCR, using primers containing 5'NotI and 3'SalI sites. After gel purification the PCR product was digested (NotI and SalI) and ligated into similarly digested pGAPZαB vector that contained an N-terminal Histidine tag and the sequence encoding GNA. A diagrammatic representation of all five constructs is given in FIG. 1.

Expression and Purification of Omega/GNA Fusion Proteins

Constructs for expressing recombinant proteins were transformed into *P. pastoris* (SMD1168H strain). Transformants were selected by plating on media containing zeocin (100 µg/ml). Clones expressing recombinant proteins were selected for production by bench-top fermentation by Western analysis of supernatants from small-scale cultures, using anti-GNA (1:3300 dilution) and anti-ω-ACTXHv1a (omega) (1:1000 dilution) antibodies supplied by Prof. Glenn King (Queensland University, Australia).

For protein production, *P. pastoris* cells containing fusion protein encoding sequences were grown in a BioFlo 110 laboratory fermenter. Briefly for fermentation 3×50 ml YPG (1% yeast extract [w/v]; 2% peptone [w/v]; 4% glycerol [v/v]) cultures (grown for 2-3 days at 30 vC with shaking) were used to inoculate 3 l of sterile minimal media (Higgins and Creggs, 1998) supplemented with PTM1 (Cino, 1999). Cultivation at 30° C., 30% dissolved oxygen, pH 4.5-5.0 with continuous agitation was continued with a glycerol feed (5-10 ml/h; 1.31 over 72 h). Secreted proteins were separated from cells by centrifugation (30 min at 7500×g). For omega/GNA, and MOD.omega/GNA recombinant proteins NaCl was added to the supernatant to a final concentration of 2M. Recombinant proteins were then purified by hydrophobic interaction chromatography on a phenyl-Sepharose (Amersham Pharmacia Biotech.) column (1 cm dia, 25 ml), run at 2 ml/min. After loading, the phenyl-Sepharose column was washed with 2M NaCl and eluted with a linear salt gradient (2M-0M) applied over 60 min. Recombinant proteins eluted at approx 1M NaCl. For fusion proteins containing histidine tags culture supernatant was diluted 1 in 4 with 4× Binding buffer (BB; 0.02M sodium phosphate; 0.4M NaCl; pH 7.4). Supernatants were loaded onto Ni-NTA (nickel affinity) columns (5 ml HisTrapFF columns from GE Healthcare). Typically 2×5 ml columns were linked and cultures loaded at 3-4 ml/min for 3-10 hours at room temperature with cycling. After loading the columns were washed with 1×BB and proteins were eluted from the columns with BB containing 0.15-0.2M imidazole).

Fractions containing purified proteins (analysed by SDS-PAGE) were then dialysed against distilled water and lyophilised. Lyophilised samples were subsequently assessed for purity and fusion protein content by SDS-polyacrylamide gel electrophoresis. The concentrations of recombinant proteins were estimated by comparison with known amounts of standard proteins by SDS-PAGE.

Biological Activity of Omega/GNA Fusion Proteins (i) Injection Bioassays: *Mamestra brassicae* (Lepidoptera)

Purified omega peptide was supplied by Prof. Glenn King (Queensland University, Australia), and omega/GNA variants were tested for biological activity by injecting 4-5 µl of aqueous samples (freeze-dried protein re-suspended in PBS) into newly enclosed fifth stadium *M. brassicae* larvae (30-70 mg). For each concentration tested 10-20 larvae were injected and toxic effects were monitored over 3 days. PBS was injected as a negative control.

(ii) Droplet Feeding Assays: *M. brassicae*

Several droplet feeding assays were conducted to assess oral activity of omega/GNA. Two assays are described herein.

Droplet Assay 1:

Newly moulted fifth stadium larvae were fed daily for 4 days on 5 μl droplets containing 40 μg of omega/GNA or 9.6 μg of omega toxin in 1×PBS and 10% sucrose solution. Control larvae were fed on droplets containing 40 μg BSA. To encourage droplet consumption larvae were starved for approx. 2-3 h prior to feeding. Larval weight was recorded daily approx. 1 h after droplet feeding. Treated larvae were placed individually in ventilated plastic pots (250 ml) with standard artificial diet. After 4 days of daily droplet feeding larvae were maintained on optimal diet until the onset of pupation.

Droplet Assay 2:

Newly moulted fourth stadium larvae were fed on a single 5 μl droplet containing 40 μg of omega/GNA or 40 μg BSA (control) in 1×PBS and 10% sucrose. Larvae were maintained as described above and weights recorded daily for 10 days.

(iii) Artificial Diet Feeding Assays: *M. brassicae*

Purified omega/GNA/His and His/GNA/omega proteins were incorporated at known concentrations (2.5 mg/5 g diet or 500 ppm) in artificial diet (Bio-Serv; powder containing cornflour, raw wheat germ, brewers yeast, ascorbic acid, benzoic acid, methyl parabenzoate) to assay for insecticidal activity against *M. brassicae* larvae. To prepare diets 1 g diet powder was mixed with 1 ml dist. water. Boiled agar (40 mg in 2 ml dist. water) was added to the mix and the test protein finally added in 1 ml of dist. water. Control treatments were GNA (at 5 mg/5 g or 1000 ppm) and diet without added protein. Larvae were selected for assay 48 hours after hatch. Two replicates of 10 larvae were assayed per treatment. Survival was assessed daily and larval wet weights recorded every two days.

(iv) Bioassays Against Colorado Potato Beetle (*Leptinotarsa decemlineata*) (Isagro Ricerca)

All five FP5 variants (omega/GNA; omega/GNA/His; MOD.omega/GNA; His/GNA/omega; His/GNA/MODomega) were tested for in vivo biological activity by feeding to three day old *Leptinotarsa decemlineata* larvae. Firstly, proteins were dissolved in sterilised demineralised water sprayed on young potato plants (350 ppm). Prior to spraying *L. decemlineata* larvae were transferred onto the plants, to assess the ingestion and contact efficacy of the fusion protein. Mortality was assessed daily for 6 days after the treatment. Secondly, to verify the persistence of FP5 efficacy, some larvae were moved to the treated plants one, two, and three weeks after the spray treatment.

(v) Bioassays Against Dipteran Wheat Bulb Fly *Delia coarctata*

Omega/GNA was tested for activity against wheat bulb fly larvae by injecting known concentrations (in 1 μl) of purified protein into a 2 cm length of wheat stem. Neonate larvae were introduced into the stem and monitored for survival after 3 and 7 days. Surviving larvae were placed into a newly injected stem after 3 days.

(vi) Bioassays Against Homopteran Cereal Aphid *Sitobion avenae*

Liquid artificial diet (Douglas and Prosser 1992) was used for the oral delivery of FP5 variants to cereal aphid *Sitobion avenae*. Omega/GNA/His, MODomega/GNA, His/GNA/omega, and His/GNA/MODomega were incorporated into diet at a concentration of 0.5 mg/ml (500 ppm). Diet-only and diet containing albumin were included as control treatments (100 μl artificial diet). A total of 100 μl of solution was used for each aphid feeding chamber, consisting of Perspex rings (40 mm diam.) overlain with 2 layers of stretched parafilm between which the diet was sandwiched. For assays *S. avenae* adult aphids were placed on artificial diet and left to produce nymphs overnight. Adults were then removed and the nymphs were maintained on the diet for a further 24 hours. Twenty nymphs per treatment were then transferred to feeding chambers (10 per replicate) containing test diets. Survival of the aphids was monitored daily for 10 days, with the diet refreshed as required.

(vii) Injection Bioassays: Mollusc Grey Field Slug *Deroceras reticulatum*

Omega/GNA/His was tested for activity against adult slugs (*D. reticulatum*) by injection into adult slugs (0.5-0.7 g). Slugs were chilled at 4° C. (for approx. 15 mins) prior to injection of 50 μg or 100 μg of purified omega/GA/His re-suspended in 25 μl PBS. Mortality was assessed daily for 7 days.

(viii) Feeding Bioassays: Mollusc Grey Field Slug *Deroceras reticulatum*

To test the effects of ingestion, juvenile slugs (10-40 mg) were fed on lettuce discs coated with omega/GNA/His (1 mg/leaf disc) or on wheat pellets containing purified of omega/GNA/His at a concentration of 1.3-2.2% w/w. For wheat pellet assays lyophilised fusion protein was added to heat-treated wheat flour (80° C. overnight). Water was added to the mix (at 0.5 ml/g dry weight) contained in eppendorf lids and the pellets subsequently oven dried (50° C. for approx. 2 h). Pellets with no added protein were prepared as above and used as a control treatment. Commercial pellets were used as a comparator. Slugs of comparable weights (10-20 mg or 30-40 mg) were selected and starved overnight at 15° C., RH 65%. Four individual replicates of 5 slugs were then placed into petri dishes lined with damp towel (to maintain humidity) and provided with leaf discs or pellets (placed on plastic weigh boats to prevent desiccation) for a period of 14 days. Survival was monitored daily and weights recorded at day 0, day 7, and day 14. Pellets were changed every 5-6 days and humidity maintained by the addition of water. In leaf disc assays consumption was estimated by the analysis of scanned leaf discs using J-image software.

(viiii) Statistical Analysis

All data analysis was conducted using the statistical functions of GraphPad Prism 5.0. Kaplan-Meier insect survival curves were compared using Mantel-Cox log-rank tests. Insect weights and sizes were analysed using either Student's t-tests or one-way analysis of variance (ANOVA). Analysis of growth curves was carried out by non-linear regression, fitting to a Weibull growth curve model. The accepted level of significance was P<0.05 in all cases.

Results

Expression and Purification of Omega/GNA Variants

Clones containing genes encoding the omega toxin linked to GNA were verified by sequencing prior to transformation into *P. pastoris* protease deficient cells. High expressers were selected by western analysis of small-scale cultures (using anti-GNA antibodies). Subsequently all fusion proteins were over expressed in bench-top fermenters, levels of expression of all versions of omega containing fusion proteins were approx 40-50 mg/l. Purification from culture supernatants was carried out either by nickel affinity or hydrophobic interaction chromatography. FIG. 2 shows representative SDS-PAGE analysis of all five omega/GNA variants after purification and lyophilisation. Western analysis of omega/GNA is presented in FIG. 3. As shown in FIG. 2 all three versions of fusion protein where the omega toxin is linked to the N-terminus of GNA show a degree of proteolytic cleavage with two major bands present in purified fractions. The larger molecular weight bands (approx 20 kDa) are close to the predicted sizes for all three omega/GNA variants (15.93-16.77 kDa) and these bands correspond to intact fusion protein as confirmed by western analysis in FIG. 3 which shows positive immunoreactivity of the protein with GNA and omega antibodies. The lower molecular weight proteins in FIG. 2 correspond to GNA from which the omega peptide has been cleaved as demonstrated by positive immunoreactivity of this protein with GNA, but not with anti-omega antibodies. The ratio of intact:cleaved protein in the samples differs for the different FP5 variants. For omega/GNA and omega/GNA/His the ratio of intact:cleaved protein is approx. 1:2, whereas the ratio for modified omega/GNA is approx. 2:1. Thus modification of the omega peptide has resulted in an increase in levels of intact fusion protein obtainable. Further analysis has found that stability during fermentation is similar for omega/GNA and MOD.omega/GNA but that the modified version is more stable than the non-modified form during downstream processing.

Purification of FP5 variants where the omega peptide is linked to the C-terminus of GNA (His/GNA/omega and His/GNA/MODomega) results in two major staining bands on SDS-PAGE gels (FIG. 2). Western analysis shows positive immunoreactivity of both proteins with anti-His antibodies confirming that both bands represent recombinant protein containing an intact N-terminal histidine tag (FIG. 3). Western analysis using anti-omega antibodies suggests that both proteins in His/GNA-omega samples (which both show positive anti-omega immunoreactivity) represent intact fusion protein with differentially processed N-termini. By contrast, only the larger protein in His/GNA-MODomega samples is immunoreactive with anti-omega antibodies suggesting that cleavage of the omega peptide occurs, resulting in a ratio of intact to cleaved protein for His/GNAMOD.omega of approx. 1:1.

Biological Activity (i) Injection Bioassays: *Mamestra brassicae* (Cabbage Moth)

Survival recorded for *M. brassicae* larvae injected with different doses of omega/GNA; His/GNA/omega; MODomega/GNA; His/GNA/MOD.omega; and omega peptide alone is shown in FIG. 4. All four versions of omega/GNA cause similar and significant mortality of larvae at injection doses of 20 µg and 10 µg suggesting that neither the orientation of the omega peptide relative to GNA or modification of the omega sequence significantly altered the insecticidal activity of the recombinant peptide. Mortality observed for fusion protein injected insects is comparable (on a molar basis) to that observed for insects injected with the omega peptide indicating that attachment of the toxin to GNA has not compromised the activity of the toxin significantly.

(ii) Droplet Bioassays: *Mamestra brassicae*

Droplets containing omega/GNA were fed to fifth instar *M. brassicae* larvae to determine if the fusion protein was orally toxic. FIG. 5(A) shows representative larval growth data recorded for larvae fed on a daily droplet containing 40 µg omega/GNA. Whereas ingestion of the omega toxin alone shows no effect on larval growth, ingestion of the omega/GNA fusion protein is seen to cause a significant reduction in larval growth with 40% mortality observed after larvae were fed daily droplets for 4 days. FIG. 5(B) shows that larvae fed on a single droplet containing 40 µg omega/GNA show significantly reduced growth as compared to controls for a period of approx. 6 days. By day 7 control larvae have attained their maximum weight after which a reduction in weight is observed as larvae enter the pupal phase (day 6-7). By contrast, larvae fed on omega/GNA show delayed growth reaching maximal weight at day 8-9, after which larvae pupated. Additional droplet assays have been conducted and comparable results obtained.

(iii) Artificial Diet Bioassay *Mamestra brassicae*

Purified Omega/GNA and His/GNA/omega were incorporated into artificial diet at 500 ppm and fed to *M. brassicae* larvae for 12 days. GNA at 100 ppm was fed as a control treatment. Survival and larval weight recorded is shown in FIGS. 6(A) and (B), respectively. A significant 85% reduction in survival was recorded for larvae fed on omega/GNA containing diets but no effect on survival was observed for insects fed on His/GNA/omega containing diets. Similarly larvae fed on omega/GNA show limited weight gain throughout the assay whereas His/GNA/omega fed insects show comparable weight gain to controls (GNA and no added protein diet treatments). This indicates that the orientation of the toxin relative to the carrier is critical for oral activity of the omega/GNA fusion protein towards lepidopteran larvae.

(iv) Bioassays Against *Leptinotarsa decemlineata* (Colorado Potato Beetle) Larvae A number of bioassays have been conducted to test the effects of omega/GNA variants on survival of Colorado potato beetle larvae and on the level of plant protection afforded by the fusion protein. Representative data is presented in tables 1, 2, and 3. In all cases significant larval mortality and reductions in plant damage (see FIG. 7), were observed for FP5 variants where the omega (modified and non-modified) was attached to the N-terminus of GNA (i.e. omega/GNA; omega/GNA/His; MODomega/GNA/His at concentrations of 350 ppm. As shown in Table 1, when plants were sprayed directly after application of larvae, 100% mortality for omega/GNA treatments was typically observed 5 days after the onset of the bioassay. In these assays damage to control plants was 95-100% (area leaf eaten) whereas plants sprayed with solutions containing omega/GNA (+/−His tag) or MOD/omega/GNA scored typically only 5-10% for leaf area consumed. Table 2 shows comparative data for four of the omega/GNA variants and it can be seen that attachment of the omega toxin (modified and non modified version) to the C-terminus of GNA results in a loss of biological activity against this coleopteran pest. This data is visually represented in FIG. 6. In assays to test the persistence of omega/GNA fusion protein, plants were sprayed for up to 22 days (11 day data presented) prior to application of larvae. In these bioassays similar effects on larval survival and plant damage were observed for omega/GNA fusion protein (where omega toxin is linked to the N-terminus of GNA) treated plants (Table 3) as compared to assays where direct action was assessed (Tables 1 & 2). This suggests that, in glasshouse conditions, omega/GNA fusion protein has activity that persists for more than 3 weeks. These bioassays have identified the omega/GNA fusion protein, where the omega toxin is linked to the N-terminus of GNA, as a candidate suitable for development as a control agent for coleopteran pests.

TABLE 1

Survival and plant damage recorded for Colorado potato beetle larvae fed on potato plants sprayed with solutions containing 350 ppm omega/GNA variants (omega/GNA; omega/GNA/His; modified omega/GNA). Three day old larvae were applied to plants directly before treatments were applied (n = 20 per treatment).
DIRECT ACTION

| | | 2 DAYS | | 4 DAYS | | 5 DAYS | |
|---|---|---|---|---|---|---|---|
| Product | Applic. Rate (ppm) | % mortality | % eaten leaf | % mortality | % eaten leaf | % mortality | % eaten leaf |
| control | — | 0 | 12 | 0 | 22 | 0 | 95 |
| Omega/GNA | 350 | 0 | 4 | 20 | 6 | 100 | 7 |
| Omega/GNA/His | 350 | 0 | 7 | 40 | 7 | 100 | 10 |
| MODomega/GNA | 350 | 0 | 6 | 15 | 6 | 95 | 10 |

TABLE 2

Survival and plant damage recorded for Colorado potato beetle larvae fed on potato plants sprayed with solutions containing 350 ppm omega/GNAvariants (omega/GNA/His; modified omega/GNA; His/GNA/omega; His/GNA/MODomega). Three day old larvae were applied to plants directly before treatments were applied (n = 30 per treatment).
DIRECT ACTION

| | | 2 DAYS | | 5 DAYS | | 6 DAYS | |
|---|---|---|---|---|---|---|---|
| Product | Applic. Rate (ppm) | % mort. | % eaten leaf | % mort. | % eaten leaf | % mort. | % eaten leaf |
| control | — | 0 | 22 | 0 | 22 | 0 | 95 |
| Omega/GNA/His | 350 | 0 | 10 | 70 | 14 | 70 | 19 |
| MODomega/GNA | 350 | 6.67 | 6 | 100 | 6.67 | | |
| His/GNAomega | 350 | 0 | 20 | 0 | 70 | 0 | 95 |
| His/GNA/MODomega | 350 | 0 | 17 | 0 | 72 | 0 | 92 |

TABLE 3

Survival and plant damage recorded for Colorado potato beetle larvae fed on potato plants sprayed with solutions containing 350 ppm omega/GNA variants (omega/GNA/His; MODomega/GNA) Blank denotes addition of surfactant to sample. Three day old larvae were applied to plants 11 days after treatments were applied (n = 20 per treatment).
PERSISTENCE 11 DAYS

| | | 13 DAYS | | 15 DAYS | | 18 DAYS | | 20 DAYS | |
|---|---|---|---|---|---|---|---|---|---|
| Product | Applic. Rate (ppm) | % mort. | % eaten leaf | % mort. | % eaten leaf | % mort. | % eaten leaf | % mort. | % eaten leaf |
| control | — | 0 | 30 | 0 | 75 | 0 | 100 | | |
| Omega/GNA/His | 350 | 5 | 2 | 40 | 8 | 55 | 20 | | |

TABLE 3-continued

Survival and plant damage recorded for Colorado potato beetle larvae fed on potato plants sprayed with solutions containing 350 ppm omega/GNA variants (omega/GNA/His; MODomega/GNA) Blank denotes addition of surfactant to sample. Three day old larvae were applied to plants 11 days after treatments were applied (n = 20 per treatment).

PERSISTENCE 11 DAYS

| Product | Applic. Rate (ppm) | 13 DAYS | | 15 DAYS | | 18 DAYS | | 20 DAYS | |
|---|---|---|---|---|---|---|---|---|---|
| | | % mort. | % eaten leaf | % mort. | % eaten leaf | % mort. | % eaten leaf | % mort. | % eaten leaf |
| MODomega/GNA | 350 | 10 | 5 | 50 | 10 | 85 | 12 | | |
| Omega/GNA/His + Blank | 350 | 0 | 2 | 30 | 12 | 55 | 18 | 60 | 40 |

(v) Bioassays Against Dipteran Wheat Bulb Fly *Delia coarctata*

Omega/GNA was tested for activity towards wheat bulb fly larvae by exposure to wheat stems injected with known concentrations (10 and 20 µg) of recombinant protein. As shown in Table 3 a significant and dose dependent reduction in survival was observed for larva exposed to wheat stems injected with omega/GNA. After 7 days of exposure a 50% and 100% reduction in survival was recorded for lava exposed to 10 and 20 µg omega/GNA, respectively as compared to a 20% reduction in survival recorded for the control (no added protein) treatment.

TABLE 4

Survival of wheat bulb fly (*Delia coarctata*) larvae after 3 and 7 days of exposure to wheat stems containing 10 and 20 µg of recombinant omega/GNA

| Treatment (µg per µl) | N | alive | dead | % survival |
|---|---|---|---|---|
| Survival Day 3 | | | | |
| Control - water | 87 | 83 | 4 | 95.4 |
| Omega/GNA (10 µg) | 25 | 19 | 6 | 76 |
| Omega/GNA (20 µg) | 18 | 6 | 12 | 33.3 |
| Survival day 7 | | | | |
| Control-water | 85 | 68 | 17 | 80 |
| Omega/GNA (10 µg) | 24 | 12 | 12 | 50 |
| Omega/GNA (20 µg) | 18 | 0 | 18 | 0 |

Day 7 data - note n values decrease because a few go missing and are removed from the dataset.

(vi) Bioassays Against Homopteran Cereal Aphid: *Sitobion avenae*

Omega/GNA variants were tested for oral activity against cereal aphids by incorporation into artificial diet at a concentration of 0.5 mg/ml (500 ppm). As shown in FIG. 8, all four tested versions of the fusion protein caused significant reductions in survival as compared to control treatments ($P<0.0001$; Mantel-Cox) with 100% mortality recorded after 6 days of feeding on diets containing different versions of FP5. Mortality was 100% four days after feeding on variants containing the modified omega peptide (MODomega/GNA/His and His/GNA/MODomega) and 100% 5 days and 6 days after feeding on His/GNA/omega and omega/GNA/His, respectively. This suggests that the position of the toxin relative to the carrier does not significantly affect activity against *S. avenae* but that modification to the omega peptide results in greater activity as compared to the unmodified peptide. GNA at this concentration in artificial diet does not have a significant effect on the survival of cereal aphids.

(vii) Injection Bioassays: Mollusc Grey Field Slug *Deroceras reticulatum*

As shown in FIG. 9, injections of omega/GNA/His into adult slugs (*D. reticulatum*, 0.5-0.8 g) caused a dose dependent reduction in survival. Mortality was significantly greater for slugs injected with 100 µg omega/GNA as compared to controls (Chi-squared $P<0.0001$), and significantly different between slugs injected with 100 pig and 50 µg fusion protein (Chi-squared $P=0.0015$).

(vii) Feeding Bioassays

Mollusc Grey Field Slug *Deroceras reticulatum*

To assess the oral activity of omega/GNA/His on *D. reticulatum* juvenile slugs were fed on lettuce discs coated with fusion protein (re-suspended in water) FIG. 10 shows (A) estimated consumption of leaf material and (B) mean weights for control and fusion protein treatments. A significant reduction in mean weight was observed for slugs exposed to fusion protein after 7 and 14 days of feeding as compared to controls ((t-test, $p<0.05$). Consumption of leaf material was also reduced for fusion protein fed slug, with a significant reduction in cumulative consumption, as compared to controls, recorded 14 days after the onset of the assay.

Juvenile slugs were also fed on wheat pellets containing omega/GNA/His to test for oral activity of the fusion protein. Prior to carrying out these trials the activity and stability of the fusion protein was shown to be stable to heat treatment (assessed by lepidopteran injection assay and western analysis). FIG. 11 shows weights recorded for slugs (n=20 per treatment) exposed to fusion protein (1.3% w/w), control (wheat pellets no added protein), or starved, for the duration of the assay. A significant reduction in mean weight was recorded at day 7 and day 14 for slugs that had either been fed on fusion protein or starved (ANOVA; Tukey test $P<0.05$) as compared to the control treatment.

FIG. 12 shows data obtained from two bioassays where slugs were grouped at day 0 for weight distribution so that 10-20 mg and 30-40 mg slugs were fed on either commercial metaldehyde (2-3% (w/w)) containing pellets; His/GNA/omega containing pellets (2.2% (w/w)); control pellets (wheat flour no added protein; or starved. Exposure to metaldehyde containing pellets resulted in a 40% reduction in survival for the 10-20 mg group but no reduction in survival for the larger 30-40 mg group of slugs. No significant effects on survival were observed for either group of slugs fed on wheat pellets containing fusion protein. After 7 days the mean weights for slugs exposed to no diet (starved), metaldehyde pellets, and fusion protein containing pellets all showed significant reductions as compared to the control wheat pellet treatment (ANOVA; Tukey test $P<0.05$).

Results from leaf disc and wheat pellet bioassays demonstrate that omega/GNA/His causes a significant reduction in the growth of juvenile slugs due to a significant reduction in consumption of fusion protein containing diets.

REFERENCES

Catterall, W. A., 2000. Structure and regulation of voltage-gated Ca2+ channels. *Annu. Rev. Cell Dev. Biol.* 16, 521-555.

Cino, J. 1999. High yield protein production from *Pichia pastoris*: a protocol for benchtop fermentation. New Brunswick Co. Inc. http://www.nbsc.com/papers/Default.asp.

Chong, Y., Hayes, J. L., Wen, S., Sollod, B. L., Hains, P. G., Hodgson, W. C., Broady, K. W., King, G. F., Nicholson, G. M., 2006, unpublished data.

Cregg, J., Vedvick, T. & Raschke, W. (1993) Recent advances in the expression of foreign genes in *Pichia pastoris*. Bioengineering Technology 11, 905-910.

Douglas, A. E., Prosser, W. A., 1992. Synthesis of the essential amino acid tryptophan in the pea aphid (*Acyrthosiphon pisum*) symbiosis. Journal of Insect Physiology 38, 565-568.

Fletcher, J. I., Smith, R., O'Donoghue, I. S., Nilges, M., Connor, M., Howden, M. E. H., Christie, M. J., King, G. F. (1997) The structure of a novel insecticidal neurotoxin, -atracotoxin-HV1, from the venom of an Australian funnel web spider. *Nature Struc. Biol.* 4, 559-566

Trung, N. Pham, Fitches, E., Gatehouse. J. A. (2006) A fusion protein containing a lepidopteran-specific toxin from the South Indian red scorpion (*Mesobuthus tamulus*) and snowdrop lectin shows oral toxicity to target insects. *BMC Biotechnol.* 6-18.

EXAMPLE 2: BUTALT FUSION PROTEINS EXPRESSED IN *ARABIDOPSIS THALIANA*

Expression Constructs:

The Gateway (Invitrogen) entry vector system was used to generate constructs for expression of insecticidal proteins in transgenic plants. Constructs containing the mature GNA coding sequence and the native pre-peptide ("leader"), and fusion proteins containing the complete GNA coding sequence and a coding sequence for red scorpion toxin (ButalT) were assembled in *E. coli* by standard molecular biology techniques, and verified by DNA sequencing. The fusion proteins contained ButalT in both N-terminal and C-terminal locations relative to mature GNA (ButalT/GNA and GNA/ButalT respectively). The sequences were then transferred to the Gateway system entry vector in an antisense orientation in relation to gateway recombination sites. The destination plasmid pK2WG7 (designed for antisense expression) was employed as final vector for plant transformation to produce a coding sequence in the correct orientation relative to the CaMV 35S promoter. The resulting final constructs are illustrated in FIG. 13. Codon sequences were not optimised for *Arabidopsis*. However the codons used were previously optimized for yeast expression which has similar codon preferences.

Transformation and Selection

*Agrobacterium tumefaciens* strain C58C1 was transformed with the constructs described above. The floral dipping method was used to transform *Arabidopsis* wild type plants (ecotype Columbia-1). Seeds from the dipped plants were surface sterilized and plated onto 0.5×MS10 plates containing 50 μg/μl kanamycin for selection of primary transformants ($T_0$).

Analysis of Expression

Selection of transformants on plates containing kanamycin resulted in 16 GNA transformants, 45 GNA/ButalT transformants and 48 ButalT/GNA transformants. Western blot analysis of primary transformants using anti-GNA antibodies showed expression of foreign protein in 4 lines of plants transformed with the GNA construct, 10 lines of plants transformed with the ButalT/GNA construct and 9 lines of plants transformed with the GNA/ButalT construct. At the $T_2$ stage, lines that appeared to be expressing highly were taken through to the $T_3$ stage to be used for bioassays. These plants were from the original; GNA lines 3 and 7, ButalT/GNA lines 40 and 45 and GNA/ButalT lines 5 and 32. Levels of protein expression for plants used in bioassays are shown in FIG. 3. GNA (line 3) (FIG. 15A) was estimated to contain GNA at approx. 0.15-0.2% total soluble protein. ButalT/GNA lines 40 and 45 (FIGS. 15B and 15C) had an expression level for fusion protein of approx. 0.1% total soluble protein. Expression of GNA/ButalT fusion protein in line 5 (FIG. 15D) was also at a level of approx. 0.1-0.15% total soluble protein. All transformants generated seemed to have normal morphological and developmental characteristics.

Effect of Transgenic *Arabidopsis* Expressing Fusion Proteins when Fed to Tomato Moth (*Lacanobia oleracea*)

20 neonate *Lacanobia oleracea* larvae were placed in pots (4 replicates, 5 larvae per pot) and allowed to feed on detached leaves of transgenic *Arabidopsis* plants. Survival was measured over the course of a 14-day period and weights were measured at days 11 and 14. Assays were repeated giving a total sample number of 40. Treatments used were control, GNA-expressing, ButalT/GNA fusion protein expressing, and GNA/ButalT fusion protein expressing. Two independent lines expressing the ButalT/GNA fusion protein (lines 40 and 45) were used.

Survival was observed to be significantly different between control insects (93% survival) and the ButalT/GNA line 40 (65% survival) (Mantel-Cox tests, P=0.0002) and also between GNA (line 3) (90% survival) and ButalT/GNA (line40) (Mantel-Cox tests, P=0.0074). There was no significant difference in survival between GNA and control treatments (Mantel-Cox tests, P=0.5552). There was no difference in mean weight between the treatments (Student's T test, P>0.05 in all cases) (FIG. 16). For the second ButalT/GNA line tested (45) there was a survival rate of 70% (FIG. 17). Again, this is significantly different from the control (Mantel-Cox tests, P=0.0015)

In contrast to plants expressing ButalT/GNA, the GNA/ButalT expressing line did not cause significant insect mortality. The difference in survival seen between the control and GNA/ButalT (85% survival) is not significant (Mantel-Cox tests, P=0.2889). There is also no significant difference in survival between GNA and GNA/ButalT (Mantel-Cox tests, P=0.6153). In this assay, GNA-expressing plants adversely affected insect growth. For both days 11 and 14 there was a significant reduction in mean weight (approx. 50%) between control and GNA treatments. (Student's T-test, P<0.05) Plants expressing fusion proteins also showed an effect on insect growth, but the reduction was lower (approx. 20%). There was a significant difference in weights seen at day 11 between control and ButalT/GNA (Student's T-test, P<0.05) but not at day 14 (P=0.072). At day 11 there is no significant difference in weight between control and GNA/ButalT (T-test, P=0.05), however at day 14 there is significance (P<0.05).

Comparisons of mean weights on both days between GNA and ButalT/GNA and GNA/ButalT show significance (P<0.05). Between GNA/ButalT (45) and ButalT/GNA (5) the difference in weight is not significant for both days (P>0.05).

CONCLUSIONS

1. Plants expressing the ButalT/GNA fusion protein (FP4) showed a consistent effect on mortality of neonate larvae of tomato moth (*L. oleracea*), with survival decreased by 30% when compared to controls. Plants expressing GNA or a GNA/ButalT fusion protein had no effect on larval mortality. These results are consistent with results obtained when purified recombinant protein is fed in artificial diet. The results amount to proof of concept that insecticidal fusion proteins can be produced in transgenic plants, and that when this is done, the insecticidal activity of the transgene product is retained.

2. While GNA has an inhibitory effect on larval growth under conditions when larvae are developing quickly (second assay), the fusion proteins have only marginal inhibitory effects. This suggests, as has previously been demonstrated, that the growth inhibitory effect of GNA on lepidopteran larvae is dependent on agglutination activity, since the fusion proteins have reduced agglutination activity compared to the recombinant lectin.

EXAMPLE 3

Toxicity Bioassays of his/GNA/MODomega (FP5) and Galanthusnivalis Agglutinin (GNA) on Honeybees (Oral and Contact Tests)

Acute oral and contact toxicity assays were carried out using adult worker honeybees (*Apismellifera*), according to the OECD guidelines (1998a, 1998b). Bees were collected from a single healthy colony at Newcastle University, on June/2011 and August/2011. In each assay, acetamiprid was used as a positive control at three concentrations, covering the reported $LD_{50}$ for oral and contact toxicities. GNA or FP5 concentrations of 100 µg/bee and 20 µg/bee were used for oral and contact bioassays, respectively. Six replicates of ten bees were used for each treatment on oral assays, and seven replicates of 10 bees on contact assays. Following Kaplan-Meier analyses, FP5 and GNA showed low oral acute toxicity levels towards bees (LD50>100 µg/bee; FIG. 18). No significant effects of FP5 or GNA were detected in contact toxicity assays (FIG. 19).

Furthermore, an injection bioassay was performed. Honeybees (three replicates of ten bees for each treatment) were injected with 20 µg of GNA or FP5 in 5 µl of PBS buffer using a Hamilton® syringe. Buffer only was used as a negative control.

Mortality was recorded at 4 h, 24 h and 48 h after the start of the test. All treatments significantly differed from each other, with GNA presenting higher toxicity than FP5.

The bioassays carried out followed the OECD guidelines for the effects of pesticides on honeybees. At the higher concentration recommended for the oral test (100 µg/bee), FP5 and GNA showed smaller effects on mortality than acetamiprid, reported to have a low toxicity on bees (Laurino et al., 2011). Additionally, neither FP5 nor GNA presented effects on the contact bioassays.

For the injection bioassays, FP5 had lower toxicity than GNA, with mortality occurring after 24 h and 48 h. In summary, the results suggest that FP5 and GNA have low toxicity on honeybees.

Laurino, D.; Porporato. M.; Patetta, A. and Manino, A. Toxicity of neonicotinoid insecticides to honey bees: laboratory tests. *Bulletin of Insectology*, 64(1): 107-113, 2001.

OECD. Guidelines for the testing of chemicals. Honeybees, Acute Oral Toxicity Test. Document number 213. 1998a.

OECD. Guidelines for the testing of chemicals. Honeybees, Acute Contact Toxicity Test. Document number 214. 1998b.

EXAMPLE 4

Feeding Bioassays: Mollusc Grey Field Slug Deroceras-reticulatum

To test the effects of ingestion, juvenile slugs (70-80 mg) were fed on wheat pellets containing purified of MODomega/GNA/His at a concentration of 0-5% w/w. For wheat pellet assays lyophilised fusion protein was added to heat-treated wheat flour (80° C. overnight). Water was added to the mix (at 0.5 ml/g dry weight) contained in eppendorf lids and the pellets subsequently oven dried (50° C. for approx. 4 h). Pellets with no added protein were prepared as above and used as a control treatment. Additional treatments were lettuce leaves and a no diet (negative control) treatment. Slugs of comparable weights were selected and starved overnight at 15° C., RH 65%. Four individual replicates of 4-5 slugs were then placed into petri dishes lined with damp towel (to maintain humidity) and provided with leaf discs or pellets (placed on plastic weigh boats to prevent desiccation) for a period of 14 days. Survival was monitored daily and weights recorded at day 0, day 7, and day 14. Pellets were changed every 5-6 days and humidity maintained by the addition of water.

EXAMPLE 5

Generation of Multi-Copy High Expressing MODomega/GNA/His Clones

Section 1 Generation of Constructs Containing Multiple Copies of the Genes Encoding for FP5

1.1. Generation of Expression Constructs

Invitrogen's *Pichia* expression vector pGAPZαB (see FIG. 21A) was used for the generation of clones containing multiple FP5 cassettes. The FP5 coding sequence was cloned between PstI and XbaI sites to prepare an initial expression cassette consisting of the GAP promoter region, FP5 encoding sequence (containing C-terminal histidine tag) and AOX terminator sequence (FIG. 21B). The expression vector required modification to enable subsequent insertion of multiple FP5 cassettes into the yeast genome. Conventional transformation requires linearization of the vector with Bln/to encourage homologous recombination. This site cannot be used for linearisation of plasmids containing multiple FP5 cassettes as Blnl is present in all FP5 cassettes. Thus, aHindIII site was added 45 bp away from original Blnl site on the 3' end of vector using conventional molecular techniques (FIG. 21C). The HindIIIsite allows linearisation of plasmids (without loss of FP5 cassettes) before *Pichia* transformation.

Subsequently, constructs containing 2, 3, 4, 5, 7, and 11, FP5 cassettes were generated using conventional restriction digest and ligation techniques.

Transformation of Constructs (SMD and X33)

Single copy, 3 copy, 5 copy, 7 copy and 11 copy (Hind III) linearised plasmids were transformed into the SMD 1168H (Protease deficient)*Pichia* strain using standard Invitrogen kit protocols. For X33 strain transformations, only an 11-copy plasmid was transformed. Transformants were selected on antibiotic containing plates (100 µg/ml zeocin)

Copy Number Determination by q-PCR: Methodology

Selected yeast clones (minimum of 5 clones per copy number) were grown in 10 ml YPG baffled flasks at 30° C. for 72 hours. Genomic DNA (gDNA) was extracted as per Marko et al. (2011) and quantified using Nanodrop. A 10 ng/ul stock was prepared for all samples. Gene specific primers were designed to amplify a partial sequence of FP5 using Primer Design software suitable for Applied Biosystem's qPCR machines and SYBR (cyber Green) reagents. The actin gene was used as endogenous control for gene expression level. 50 ng of gDNA was used as a template for qPCRs. Copy numbers of FP5 were compared with either untransformed SMD or a one copy *Pichia* clone (which was selected as lowest amplification in 1 copy transformation, though few clones of 1 copy showed 2 copies due to double integration). The following primers were used for qPCR:

```
For FP5 amplification:
                                (SEQ ID No: 18)
Fwd 5'TGGTCTCTCCCGTAGCTGCTT
                                (SEQ ID No: 19)
Rev 5'ATCGAACAAACCGATTTGGG For Actin amplification:
                                (SEQ ID No: 20)
Fwd 5' CGGTATGTGTAAGGCCGGATA
                                (SEQ ID No: 21)
Rev 5'ACGACCGATGGGAACACTGT
```

Copy Number Determination by q-PCR: Results

At least 5 yeast clones per copy number were analysed in triplicate by qPCR. Representative data presented in FIG. 22 shows that transformation of *Pichia* with multi-copy plasmids does not result in all clones containing the same number of FP5 cassettes. All multi-copy transformed yeast clones were shown to contain different copy numbers (e.g. 5 copy plasmid showed presence of 1 copy, 2 copies and 5 copies) suggesting full integration of plasmid DNA into the yeast genome is not guaranteed. Interestingly, one clone derived from 5 copy transformation showed presence of 8 copies and this was thought be due to one complete and one partial integration (5+3) of DNA. For SMD, among screened clones transformed with an 11-copy plasmid only one was shown to contain 11 copies of the FP5 cassette. X33 clones transformed with an 11-copy plasmid were found to contain 1, 2, 4, 5, and 8 FP5 cassettes.

Small-Scale Screening

Following qPCR analysis selected clones were analysed for protein expression in small-scale (10 ml) YPG cultures. Following growth at 30° C. for 48 hours cultures were centrifuged and supernatant samples (boiled in presence of SDS sample buffer: 312.5 mM Tris-HCl pH 6.8, 10% SDS (w/v), 10% β-mercaptoethanol (v/v), 50% glycerol (v/v), 0.01% bromophenol blue (w/v)) were loaded onto SDS-PAGE gels alongside GNA standards. Proteins were transferred onto nitrocellulose using an ATTO HorizBlot semidry electroblotting system and probed with polyclonal anti-GNA antibodies (1:3300 dilution in 5% milk powder; PBS; 0.1% Tween 20). Chemiluminescent signals were detected on Fuji medical X-ray film following 1 min incubation with detection reagent (1M Tris-HCl pH 8.5, 0.2 mM coumaric acid, 1.25 mM luminol, 0.006% (v/v) hydrogen peroxide).

Overall, when results obtained from small-scale western analysis of expression levels are compared to qPCR results it can be seen that levels of expression correspond roughly to the number of copies present in the analysed yeast clones. (FIG. 23: i.e. clones containing 1-3 copies show lower expression as compared to those containing >3 copies). However, the expression of FP5 in small-scale cultures is not directly proportional to the number of integrated FP5 cassettes. This is thought to be due to differences in parameters such as oxygen levels in small-scale cultures. As a consequence clones were selected for bench-top fermentation based on qPCR results. FIG. 24 shows qPCR results for clones selected for comparison of expression levels by bench-top fermentation.

Section 2: Lab-Scale Fermentation of Selected Clones and Yield Estimate

Clones containing more than one copy of the FP5 expression cassette were selected for bench-top fermentation. Copy number was based on qPCR analysis described in section 1 (FIG. 24). Nine fermentation runs have been carried out in a bench-top fermenter BioFlo 7.5 L (New Brunswick).

Methods

Fermentation Parameters

All runs were carried out in a 5 liter BioFlo 110 (New Brunswick) fermentation vessel with 2.5 liters of basal salt media (supplemented with PTM1 salts). Fermenters were seeded with 180 mls YPG inoculum (unless otherwise stated) grown at 30° C. for 72 hours. A sterile glycerol feed of 1.25 liters (50% v/v) was fed over a fermentation period of 72 hours. Dissolved oxygen set point of 30% (rpm 250-750 fluctuation), pH 4-4.5 at onset and raised to 4.7-4.9 within 5 hours of inoculation, temperature was maintained at 30° C. throughout.

Analysis of Yield and FP5 Content in Lyophilised Samples

Yield estimates following fermentation of selected clones were obtained by SDS-PAGE analysis and western blotting (using anti-GNA antibodies). Western blotting gives a more accurate assessment of yield due to the poor Coomassie blue staining of the omega component of recombinant FP5 on SDS-PAGE gels.

For SDS-PAGE analysis samples of culture were desalted by passing through centrifugal concentrators (Vivaspin 30 000 or 50 000 MWCO) prior to the addition of 5×SDS sample buffer and boiling (10 mins). Samples were then loaded onto 17.5% acrylamide mini-gels alongside molecular weight markers (Sigma SDS-7) and GNA standards. Gels are stained for total proteins with Coomassie Blue and a visual estimation of protein content is made. For Western analysis samples are diluted in distilled water prior to loading on SDS-PAGE gels alongside GNA standards (as described in section 1.4).

Results

Fermentation: Culture Growth

FIG. 25 shows representative absorbance (O.D. 600 nm), wet pellet weight, and glycerol feed rates recorded for FP5 selected clones grown in bench-top fermenters under the conditions specified above. Similar increases in absorbance and wet pellet weights with time for the different clones clearly indicates that cell growth is not reduced in strains carrying more than one, and up to 8, FP5 cassettes. Cell growth (depicted by O.D. and wet pellet wt.) was greatest for the 8-copy x33 clone as compared to growth of transformed SMD clones. The wild type strain X33 is known to be a more robust and faster growing strain as compared to the protease deficient strain SMD1168H.

Fermentation: Analysis of Yield

Representative analysis of culture supernatants derived from bench-top fermentation is presented in FIG. 26 (SDS-PAGE) and FIG. 27 (western analysis). Previous data obtained from fermentation of SMD clones containing a single FP5 expression cassette (several fermentation runs results not shown) has determined a baseline yield of 100 mg/liter culture supernatant. As previously outlined, and shown in FIG. 26 the omega peptide component of FP5 stains poorly on SDS-PAGE gels using Coomassie dye whereas western analysis is a more sensitive method for predicting protein quantity (FIG. 27). It is clear that increasing the number of FP5 cassettes results in an increase in production of the FP5 fusion protein. In addition, growth and expression is increased in wild type X33 clones as compared to protease deficient SMD1168H clones. Previously SMD1168H has been the strain of choice for the expression of fusion proteins as expression in X33 has resulted in more cleaved product. In the case of FP5 (MODomega/GNA/His) no significant decrease in the production of intact fusion protein is observed for the X33 expressing strain as compared to SMD1168H strain. Table 5 shows a summary of fermentation runs carried out during the reporting period. To date the highest expression level achieved is approx 1 g/liter culture supernatant obtained from an X33 clone carrying 8 copies of the FP5 cassette. It can be seen in FIG. 26 for high expressing strains that FP5 and cleaved GNA represent more than 50% of total protein in the culture supernatant. It is not yet clear if this is the limit for the expression of this fusion protein using their present procedures. It is noted that a single fermentation run with an 11-copy SMD clone did not result in a high yield.

EXAMPLE 7

Oral Activity of Hv1a/GNA Against *Mamestra brassica* Larvae

Synthetic Gene and Fusion Protein Construct Assembly

A synthetic gene encoding the mature Hv1a amino acid sequence was assembled using a series of overlapping oligonucleotides, with codon usage optimised for expression in yeast (Table 5). Following assembly, the coding sequence was amplified by PCR and ligated into a yeast expression vector (derived from pGAPZαB) that contained a sequence coding for the mature GNA polypeptide (amino acid residues 1-105). The 37-residue Hv1a peptide was fused to the N-terminus of GNA via a tri-alanine linker sequence as depicted in FIG. 28A. The Hv1a/GNA construct was cloned such that the N-terminal yeast α-factor prepro-sequence would direct the expressed protein to the yeast secretory pathway. The final Hva1/GNA fusion protein is predicted to contain an additional two alanine residues at the N-terminus (after removal of the prepro-sequence) and terminate at residue 105 of the mature GNA protein, giving a predicted molecular mass of 16.36 kDa. The Hv1a/GNA-pGAPZαB construct was cloned into *E. coli* and the coding sequence was verified by DNA sequencing.

Table 5 Details of fermentation of selected *Pichia* FP5 expressing clones. Copy number is designated according to qPCR analysis (section 1). For column stating clone number and strain, the number in brackets is that of the copy number of the construct used for *Pichia* transformation (SMD is protease deficient and X33 is wild type strain). n/a denotes not analysed.

| Run No. | FP5 Copy No. (q-PCR) | Clone No. | Final Culture Volume (litres) | Final wet cell density (mg/ml) | Yield estimate (mg/l) |
|---|---|---|---|---|---|
| X(baseline) | 1 | 4 (1c/SMD) | 2.4 | 325 | 100 |
| 1 | 2 | 3 (1c/SMD) | 2.7 | 316 | 200 |
| 3 | 5 | 5 (5c/SMD) | 2.55 | 386 | 600 |
| 4 | 5 | 3 (7c/SMD) | 2 (overspill) | 455 | 600 |
| 5 | 5 | 2 (11c/SMD) | 2.4 | 205 | n/a |
| 6 | 2 | 3 (11c/SMD) | 2.4 | 375 | 200 |
| 7 | 11 | 7 (11c/SMD) | 2.4 | 365 | 200 |
| 8 | 8 | 1 (11C/X33) | 2.4 | 420 | 1000 |
| 9 | 8 | 2(5c/SMD) | 2.4 | 350 | 600 |

Expression and Purification of Recombinant Hv1a/GNA Fusion Protein

DNA from a verified Hv1a/GNA-pGAPZαB clone was linearised, transformed into the protease-deficient *P. pastoris* strain SMD1168H, and selected on antibiotic containing plates. Ten clones were analysed for expression of recombinant protein by Western blot (using anti-GNA antibodies) of supernatants derived from small-scale cultures (results not shown). This allowed selection of the best expressing clone for fusion protein production by bench-top fermentation.

For fusion protein production, *P. pastoris* cells were grown in a BioFlo 110 laboratory fermenter. Recombinant GNA was expressed and purified as previously described (Trung N P, 2006). The Hv1a/GNA fusion protein was purified from clarified culture supernatant by hydrophobic interaction chromatography followed by a second gel-filtration step to remove high molecular weight contaminating yeast proteins. Two major proteins of ~20 kDa and ~14.5 kDa were recovered following fermentation and purification of recombinant Hv1a/GNA (FIG. 28B). The 20-kDa protein migrates at a higher than expected molecular weight than the 16.36 kDa predicted for intact fusion protein. However, Western blot analysis (FIG. 28C) using anti-GNA and anti-Hv1a antibodies confirmed that the higher molecular weight protein represents intact fusion protein as it is immunoreactive with both anti-GNA and anti-Hv1a antibodies. The lower molecular weight band, which does not show positive immunoreactivity with anti-Hv1a antibodies, represents GNA from which the Hv1a peptide has been cleaved. Analysis of samples taken during fermentation confirmed that cleavage of the fusion protein occurs during expression and not during purification (results not shown). Intact Hv1a/GNA fusion protein was expressed at levels of ~50 mg/l of culture supernatant. The ratio of intact fusion protein to cleaved GNA was consistently 2:1 as judged by SDS-PAGE gels and Western blots.

Injection Toxicity of Hv1a/GNA and Hv1a

The biological activity of Hv1a/GNA was verified by injection of 5-20 μg of purified fusion protein into fifth stadium M. brassicae larvae (40-70 mg). Injections of comparable molar amounts of recombinant Hv1a (2.3-9.2 μg) were also conducted. Larval mortality occurred over a period of 4 days (Table 7) but was observed predominantly within the first 48 h following injection.

Larvae injected with higher doses of fusion protein (10 μg and above) or toxin alone (4.6 μg and above) displayed symptoms of paralysis, and survival was significantly reduced as compared to the control treatment (Kaplan-Meier survival curves; Mantel-Cox log-rank tests; $P<0.001$). Levels of mortality were comparable between fusion protein injected and toxin injected treatments (e.g., 80% mortality for larvae injected with 92 μg toxin/g insect compared to 90% mortality for larvae injected with 100 μg toxin as a component of fusion protein/g insect).

Oral Toxicity of Hv1a/GNA and Hv1a

Figure 29:
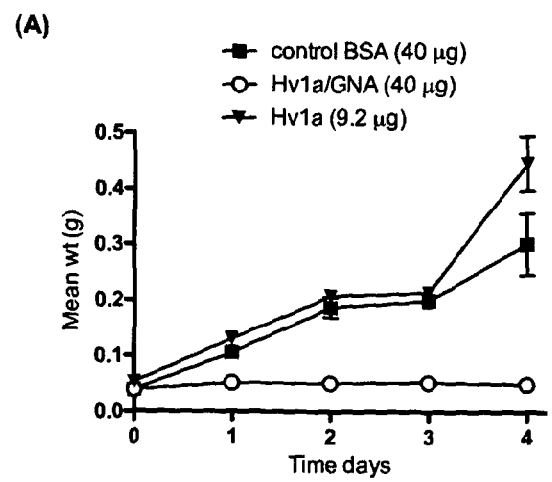
Figure 29:
Figure 29:
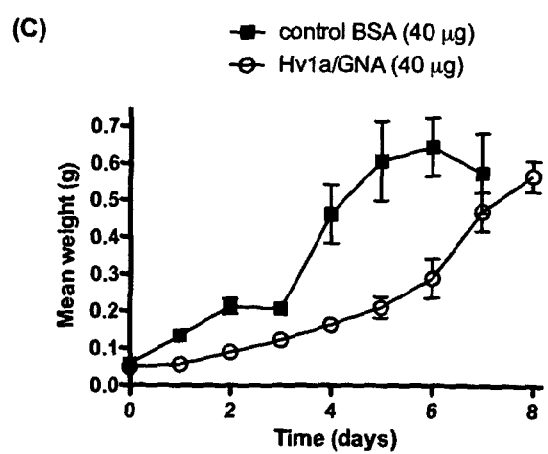

Several experiments were performed to assess whether fusion to GNA was able to improve the oral toxicity of Hv1a. First, fifth stadium M. brassicae larvae were fed daily for four days on droplets containing 40 μg of purified fusion protein or 9.6 μg Hv1a (FIG. 29A). Ingestion of daily droplets of fusion protein was found to result in a complete cessation of larval feeding evidenced by the significantly reduced mean weight recorded for this treatment as compared to the control group. After four days, 40% of the treated larvae were dead and the remaining insects did not survive to pupation. In striking contrast, no reduction in larval growth as compared to the control BSA treatment was observed for larvae fed on droplets containing Hv1a, indicating that the oral toxicity of Hv1a is dramatically enhanced by fusion to GNA.

In a second assay, fourth stadium larvae were fed on a single droplet containing 40 μg of Hv1a/GNA (FIG. 29B) and this was shown to cause a reduction in larval growth as compared to control-fed larvae over a period of approximately six days. By day 7, control larvae had attained their maximum weight after which a reduction in weight was observed as insects enter the pre-pupal phase (day 6-7). By contrast, larvae that had ingested a single Hv1a/GNA-containing droplet exhibited a reduced growth rate reaching maximal weight at day 8-9, after which larvae pupated.

Figure 30:
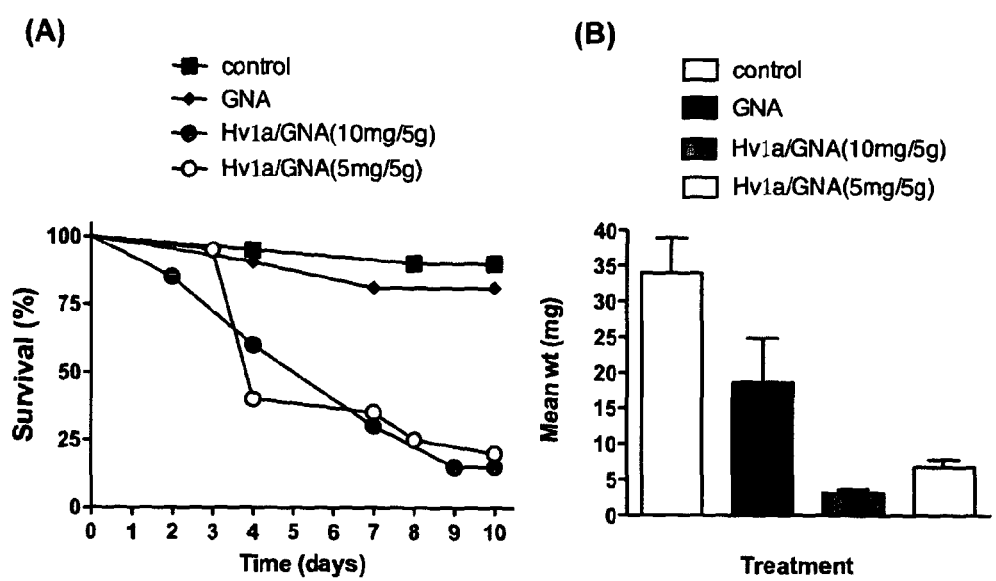

The oral toxicity of the Hv1a/GNA fusion protein was further investigated by feeding 2nd instar M. brassicae larvae on cabbage discs coated with purified recombinant proteins, an assay that might be more representative of situations in which Hv1a is employed on crops as a foliar bioinsecticide. The survival of larvae was significantly reduced when insects were fed on Hv1a/GNA-coated discs (FIG. 30) such that 15% and 20% of larvae remained after 10 days of exposure to discs coated with Hv1a/GNA at concentrations of 0.2% w/w and 0.1% w/w, respectively. In contrast, 80% survival was recorded for larvae reared for 10 days on discs coated with 0.2% w/w GNA, which was not significantly different to the 90% survival recorded for the control (no added protein) treatment. Fusion protein treatment survival curves were significantly different to both the GNA and control treatments (Kaplan-Meier; Mantel-Cox log-rank tests; $P<0.001$). Exposure to Hv1a/GNA-coated discs also retarded larval growth in surviving larvae. The reduction in growth was dose-dependent, so that by day 7 the average weight of surviving larvae fed on 0.2% or 0.1% w/w Hv1a/GNA was reduced by 90% and 76%, respectively, compared to the control treatment. GNA was also shown to reduce larval growth, so that by day 7 the average weight of larvae fed 0.2% w/w GNA was reduced by 45% compared to the control treatment.

Delivery of Ingested Hv1a/GNA to the Circulatory System and Binding of Injected Hv1a/GNA and GNA to the Central Nerve Chord To determine if the toxic effects observed in oral bioassays were attributable to GNA-mediated delivery of Hv1a to the circulatory system of M. brassicae larvae, haemolymph was extracted from insects fed on diets containing Hv1a/GNA and analysed for the presence of fusion protein by Western blotting using anti-GNA antibodies. A representative blot, depicted in FIG. 31A, confirms immunoreactivity of a major band corresponding to the molecular weight of intact fusion protein in samples from larvae fed Hv1a/GNA, but not control insects. As shown previously in FIG. 28C, fusion protein samples contain two GNA-immunoreactive bands corresponding to intact fusion protein and GNA from which the Hv1a peptide has been cleaved. Thus, the presence of a second smaller immunoreactive band in haemolymph samples from fusion protein fed larvae suggests uptake of both intact Hv1a/GNA and cleaved GNA, or cleavage of intact fusion protein after absorption in the insect gut. Cross-reactivity and poor sensitivity of the anti-Hv1a antibodies did not allow the detection of fusion protein or toxin when these antibodies were used to probe Western blots of larval haemolymph.

Figure 31:
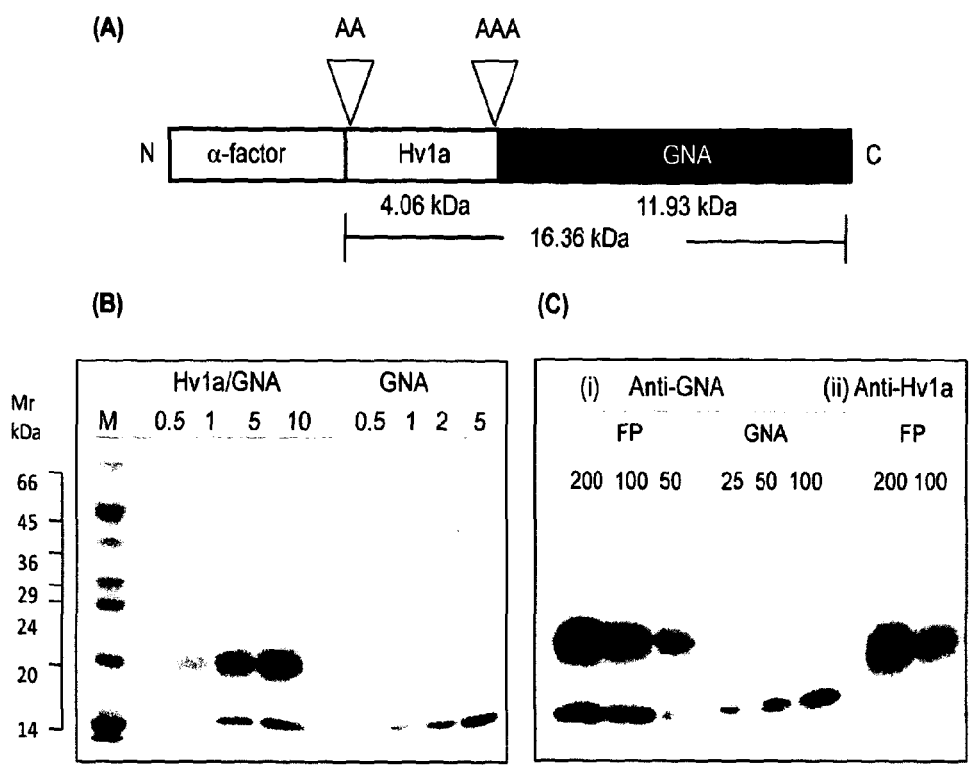

The above results indicate that the major reason for the improved oral activity of Hv1a when it is fused to GNA is the ability of this lectin to mediate delivery of Hv1a to the insect hemolymph. However, we also wondered whether GNA might also be able to enhance delivery of Hv1a to its sites of action in the insect nervous system. To investigate if GNA is able to bind to the nerve tract of lepidopteran larvae, intact nerve chords were dissected from insects injected with either GNA or Hv1a/GNA and analysed by Western blotting using anti-GNA antibodies. Nerve chords and haemolymph samples, pooled from 3-6 insects, were typically extracted 3-12 h following the injection of 10-20 μg of GNA or Hv1a/GNA. FIG. 31B shows positive immunoreactivity of bands corresponding in size to GNA and intact Hv1a/GNA fusion protein in both nerve chord and haemolymph samples taken from injected insects, which suggests that GNA is able to bind to the nerve tract of lepidopteran larvae. Bands corresponding to GNA or Hv1a/GNA fusion protein were not observed in nerve tissue extracted from insects fed on GNA or Hv1a/GNA (at 2.5 mg/5 g wet wt. diet), presumably due to the levels of bound protein being below the limits of detection of the anti-GNA antibodies.

Further evidence of the ability of GNA to bind to the central nerve chord was sought by visualisation of nerve chords dissected from insects that had been injected with, or fed on, fluorescently-labelled GNA or Hv1a/GNA. Control treatments were FITC-labelled ovalbumin or FITC alone. The visualisation of nerve chords dissected following injection was carried out on four separate occasions where typically 2-3 nerve chords per treatment were analysed and comparable results obtained. A composite showing different regions of M. brassicae nerve chords from different treatments is presented in FIG. 32. Low background fluorescence was observed in control FITC alone and FITC-labelled ovalbumin nerve chords. By contrast, fluorescence was observed along the entire length of the nerve tracts, including the terminal brain ganglion, of insects injected with FITC-labelled GNA or Hv1a/GNA. Fluorescence appeared to be predominantly localised to the nerve chord sheath. Reduced fluorescence was observed in instances where FITC-labelled GNA had been pre-incubated in the presence of mannose, suggesting that localisation to the nerve chord was mediated by binding of GNA to mannose-containing polypeptides in the nerve chord epithelium. However, binding was not completely inhibited under the conditions tested (results not shown). Similar results were obtained in experiments where larvae had been fed on diets containing FITC-labelled proteins although the levels of fluorescence were lower than those visualised from injected larvae (FIG. 32). This was attributed to lower levels of GNA and Hv1a/GNA being delivered to the circulatory system following ingestion as compared to the levels present in injected insects.

Discussion

Hva1 Retains Insecticidal Activity when Fused to GNA

Previously reported values for toxicity by injection of recombinant and synthetic Hv1a are highly variable, even when considering different species of the same genus. For example, the $ED_{50}$ reported for synthetic Hv1a against the cotton bollworm *Heliothis armigera* is 3 nmol/g (Atkinson R K, et al 1998) [7], which is more than 10-fold higher than the $PD_{50}$ dose of 250 pmol/g reported for the tobacco hornworm *Heliothis virescens* (Bloomquist (2003) [8]. In our hands, the doses of injected recombinant Hv1a and Hv1a/GNA required to induce flaccid paralysis and significant mortality of fifth stadium *M. brassicae* larvae were comparable (50-100 µg toxin/g insect equivalent to 12-25 nmoles/g), suggesting that HO a activity is not significantly compromised by C-terminal linkage to GNA. However, these doses are somewhat higher than those typically reported for recombinant Hv1a (e.g., $LD_{50}$ of 77 pmol/g and 716 pmol/g respectively for the housefly *Musca domestica* and lone star tick *Amblyomma americanum*; (Mukherjee A K et al 2006), [10]). Differences in the toxicity of HO a towards different species must, to a large degree, be determined by differences in the ability of the toxin to disrupt ion channel function. However, variability also derives from the use of different toxicity parameters (e.g., $LD_{50}$, $ED_{50}$ and $PD_{50}$), different sources of toxin (i.e. synthetic, recombinant or native peptide) and the suitability and/or ease of injection.

Fusion to GNA Massively Enhances the Oral Toxicity of Hv1a

Hv1a alone was not orally active when fed to the fifth stadium *M. brassicae* larvae. This is consistent with the observation that the $LD_{50}$ for Hv1a in the sheep blowfly *Lucilia cuprina* is 90-fold lower when the toxin is delivered per os compared with injection (V. Herzig and G. F. K, unpublished data). In striking contrast, the Hv1a/GNA fusion protein was orally toxic towards *M. brassicae* larvae in both cabbage leaf disc and droplet feeding assays. High levels of mortality and reduced growth were observed for second instar larvae exposed to discs coated with purified fusion protein. The oral toxicity observed in these assays must be a result of the Hv1a/GNA fusion protein, since GNA at a comparable dose did not reduce survival (although a reduced effect on larval growth was observed).

The consumption of droplets containing 40 µg of Hv1a/GNA fusion protein by fifth stadium larvae was seen to result in a complete cessation of feeding and larvae appeared relatively immobile, consistent with the previously described paralytic activity of the toxin (Fletcher J I et al 1997), (Tedford H W 2004b) [1,9]. Larvae failed to survive to pupation following droplet consumption of a total of 160 µg of fusion protein over four days. By contrast, larvae exposed to droplets containing an equivalent dose of Hv1a showed no evidence of reduced feeding or paralysis and all survived to pupation. The absence of oral toxicity for Hv1a contrasts with the previous results reporting 100% mortality of *Heliothis armigera* and *S. littoralis* exposed to transgenic tobacco expressing Hv1a (Khan S A 2006) [17]. One possibility is that natural insecticidal compounds produced by these plants might produce disturbances in the insect gut epithelium and thereby act synergistically with Hv1a to improve its oral activity.

GNA Mediates Delivery of Hv1a to Insect CNS

Most spider toxins act peripherally at neuromuscular junctions but Hv1a acts at sites within the central nervous system (Fletcher J I et al 1997) (Bloomquist (2003) [1,8]. Surprisingly, Western blot analysis of nerve chords dissected from insects injected with GNA and Hv1a/GNA indicated that GNA binds to the central nerve chord of lepidopteran larvae and is therefore capable of mediating the delivery of Hv1a to sites of action within the CNS. Further direct evidence for GNA localization to CNS was provided by fluorescence imagery of nerve chords dissected from larvae that had been injected with, or fed on, FITC-labelled proteins. That GNA binds to mannose-containing membrane-bound polypeptides was indicated by intense fluorescence of the nerve chord sheath and also by reduced binding in tissues extracted from insects injected with GNA that had been pre-incubated with mannose.

Neurophysiological studies with cockroaches, lepidopteran and dipteran larvae have indicated that Hv1a impairs ganglionic neural transmission, rather than conductance along the nerve chord. The characteristic delay in paralysis observed after injection of the toxin is thought to be attributable to the time required for the toxin to cross the nerve sheath and enter the CNS (Fletcher J I et al 1997) (Bloomquist (2003) [1,8]. The results presented here suggest that GNA may help to localise covalently attached insecticidal neurotoxins, such as Hv1a, to the CNS of exposed insects and thereby facilitate toxin action within the CNS.

In conclusion, the data presented here indicates that GNA not only mediates delivery of insecticidal peptides across the insect gut but that it is also capable of delivering peptides to the insect central nervous system. In the case of Hv1a, the massive improvement in oral activity upon fusion to GNA can be attributed to both of these properties. Many insecticidal peptides have been isolated from arachnid venoms (Tedford H W 2004b), (Gurevitz M et al 2007), (Windley M J at al 2012) [9,19,20], and fusion to GNA would appear to provide a general mechanism for dramatically enhancing their oral activity. GNA-toxin fusion proteins could be used for crop protection either as exogenously applied treatments or as endogenous proteins expressed in transgenic plants or entomopathogens.

Materials and Methods

Materials and Recombinant Techniques

General molecular biology protocols were as described in (Sambrook J et al 2001) [21] except where otherwise noted. Subcloning was carried out using the TOPO cloning kit (pCR2.1 TOPO vector; Invitrogen). *Pichia pastoris* SMD1168H (protease A deficient) strain, the expression vector pGAPZαB, and Easycomp *Pichia* transformation kit were from Invitrogen. Oligonucleotide primers were synthesised by Sigma-Genosys Ltd. T4 polynucleotide kinase was from Fermentas. Restriction endonucleases, T4 DNA ligase, and Pfu DNA polymerase were supplied by Promega. Plasmid DNA was prepared using Promega Wizard miniprepkits. GNA was produced as a recombinant protein in yeast using a clone generated as previously described (Raemaekers R J M at al 1999) [22]. Anti-GNA antibodies (raised in rabbits), were prepared by Genosys Biotechnologies, Cambridge, UK. Anti-ft/1a polyclonal antibodies (raised in rabbits) were prepared by the Institute of Medical and Veterinary Science, Adelaide, Australia. Recombinant Hv1a was prepared as described previously (Tedford H W et al 2004a), (Tedford H W et al 2001) [2,4].

All DNA sequencing was carried out using dideoxynucleotide chain termination protocols on Applied Biosystems automated DNA sequencers by the DNA Sequencing Service, School of Biological and Biomedical Sciences, University of Durham, UK. Sequences were checked and assembled using Sequencher software running on Mac OS computers.

Assembly of Expression Constructs for Production of Hv1a/GNA Fusion Protein

The Hv1a amino acid sequence (UniProtKB P56207) was used as the basis for assembly of a synthetic Hv1a gene. Codon usage was optimised for expression in yeast (www.yeastgenome.org/community/codonusage.shtml). The coding strand was subdivided into two fragments and the complementary strand was subdivided into three fragments, such that the coding fragments overlapped the complementary strand fragments by 21 bases. Five oligonucleotides based on these fragments were synthesised and used to assemble the mature Hv1a coding sequence (Table 6). All primers were individually 5'-phosphorylated using T4 polynucleotide kinase. An equimolar solution of 100 pmol of each phosphorylated primer was boiled for 10 min to denature secondary structures, then the solution was slowly cooled to room temperature (RT) to allow the primers to anneal. After addition of T4 DNA ligase, annealed oligonucleotides (in ligase buffer) were left to anneal for 15 h at 4° C. To obtain sufficient DNA for cloning into the yeast expression vector pGAPZαB, the Hv1a coding sequence was amplified by PCR using primers containing 5' PstI and 3' NotI restriction sites. Following amplification, gel purification and restriction digest, the PCR product was ligated into a previously generated yeast expression construct. (Trung N P at al 2006), [14] containing the mature GNA coding sequence (amino acids 1-105 derived from LECGNA2 cDNA; [23]) to create the plasmid Hv1a/GNA-pGAPZαB.

Expression and Purification of Hv1a/GNA Fusion Protein

Plasmid Hv1a/GNA-pGAPZαB DNA was transformed into chemically competent *P. pastoris* cells (strain SMD1168H) according to protocols supplied by Invitrogen. Transformants were selected by plating on medium containing zeocin (100 µg/ml). A clone expressing recombinant Hv1a/GNA was selected for production by bench-top fermentation by Western analysis using anti-GNA (1:3300 dilution) antibodies of supernatants from small-scale cultures grown at 30° C. for 2-3 days in YPG medium (1% w/v yeast extract; 2% w/v peptone; 4% v/v glycerol; 100 µg/ml zeocin) (results not shown).

For protein production, *P. pastoris* cells expressing Hv1a/GNA fusion protein or GNA encoding sequences were grown in a BioFlo 110 laboratory fermenter. Briefly, 3×100 ml YPG cultures (grown for 2-3 days at 30° C. with shaking) were used to inoculate 3 l of sterile minimal media supplemented with PTM1 trace salts (Higgins D R at al 1998) (Cino J (1999)) [24,25] Cultivation was conducted at 30° C., pH 4.5-5.0, 30% dissolved oxygen (cascaded agitation 250-750 rpm) with a glycerol feed (5-10 ml/h; 1.3 l over 72 h). Secreted proteins were separated from cells by centrifugation (30 min at 7500 g, 4° C.). NaCl was added to the supernatant to a final concentration of 2 M. Recombinant proteins were purified by hydrophobic interaction chromatography on a phenyl-Sepharose (Amersham Pharmacia Biotech) column (1 cm dia., 25 ml), run at 2 ml/min. After loading, the phenyl-Sepharose column was washed with 2 M NaCl and a linear salt gradient (2 M-0 M NaCl) applied over 60 min. Recombinant Hv1a/GNA eluted at ~1 M NaCl. Fractions containing purified proteins (analysed by SDS-PAGE) were then pooled, dialysed against distilled water and lyophilised. Lyophilised fusion protein and GNA were subject to gel filtration on Sephacryl S-200 columns (1.6 cm diameter, 90 cm length, flow rate 0.3 ml/min) to remove high molecular weight yeast proteins as described previously Trung N P et al 2006) [14]. Fractions containing purified recombinant proteins were again dialysed and lyophilised, or desalted and concentrated using Microsep™ centrifugal concentrators (VivaScience AG, Hannover, Germany).

Electrophoresis and Western Blotting

Proteins were routinely analysed by SDS-PAGE (17.5% acrylamide gels). Samples were prepared by adding 5×SDS sample buffer (containing 10% β-mercaptoethanol) and boiling for 10 min prior to loading. Gels were either stained with Coomassie blue or transferred to nitrocellulose for Western blotting using a Biorad Trans-blot SD semi dry transfer cell according to the manufacturer's recommendations. Western blotting of recombinant proteins and larval samples (haemolymph and nerve chord) using anti-GNA (1:3300 dilution) or anti-Hv1a (1:1000 dilution) antibodies was carried out as described (Fitches E et al 1998) [26].

FITC Labelling

Recombinant GNA, Hv1a/GNA, and ovalbumin (control) were fluorescently labelled with a 2:1 molar excess of fluorescein isothiocyanate (FITC, Sigma). Recombinant proteins (1 ml) were re-suspended at 2 mg/ml in 500 mM carbonate buffer pH 9.0 then incubated with 50 µl FITC (1 mg/ml in DMSO) with rotation for 4 h at RT, under dark conditions. Samples were dialysed against phosphate-buffered saline (PBS pH 7.4) at RT to remove excess FITC. FITC labelling of Hv1a was unsuccessful, presumably due to the scarcity of primary amines available for FITC attachment.

Insect Rearing

*M. brassicae* were originally obtained from cultures held at the Food and Environment Research Agency (FERA) and were reared at the University of Durham continuously on artificial diet (Bown D P at al 1997) [27] at 22-25° C. under a 16 h:8 h light:dark regime.

Injection Bioassays

Purified recombinant Hv1a peptide and Hv1a/GNA were tested for biological activity by injecting 4-5 µl of aqueous samples (lyophilised protein re-suspended in PBS) into newly enclosed fifth stadium *M. brassicae* larvae (40-70 mg). For each concentration tested, 10-20 larvae were injected and toxic effects were monitored over 4 days. PBS was injected as a negative control. Recombinant GNA is known to have no effect upon *M. brassicae* larvae when injected at up to 200 µg/larva (unpublished data).

Feeding Bioassays

Droplet Feeding Assays: *M. brassicae*

Several droplet-feeding assays were conducted to assess the oral activity of Hv1a/GNA towards *M. brassicae* fourth and fifth stadium larvae. Final sample numbers were relatively small (n=7-8 per treatment) as larvae were reluctant to ingest daily droplets and insects that did not consume a full 5-µl droplet were discarded from data sets. Two representative assays are described herein.

Droplet Assay 1:

Newly moulted fifth stadium larvae were fed daily for 4 days with a 5 µl droplet containing 40 µg of Hv1a/GNA or 9.6 µg of Hv1a toxin in 1×PBS and 10% sucrose solution. Control larvae were fed on droplets containing 40 µg bovine serum albumin (BSA). To encourage droplet consumption, larvae were starved for ~2-3 h prior to feeding. Larval weight was recorded daily ~1 h after droplet feeding. Treated larvae were placed individually in ventilated plastic pots (250 ml) with standard artificial diet. After 4 days of daily droplet feeding, larvae were maintained on optimal diet until the onset of pupation.

Droplet Assay 2:

Newly moulted fifth stadium larvae were fed on a single 5-0 droplet containing 40 μg of Hv1a/GNA or 40 μg BSA (control) in 1×PBS and 10% sucrose. Larvae were maintained as described above and weights recorded daily for 10 days.

Leaf Disc Assays: *M. brassicae*

The oral activity of Hv1a/GNA was further tested by feeding second instar *M. brassicae* larvae on cabbage (*Brassicae oleracea*) discs coated with purified fusion protein at concentrations of 0.2% w/w and 0.1% w/w (i.e., 10 mg/5 g and 5 mg/5 g leaf wet weight, respectively) or recombinant GNA at 0.2% w/w. Discs (~20 mm dia., 140 mg fresh wt.) were prepared by adding droplets of protein (re-suspended in 0.5×PBS and 0.1% v/v Tween) onto upper and lower surfaces of discs and air dried. Control discs were prepared with 0.5×PBS, 0.1% v/v Tween. Larvae were reared from hatch for 72 h on non-treated cabbage and then placed into ventilated plastic pots (250 ml) containing coated leaf discs and moist filter paper to prevent dessication. Freshly prepared discs were provided every 2-3 days. Two replicates of 10 larvae per treatment were assayed. Survival was recorded for 10 days. To minimise handling time, larval weights were recorded on days 4, 7, and 10.

Haemolymph Extraction and Nerve Chord Dissection

Haemolymph samples were extracted and prepared for Western analysis [12] from day 2 fifth instar larvae fed for 24 h on diet containing Hv1a/GNA at 2 mg/5 g wet wt. (~2% dietary protein). Typically, aliquots of two replicate samples containing pooled haemolymph (3-5 larva per sample) were run on SDS-PAGE gels and analysed by immunoblotting using anti-GNA antibodies. To investigate if GNA or Hv1a/GNA were localized to the CNS after oral delivery or injection, nerve chords were analysed by one of two methods. Nerve chords were dissected from sixth stadium larvae 4-24 h after injection or after being fed on droplets containing 20-50 μg GNA or fusion protein. Nerve tissue was subsequently analysed by Western blotting or visualised by fluorescent microscopy (section 2.11). Nerve chords were dissected as follows. Pre-chilled larvae were immersed in ice-cold distilled water prior to making a ventral incision from the tail to the head capsule. The resulting flaps of cuticle were fixed with pins into dissecting wax. The entire gut was carefully removed and the head capsule split to expose the terminal brain ganglia. Intact nerve chord and brain was then separated (using scissors) from the cuticle and head capsule and immersed immediately either in SDS sample buffer for Western analysis or in 3.7% w/v paraformaldehyde (PFA) for microscopy.

Fluorescent Microscopy

Nerve chords were extracted from sixth stadium larvae 4 h after injection of ~10 μg of FITC-labelled GNA or FITC-labelled Hv1a/GNA. Larvae were also injected with GNA that had been pre-incubated for 1 h at RT with 0.2 M mannose (methyl α-D-mannopyranoside). Nerve chords were also extracted from larvae after feeding on artificial diet containing FITC-labelled GNA or FITC-labelled Hv1a/GNA such that each larva consumed 50-100 μg labeled protein. Control treatments included FITC-labelled ovalbumin (10 μg per injection, 50-100 μg by ingestion) and FITC alone (0.5 μg per injection, 2.5 μg by ingestion). Following dissection and immersion in PFA (30-60 min), nerve chords were washed 3× in ice cold PBS (15 min per wash), mounted onto glass slides and overlaid with coverslips. Nerve chords were visualized using a fluorescent microscope (Nikon) under FITC filter (absorbance 494 nm; emission 521 nm) and images were captured in OpenLab.

Statistical Analysis

Data were analysed using Prism 5.0 (GraphPad Software Inc.). Kaplan-Meier insect survival curves were compared using Mantel-Cox log-rank tests. Insect weights were compared using either Student's t-tests or one-way analysis of variance (ANOVA), followed by Tukey-Kramer post hoc means separation. The accepted level of significance was $P<0.05$ in all cases.

TABLE 6

Oligonucleotide sequences used for assembly and amplification of a synthetic gene encoding for the mature Hv1a toxin.

Coding strand

Oligo 1:
(SEQ ID No: 22)
5'-<u>GCATCTCC</u>AACTTGTATTCCATCTGGTCAACCATGTCCATATA
ATGAAAATTGTTGT
Oligo 2:
(SEQ ID No: 23)
5'-
TCTCAATCTTGTACTTTTAAAGAAAATGAAAATGGTAATACTGTTAAAA
GATGTGAT<u>GC</u>

Complementary strand

Oligo 3:
(SEQ ID No: 24)
<u>ACGT</u>CGTAGAGGTTGAACATAAGGTAGACCAGTTGGTACA
Oligo 4:
(SEQ ID No: 25)
GGTATATTACTTTTAACAACAAGAGTTAGAACATGAAAATTT
Oligo 5:
(SEQ ID No: 26)
CTTTTACTTTTACCATTATGACAATTTTCTACACTA<u>CGCCGG</u>

Primers for amplification of full-length sequence

Forward primer:
(SEQ ID No: 27)
5' TTA<u>CTGCAG</u>CATCTCCAACTTGTATTCC
Reverse primer:
(SEQ ID No: 28)
5' TTA<u>GCGGCCGC</u>ATCACATCTTTTAACAG Underlined bases depict restriction sites (PstI and Not I) used for ligation of the full-length fragment into the yeast expression vector pGAPZαB.

TABLE 7

Mortality recorded for fifth stadium *M. brassicae* larvae 72 h after injection of different concentrations of recombinant Hv1a and Hv1a/GNA.

| Treatment | Dose (μg/insect) (Hv1a equivalents) | Mortality (%) | Sample No. |
|---|---|---|---|
| Control | — | 0 | 20 |
| Hv1a | 184 | 90* | 10 |
|  | 92 | 80* | 10 |
|  | 46 | 20 | 10 |
| Hv1a/GNA | 100 | 90* | 20 |
|  | 50 | 45* | 20 |
|  | 25 | 0 | 20 |

Doses of injected Hv1a/GNA are expressed as Hv1a equivalents to allow a direct comparison with the Hv1a treatment and are based on a mean larval weight at injection of 50 mg. Asterisks denotes significant difference in survival between control and toxin treatment (P<0.0001).

REFERENCES

1. Fletcher J I, Smith R, O'Donoghue S I, Nilges M, Connor M, et al. (1997) The structure of a novel insecticidal neurotoxin, ω-atracotoxin-HV1, from the venom of an Australian funnel web spider. Nat Struct. Biol 4: 559-566.
2. Tedford H W, Gilles N, Ménez A, Doering C J, Zamponi G W, et al. (2004a) Scanning mutagenesis of ω-atracotoxin-Hv1a reveals a spatially restricted epitope that confers selective activity against invertebrate calcium channels. J Biol Chem 279: 44133-44140.
4. Tedford H W, Fletcher J I, King G F (2001) Functional significance of the β-hairpin in the insecticidal neurotoxin ω-atracotoxin-Hv1a. J Biol Chem 276: 26568-26576.
7. Atkinson R K, Howden M E H, Tyler M I, Vonarx E J (June 1998) Insecticidal toxins derived from funnel web (*Atrax* or *Hadronyche*) spiders U.S. Pat. No. 5,763,568
8. Bloomquist (2003) Mode of action of atracotoxin at central and peripheral synapses of insects. Invert Neurosci 5: 45-50.
9. Tedford H W, Sollod B L, Maggio F, King G F (2004b) Australian funnel-web spiders: master insecticide chemists. Toxicon 43: 601-618.
10. Mukherjee A K, Sollod B L, Wikel S K, King G F (2006) Orally active acaricidal peptide toxins from spider venom. Toxicon 47: 182-187.
14. Trung N P, Fitches E, Gatehouse J A (2006) A fusion protein containing a lepidopteran-specific toxin from the South Indian red scorpion (*Mesobuthus tamulus*) and snowdrop lectin shows oral toxicity to target insects. BMC Biotech 6:18.
17. Khan S A, Zafar Y, Briddon R W, Malik K A, Mukhtar Z (2006) Spider venom toxin protects plants from insect attack. Transgenic Res 15: 349-357,
19. Gurevitz M, Karbat I, Cohen L, Ilan N, Kahn R et al. (2007) Toxicon 49:473-489,
20. Windley M J, Herzig V, Dziemborowicz S A, Hardy M C, King G F et al. (2012) Spider-venom peptides as bioinsecticides. Toxins: In press.
21. Sambrook J, Russell D W (2001) Molecular cloning: A laboratory manual, 3rd edn, Spring Harbor, N.Y.: Cold Spring Harbor Laboratory.
22. Raemaekers R J M, deMuro L, Gatehouse J A, FordhamSkelton A P (1999) Functional phytohemagglutinin (PHA) and *Galanthus nivalis* agglutinin (GNA) expressed in *Pichia pastoris*—Correct N terminal processing and secretion of heterologous proteins expressed using the PHA-E signal peptide. Eur J Biochem 265:394-403.
26. Fitches E, Gatehouse J A (1998) A comparison of the short and long term effects of insecticidal lectins on the activities of soluble and brush border enzymes of tomato moth larvae (*Lacanobia oleracea*). J Insect Phys 44:1213-1224.
27. Bown D P, Wilkinson H S, Gatehouse J A, (1997) Differentially regulated inhibitor sensitive and insensitive protease genes from the phytophagous insect pest *Helicoverpa armigera*, are members of complex multi-gene families. Insect Biochem Mol Biol 27: 625-638.

What is claimed is:

1. A fusion protein comprising: (i) an omega atracotoxin family member 1a protein from *Hadronyche versuta* (ω-ACTX-Hv1a) protein toxin comprising the amino acid sequence: SPTCIPSGQPCPYNENCCSQSCT-FKENENGNTVKRCD (SEQ ID NO: 1), or a variant of ω-ACTX-Hv1a protein toxin having at least 95% identity to SEQ ID NO: 1, operably linked to (ii) a protein capable of mediating translocation of the fusion protein from the invertebrate gut, wherein the protein capable of mediating translocation is a snowdrop lectin (GNA) comprising the sequence of SEQ ID NO: 3 and wherein the fusion protein comprises the amino acid sequence of any of SEQ ID NOs: 4, 5, 6, 7, 8 or 9.

2. The fusion protein of claim 1 wherein the fusion protein further comprises an affinity tag to aid purification.

3. The fusion protein of claim 1 wherein the protein has pesticide activity against invertebrate pests selected from the group consisting of insects, arthropods, nematodes, and molluscs.

4. A method of preparing a fusion protein comprising culturing a host cell comprising a nucleic acid encoding the fusion protein of claim 1 under conditions suitable for expression of the fusion protein.

5. The method of claim 4 further comprising the step of recovering the fusion protein.

6. A pesticide composition comprising the fusion protein of claim 1 in an effective pesticidal amount, together with one or more suitable carriers, diluents, adjuvants, preservatives, dispersants, solvents, and emulsifying agents.

7. A method for the preparation of a pesticide composition which comprises mixing an effective pesticidal amount of the fusion protein of claim 1 with one or more suitable carriers, diluents, adjuvants, preservatives, dispersants, solvents, or emulsifying agents.

8. A method of preventing or treating a pest infection of a plant comprising applying a quantity of a composition comprising the fusion protein according to claim 1 to the plant or its locus of growth.

9. A method of preventing or treating a mollusc or nematode pest infection of a plant comprising applying a quantity of a composition comprising the fusion protein according to claim 1 to the plant or its locus of growth; or introducing to the plant a nucleic acid sequence encoding said fusion protein.

10. The method of claim 9 wherein the pest is a slug or snail.

11. A molluscicide bait composition comprising the fusion protein of claim 1.

12. A transgenic plant or progeny thereof comprising the fusion protein of claim 1.

13. A method of preventing or treating a pest infection of a plant comprising applying a quantity of the pesticide composition according to claim 6, to the plant or its locus of growth.

14. A method of preventing or treating a mollusc or nematode pest infection of a plant comprising applying a quantity of the pesticide composition according to claim 6, to the plant or its locus of growth; or introducing to the plant a nucleic acid sequence encoding said fusion protein by transformation with *Agrobacterium*, particle bombardment, electroporation or viral transformation.

15. A molluscicide bait composition comprising the pesticide composition according to claim 6.

16. The fusion protein of claim 1 wherein the fusion protein comprises a w-ACTX-Hv1a protein toxin having the sequence of SEQ ID NO: 1.

17. The fusion protein of claim 1, wherein the fusion protein comprises a variant of ω-ACTX-Hv1 a protein toxin having at least 95% identity to SEQ ID NO: 1, and wherein amino acid K34 of the ω-ACTX-Hv1a protein toxin of SEQ ID NO: 1 is modified.

18. The fusion protein of claim 17 wherein the variant of ω-ACTX-Hv1a protein toxin has a K34Q substitution.

* * * * *

```
SEQUENCE LISTING

<160> NUMBER OF SEQ ID NOS: 28

<210> SEQ ID NO 1
<211> LENGTH: 37
<212> TYPE: PRT
<213> ORGANISM: Hadronyche versuta

<400> SEQUENCE: 1

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35

<210> SEQ ID NO 2
<211> LENGTH: 37
<212> TYPE: PRT
<213> ORGANISM: Artificial Sequence
<220> FEATURE:
<223> OTHER INFORMATION: modified natural toxin sequence

<400> SEQUENCE: 2

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Gln Arg Cys Asp
        35
```

<210> SEQ ID NO 3
<211> LENGTH: 105
<212> TYPE: PRT
<213> ORGANISM: Galanthus nivalis

<400> SEQUENCE: 3

Asp Asn Ile Leu Tyr Ser Gly Glu Thr Leu Ser Thr Gly Glu Phe Leu
1               5                   10                  15

Asn Tyr Gly Ser Phe Val Phe Ile Met Gln Glu Asp Cys Asn Leu Val
            20                  25                  30

Leu Tyr Asp Val Asp Lys Pro Ile Trp Ala Thr Asn Thr Gly Gly Leu
        35                  40                  45

Ser Arg Ser Cys Phe Leu Ser Met Gln Thr Asp Gly Asn Leu Val Val
    50                  55                  60

Tyr Asn Pro Ser Asn Lys Pro Ile Trp Ala Ser Asn Thr Gly Gly Gln
65                  70                  75                  80

Asn Gly Asn Tyr Val Cys Ile Leu Gln Lys Asp Arg Asn Val Val Ile
                85                  90                  95

Tyr Gly Thr Asp Arg Trp Ala Thr Gly
            100                 105

<210> SEQ ID NO 4
<211> LENGTH: 153
<212> TYPE: PRT
<213> ORGANISM: Artificial Sequence
<220> FEATURE:
<223> OTHER INFORMATION: Fusion protein

<400> SEQUENCE: 4

Asp Asn Ile Leu Tyr Ser Gly Glu Thr Leu Ser Thr Gly Glu Phe Leu
1               5                   10                  15

Asn Tyr Gly Ser Phe Val Phe Ile Met Gln Glu Asp Cys Asn Leu Val
            20                  25                  30

Leu Tyr Asp Val Asp Lys Pro Ile Trp Ala Thr Asn Thr Gly Gly Leu
        35                  40                  45

Ser Arg Ser Cys Phe Leu Ser Met Gln Thr Asp Gly Asn Leu Val Val
    50                  55                  60

Tyr Asn Pro Ser Asn Lys Pro Ile Trp Ala Ser Asn Thr Gly Gly Gln
65                  70                  75                  80

Asn Gly Asn Tyr Val Cys Ile Leu Gln Lys Asp Arg Asn Val Val Ile
                85                  90                  95

Tyr Gly Thr Asp Arg Trp Ala Thr Gly Ala Ala Ala Ser Pro Thr Cys
            100                 105                 110

Ile Pro Ser Gly Gln Pro Cys Pro Tyr Asn Glu Asn Cys Cys Ser Gln
        115                 120                 125

Ser Cys Thr Phe Lys Glu Asn Glu Asn Gly Asn Thr Val Lys Arg Cys
    130                 135                 140

Asp Val Asp His His His His His
145                 150

<210> SEQ ID NO 5
<211> LENGTH: 151
<212> TYPE: PRT
<213> ORGANISM: Artificial Sequence
<220> FEATURE:
<223> OTHER INFORMATION: Fusion protein

<400> SEQUENCE: 5

```
His His His His His Asp Asn Ile Leu Tyr Ser Gly Glu Thr Leu
1               5                   10                  15

Ser Thr Gly Glu Phe Leu Asn Tyr Gly Ser Phe Val Phe Ile Met Gln
            20                  25                  30

Glu Asp Cys Asn Leu Val Leu Tyr Asp Val Asp Lys Pro Ile Trp Ala
            35                  40                  45

Thr Asn Thr Gly Gly Leu Ser Arg Ser Cys Phe Leu Ser Met Gln Thr
 50                  55                  60

Asp Gly Asn Leu Val Val Tyr Asn Pro Ser Asn Lys Pro Ile Trp Ala
 65                  70                  75                  80

Ser Asn Thr Gly Gly Gln Asn Gly Asn Tyr Val Cys Ile Leu Gln Lys
                85                  90                  95

Asp Arg Asn Val Val Ile Tyr Gly Thr Asp Arg Trp Ala Thr Gly Ala
            100                 105                 110

Ala Ala Ser Pro Thr Cys Ile Pro Ser Gly Gln Pro Cys Pro Tyr Asn
            115                 120                 125

Glu Asn Cys Cys Ser Gln Ser Cys Thr Phe Lys Glu Asn Glu Asn Gly
            130                 135                 140

Asn Thr Val Gln Arg Cys Asp
145                 150
```

<210> SEQ ID NO 6
<211> LENGTH: 146
<212> TYPE: PRT
<213> ORGANISM: Artificial Sequence
<220> FEATURE:
<223> OTHER INFORMATION: Fusion protein

<400> SEQUENCE: 6

```
Ala Ser Pro Thr Cys Ile Pro Ser Gly Gln Pro Cys Pro Tyr Asn Glu
1               5                   10                  15

Asn Cys Cys Ser Gln Ser Cys Thr Phe Lys Glu Asn Glu Asn Gly Asn
            20                  25                  30

Thr Val Lys Arg Cys Asp Ala Ala Ala Asp Asn Ile Leu Tyr Ser Gly
            35                  40                  45

Glu Thr Leu Ser Thr Gly Glu Phe Leu Asn Tyr Gly Ser Phe Val Phe
 50                  55                  60

Ile Met Gln Glu Asp Cys Asn Leu Val Leu Tyr Asp Val Asp Lys Pro
 65                  70                  75                  80

Ile Trp Ala Thr Asn Thr Gly Gly Leu Ser Arg Ser Cys Phe Leu Ser
            85                  90                  95

Met Gln Thr Asp Gly Asn Leu Val Val Tyr Asn Pro Ser Asn Lys Pro
            100                 105                 110

Ile Trp Ala Ser Asn Thr Gly Gly Gln Asn Gly Asn Tyr Val Cys Ile
            115                 120                 125

Leu Gln Lys Asp Arg Asn Val Val Ile Tyr Gly Thr Asp Arg Trp Ala
            130                 135                 140

Thr Gly
145
```

<210> SEQ ID NO 7
<211> LENGTH: 154
<212> TYPE: PRT
<213> ORGANISM: Artificial Sequence
<220> FEATURE:
<223> OTHER INFORMATION: Fusion protein

<400> SEQUENCE: 7

```
Ala Ser Pro Thr Cys Ile Pro Ser Gly Gln Pro Cys Pro Tyr Asn Glu
1               5                   10                  15

Asn Cys Cys Ser Gln Ser Cys Thr Phe Lys Glu Asn Glu Asn Gly Asn
                20                  25                  30

Thr Val Lys Arg Cys Asp Ala Ala Asp Asn Ile Leu Tyr Ser Gly
            35                  40                  45

Glu Thr Leu Ser Thr Gly Glu Phe Leu Asn Tyr Gly Ser Phe Val Phe
    50                  55                      60

Ile Met Gln Glu Asp Cys Asn Leu Val Leu Tyr Asp Val Asp Lys Pro
65                  70                  75                  80

Ile Trp Ala Thr Asn Thr Gly Gly Leu Ser Arg Ser Cys Phe Leu Ser
                85                  90                  95

Met Gln Thr Asp Gly Asn Leu Val Val Tyr Asn Pro Ser Asn Lys Pro
                100                 105                 110

Ile Trp Ala Ser Asn Thr Gly Gly Gln Asn Gly Asn Tyr Val Cys Ile
            115                 120                 125

Leu Gln Lys Asp Arg Asn Val Val Ile Tyr Gly Thr Asp Arg Trp Ala
    130                 135                 140

Thr Gly Val Asp His His His His His
145                 150

<210> SEQ ID NO 8
<211> LENGTH: 146
<212> TYPE: PRT
<213> ORGANISM: Artificial Sequence
<220> FEATURE:
<223> OTHER INFORMATION: Fusion protein

<400> SEQUENCE: 8

Ala Ser Pro Thr Cys Ile Pro Ser Gly Gln Pro Cys Pro Tyr Asn Glu
1               5                   10                  15

Asn Cys Cys Ser Gln Ser Cys Thr Phe Lys Glu Asn Glu Asn Gly Asn
                20                  25                  30

Thr Val Gln Arg Cys Asp Ala Ala Asp Asn Ile Leu Tyr Ser Gly
            35                  40                  45

Glu Thr Leu Ser Thr Gly Glu Phe Leu Asn Tyr Gly Ser Phe Val Phe
    50                  55                      60

Ile Met Gln Glu Asp Cys Asn Leu Val Leu Tyr Asp Val Asp Lys Pro
65                  70                  75                  80

Ile Trp Ala Thr Asn Thr Gly Gly Leu Ser Arg Ser Cys Phe Leu Ser
                85                  90                  95

Met Gln Thr Asp Gly Asn Leu Val Val Tyr Asn Pro Ser Asn Lys Pro
                100                 105                 110

Ile Trp Ala Ser Asn Thr Gly Gly Gln Asn Gly Asn Tyr Val Cys Ile
            115                 120                 125

Leu Gln Lys Asp Arg Asn Val Val Ile Tyr Gly Thr Asp Arg Trp Ala
    130                 135                 140

Thr Gly
145

<210> SEQ ID NO 9
<211> LENGTH: 152
<212> TYPE: PRT
<213> ORGANISM: Artificial Sequence
<220> FEATURE:
<223> OTHER INFORMATION: Fusion protein
```

<400> SEQUENCE: 9

```
Ala Ser Pro Thr Cys Ile Pro Ser Gly Gln Pro Cys Pro Tyr Asn Glu
1               5                   10                  15

Asn Cys Cys Ser Gln Ser Cys Thr Phe Lys Glu Asn Glu Asn Gly Asn
            20                  25                  30

Thr Val Gln Arg Cys Asp Ala Ala Asp Asn Ile Leu Tyr Ser Gly
        35                  40                  45

Glu Thr Leu Ser Thr Gly Glu Phe Leu Asn Tyr Gly Ser Phe Val Phe
    50                  55                  60

Ile Met Gln Glu Asp Cys Asn Leu Val Leu Tyr Asp Val Asp Lys Pro
65              70                  75                  80

Ile Trp Ala Thr Asn Thr Gly Gly Leu Ser Arg Ser Cys Phe Leu Ser
                85                  90                  95

Met Gln Thr Asp Gly Asn Leu Val Val Tyr Asn Pro Ser Asn Lys Pro
            100                 105                 110

Ile Trp Ala Ser Asn Thr Gly Gly Gln Asn Gly Asn Tyr Val Cys Ile
            115                 120                 125

Leu Gln Lys Asp Arg Asn Val Val Ile Tyr Gly Thr Asp Arg Trp Ala
    130                 135                 140

Thr Gly His His His His His His
145                 150
```

<210> SEQ ID NO 10
<211> LENGTH: 246
<212> TYPE: PRT
<213> ORGANISM: Artificial Sequence
<220> FEATURE:
<223> OTHER INFORMATION: Fusion protein

<400> SEQUENCE: 10

```
Met Arg Phe Pro Ser Phe Leu Leu Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65              70                  75                  80

Ser Leu Glu Lys Arg Glu Ala Glu Ala Ala Ser Pro Thr Cys Ile
            85                  90                  95

Pro Ser Gly Gln Pro Cys Pro Tyr Asn Glu Asn Cys Cys Ser Gln Ser
            100                 105                 110

Cys Thr Phe Lys Glu Asn Glu Asn Gly Asn Thr Val Gln Arg Cys Asp
        115                 120                 125

Ala Ala Ala Asp Asn Ile Leu Tyr Ser Gly Glu Thr Leu Ser Thr Gly
    130                 135                 140

Glu Phe Leu Asn Tyr Gly Ser Phe Val Phe Ile Met Gln Glu Asp Cys
145                 150                 155                 160

Asn Leu Val Leu Tyr Asp Val Asp Lys Pro Ile Trp Ala Thr Asn Thr
                165                 170                 175

Gly Gly Leu Ser Arg Ser Cys Phe Leu Ser Met Gln Thr Asp Gly Asn
            180                 185                 190

Leu Val Val Tyr Asn Pro Ser Asn Lys Pro Ile Trp Ala Ser Asn Thr
```

```
                195                 200                 205
Gly Gly Gln Asn Gly Asn Tyr Val Cys Ile Leu Gln Lys Asp Arg Asn
            210                 215                 220

Val Val Ile Tyr Gly Thr Asp Arg Trp Ala Thr Gly Val Asp His His
225                 230                 235                 240

His His His His Ser Arg
                245

<210> SEQ ID NO 11
<211> LENGTH: 111
<212> TYPE: DNA
<213> ORGANISM: Artificial Sequence
<220> FEATURE:
<223> OTHER INFORMATION: nucleic acid encoding modified toxin

<400> SEQUENCE: 11
tctccaactt gtattccatc tggtcaacca tgtccatata atgaaaattg ttgttctcaa    60
tcttgtactt taaagaaaaa tgaaaatggt aatactgttc aaagatgtga t            111

<210> SEQ ID NO 12
<211> LENGTH: 314
<212> TYPE: DNA
<213> ORGANISM: Galanthus nivalis

<400> SEQUENCE: 12
gacaatattt tgtactccgg tgagactctc tctacagggg aatttctcaa ctacggaagt    60
ttcgttttta tcatgcaaga ggactgcaat ctggtcttgt acgacgtgga caagccaatc   120
tgggcaacaa acacaggtgg tctctcccgt agctgcttcc tcagcatgca gactgatggg   180
aacctcgtgg tgtacaaccc atcgaacaaa ccgatttggg caagcaacac tggaggccaa   240
aatgggaatt acgtgtgcat cctacagaag gataggaatg ttgtgatcta cggaactgat   300
cgttgggcca ctgg                                                    314

<210> SEQ ID NO 13
<211> LENGTH: 735
<212> TYPE: DNA
<213> ORGANISM: Artificial Sequence
<220> FEATURE:
<223> OTHER INFORMATION: nucleic acid for signal peptide fused to fusion
      protein

<400> SEQUENCE: 13
atgagatttc cttcattttt actgctggtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaaggggta   240
tctctcgaga aaagagaggc tgaagctgca gcatctccaa cttgtattcc atctggtcaa   300
ccatgtccat ataatgaaaa ttgttgttct caatcttgta cttttaaaga aaatgaaaat   360
ggtaatactg ttcaaagatg tgatgcggcc gccgacaata ttttgtactc cggtgagact   420
ctctctacag gggaatttct caactacgga agtttcgttt ttatcatgca agaggactgc   480
aatctggtct gtacgacgt ggacaagcca atctgggcaa caaacacagg tggtctctcc   540
cgtagctgct tcctcagcat gcagactgat gggaacctcg tggtgtacaa cccatcgaac   600
aaaccgattt gggcaagcaa cactggaggc caaaatggga attacgtgtg catcctacag   660
aaggatagga atgttgtgat ctacggaact gatcgttggg ccactggagt ggaccatcat   720
```
catcatcatc attga 735

<210> SEQ ID NO 14
<211> LENGTH: 37
<212> TYPE: PRT
<213> ORGANISM: Mesobuthus tamulus

<400> SEQUENCE: 14

Arg Cys Gly Pro Cys Phe Thr Thr Asp Pro Gln Thr Gln Ala Lys Cys
1               5                   10                  15

Ser Glu Cys Cys Gly Arg Lys Gly Val Cys Lys Gly Pro Gln Cys
            20                  25                  30

Ile Cys Gly Ile Gln
        35

<210> SEQ ID NO 15
<211> LENGTH: 23
<212> TYPE: PRT
<213> ORGANISM: Artificial Sequence
<220> FEATURE:
<223> OTHER INFORMATION: GNA signal peptide

<400> SEQUENCE: 15

Met Ala Lys Ala Ser Leu Leu Ile Leu Ala Ala Ile Phe Leu Gly Val
1               5                   10                  15

Ile Thr Pro Ser Cys Leu Ser
            20

<210> SEQ ID NO 16
<211> LENGTH: 171
<212> TYPE: PRT
<213> ORGANISM: Artificial Sequence
<220> FEATURE:
<223> OTHER INFORMATION: Fusion protein

<400> SEQUENCE: 16

Met Ala Lys Ala Ser Leu Leu Ile Leu Ala Ala Ile Phe Leu Gly Val
1               5                   10                  15

Ile Thr Pro Ser Cys Leu Ser Ala Ala Ala Arg Cys Gly Pro Cys Phe
            20                  25                  30

Thr Thr Asp Pro Gln Thr Gln Ala Lys Cys Ser Glu Cys Cys Gly Arg
        35                  40                  45

Lys Gly Val Cys Lys Gly Pro Gln Cys Ile Cys Gly Ile Gln Ala
    50                  55                  60

Ala Ala Asp Asn Ile Leu Tyr Ser Gly Glu Thr Leu Ser Thr Gly Glu
65                  70                  75                  80

Phe Leu Asn Tyr Gly Ser Phe Val Phe Ile Met Gln Glu Asp Cys Asn
                85                  90                  95

Leu Val Leu Tyr Asp Val Asp Lys Pro Ile Trp Ala Thr Asn Thr Gly
            100                 105                 110

Gly Leu Ser Arg Ser Cys Phe Leu Ser Met Gln Thr Asp Gly Asn Leu
        115                 120                 125

Val Val Tyr Asn Pro Ser Asn Lys Pro Ile Trp Ala Ser Asn Thr Gly
    130                 135                 140

Gly Gln Asn Gly Asn Tyr Val Cys Ile Leu Gln Lys Asp Arg Asn Val
145                 150                 155                 160

Val Ile Tyr Gly Thr Asp Arg Trp Ala Thr Gly
                165                 170

<210> SEQ ID NO 17
<211> LENGTH: 516
<212> TYPE: DNA
<213> ORGANISM: Artificial Sequence
<220> FEATURE:
<223> OTHER INFORMATION: nucleic acid for fusion protein

<400> SEQUENCE: 17

```
atggctaagg caagtctcct cattttggcc gccatcttcc ttggtgtcat cacaccatct      60
tgcctgagtg ctgcagcaag gtgtggtcct tgctttacaa ctgatcctca aacacaagcc     120
aagtgtagtg agtgttgtgg gcgaaagggt ggagtatgca agggcccaca atgtatctgt     180
ggtatacaag cggccgccga caatattttg tactccggtg agactctctc tacaggggaa     240
tttctcaact acggaagttt cgttttatc atgcaagagg actgcaatct ggtcttgtac      300
gacgtggaca agccaatctg gcaacaaac acaggtggtc tctcccgtag ctgcttcctc      360
agcatgcaga ctgatgggaa cctcgtggtg tacaacccat cgaacaaacc gatttgggca     420
agcaacactg gaggccaaaa tgggaattac gtgtgcatcc tacagaagga taggaatgtt     480
gtgatctacg gaactgatcg ttgggctact ggatga                              516
```

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 18

```
tggtctctcc cgtagctgct t                                               21
```

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 19

```
atcgaacaaa ccgatttggg                                                 20
```

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 20

```
cggtatgtgt aaggccggat a                                               21
```

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 21

```
acgaccgatg ggaacactgt                                                 20
```

<210> SEQ ID NO 22
<211> LENGTH: 57

<212> TYPE: DNA
<213> ORGANISM: Artificial Sequence
<220> FEATURE:
<223> OTHER INFORMATION: Oligonucleotide sequence

<400> SEQUENCE: 22
gcatctccaa cttgtattcc atctggtcaa ccatgtccat ataatgaaaa ttgttgt       57

<210> SEQ ID NO 23
<211> LENGTH: 59
<212> TYPE: DNA
<213> ORGANISM: Artificial Sequence
<220> FEATURE:
<223> OTHER INFORMATION: Oligonucleotide sequence

<400> SEQUENCE: 23
tctcaatctt gtacttttaa agaaaatgaa aatggtaata ctgttaaaag atgtgatgc    59

<210> SEQ ID NO 24
<211> LENGTH: 40
<212> TYPE: DNA
<213> ORGANISM: Artificial Sequence
<220> FEATURE:
<223> OTHER INFORMATION: Oligonucleotide sequence

<400> SEQUENCE: 24
acgtcgtaga ggttgaacat aaggtagacc agttggtaca                         40

<210> SEQ ID NO 25
<211> LENGTH: 42
<212> TYPE: DNA
<213> ORGANISM: Artificial Sequence
<220> FEATURE:
<223> OTHER INFORMATION: Oligonucleotide sequence

<400> SEQUENCE: 25
ggtatattac ttttaacaac aagagttaga acatgaaaat tt                      42

<210> SEQ ID NO 26
<211> LENGTH: 42
<212> TYPE: DNA
<213> ORGANISM: Artificial Sequence
<220> FEATURE:
<223> OTHER INFORMATION: Oligonucleotide sequence

<400> SEQUENCE: 26
cttttacttt taccattatg acaattttct acactacgcc gg                      42

<210> SEQ ID NO 27
<211> LENGTH: 28
<212> TYPE: DNA
<213> ORGANISM: Artificial Sequence
<220> FEATURE:
<223> OTHER INFORMATION: Oligonucleotide sequence

<400> SEQUENCE: 27
taactgcagc atctccaact tgtattcc                                      28

<210> SEQ ID NO 28
<211> LENGTH: 28
<212> TYPE: DNA
<213> ORGANISM: Artificial Sequence
<220> FEATURE:
<223> OTHER INFORMATION: Oligonucleotide sequence

```
<400> SEQUENCE: 28
ttagcggccg catcacatct tttaacag                                            28
```